US008740963B2

(12) United States Patent
Arbefeuille et al.

(10) Patent No.: US 8,740,963 B2
(45) Date of Patent: Jun. 3, 2014

(54) METHODS OF IMPLANTING A PROSTHESIS AND TREATING AN ANEURYSM

(75) Inventors: Samuel Arbefeuille, Hollywood, FL (US); Humberto Berra, Cooper City, FL (US); Carol Barbre, Fort Lauderdale, FL (US); Michael Moore, Fort Lauderdale, FL (US)

(73) Assignee: Bolton Medical, Inc., Sunrise, FL (US)

( * ) Notice: Subject to any disclaimer, the term of this patent is extended or adjusted under 35 U.S.C. 154(b) by 1280 days.

(21) Appl. No.: 11/449,337

(22) Filed: Jun. 8, 2006

(65) Prior Publication Data
US 2006/0276872 A1 Dec. 7, 2006

Related U.S. Application Data

(63) Continuation-in-part of application No. 10/784,462, filed on Feb. 23, 2004, now Pat. No. 8,292,943, and a continuation-in-part of application No. 10/884,136, filed on Jul. 2, 2004, now Pat. No. 7,763,063.

(60) Provisional application No. 60/499,652, filed on Sep. 3, 2003, provisional application No. 60/500,155, filed on Sep. 4, 2003.

(51) Int. Cl.
*A61F 2/06* (2013.01)
(52) U.S. Cl.
USPC ........................................ 623/1.12; 623/1.11
(58) Field of Classification Search
USPC .............................................. 623/1.11, 1.12
See application file for complete search history.

(56) References Cited

U.S. PATENT DOCUMENTS

| 3,416,531 A | 12/1968 | Edwards |
| 3,485,234 A | 12/1969 | Stevens |

(Continued)

FOREIGN PATENT DOCUMENTS

| CN | 2451136 Y | 10/2001 |
| DE | 197 53 123 A1 | 8/1999 |

(Continued)

OTHER PUBLICATIONS

Notification of Transmittal of The International Search Report and the Written Opinion or the International Searching Authority, or the Declaration for International Application No. PCT/US04/28530, mailed Sep. 15, 2005.

(Continued)

*Primary Examiner* — Darwin Erezo
*Assistant Examiner* — Diane Yabut
(74) *Attorney, Agent, or Firm* — Hamilton, Brook, Smith & Reynolds, P.C.

(57) ABSTRACT

A method of implanting a prosthesis in a patient at a treatment site includes providing a prosthesis delivery system with an inner sheath and an outer sheath. The prosthesis is loaded inside the inner sheath. The inner sheath containing the prosthesis is loaded within the outer sheath. The outer sheath is advanced in a patient towards the treatment site up to a given position at a distance from the treatment site. While retaining the outer sheath in the given position, the inner sheath is advanced out from the outer sheath to the treatment site to align the prosthesis with the treatment site and the inner sheath is retracted to at least partially implant the prosthesis at the treatment site. Upon completion of prosthesis implantation, both of the inner and outer sheaths are retracted from the patient.

14 Claims, 24 Drawing Sheets

(56) References Cited

U.S. PATENT DOCUMENTS

| | | |
|---|---|---|
| 3,502,069 A | 3/1970 | Silverman |
| 3,868,956 A | 3/1975 | Alfidi et al. |
| 4,351,333 A | 9/1982 | Lazarus et al. |
| 4,425,919 A | 1/1984 | Alston, Jr. et al. |
| 4,487,808 A | 12/1984 | Lambert |
| 4,515,593 A | 5/1985 | Norton |
| 4,516,972 A | 5/1985 | Samson |
| 4,534,363 A | 8/1985 | Gold |
| 4,572,186 A | 2/1986 | Gould et al. |
| 4,580,568 A | 4/1986 | Gianturco |
| 4,634,432 A | 1/1987 | Kocak |
| 4,655,771 A | 4/1987 | Wallsten |
| 4,665,906 A | 5/1987 | Jervis |
| 4,665,918 A * | 5/1987 | Garza et al. .................. 606/108 |
| 4,705,511 A | 11/1987 | Kocak |
| 4,787,899 A | 11/1988 | Lazarus |
| 4,817,613 A | 4/1989 | Jaraczewski et al. |
| 4,990,151 A | 2/1991 | Wallsten et al. |
| 5,019,057 A | 5/1991 | Truckai |
| 5,041,126 A | 8/1991 | Gianturco |
| 5,057,092 A | 10/1991 | Webster, Jr. |
| 5,067,957 A | 11/1991 | Jervis |
| 5,104,399 A | 4/1992 | Lazarus |
| 5,158,543 A | 10/1992 | Lazarus |
| 5,176,660 A | 1/1993 | Truckai |
| 5,254,105 A | 10/1993 | Haaga |
| 5,282,824 A | 2/1994 | Gianturco |
| 5,290,295 A | 3/1994 | Querals et al. |
| 5,292,331 A | 3/1994 | Boneau |
| 5,324,306 A | 6/1994 | Makower et al. |
| 5,334,168 A | 8/1994 | Hemmer |
| 5,338,295 A | 8/1994 | Cornelius et al. |
| 5,342,384 A | 8/1994 | Sugarbaker |
| 5,358,493 A | 10/1994 | Schweich, Jr. et al. |
| 5,380,304 A | 1/1995 | Parker |
| 5,387,235 A | 2/1995 | Chuter |
| 5,397,345 A | 3/1995 | Lazarus |
| 5,405,377 A | 4/1995 | Cragg |
| 5,415,664 A | 5/1995 | Pinchuk |
| 5,433,723 A | 7/1995 | Lindenberg et al. |
| 5,456,713 A | 10/1995 | Chuter |
| 5,458,615 A | 10/1995 | Klemm et al. |
| 5,464,449 A | 11/1995 | Ryan et al. |
| 5,474,563 A | 12/1995 | Myler et al. |
| 5,480,423 A | 1/1996 | Ravenscroft et al. |
| 5,489,295 A | 2/1996 | Piplani et al. |
| 5,507,771 A | 4/1996 | Gianturco |
| 5,522,881 A | 6/1996 | Lentz |
| 5,522,882 A | 6/1996 | Gaterud et al. |
| 5,531,715 A | 7/1996 | Engelson et al. |
| 5,533,987 A | 7/1996 | Pray et al. |
| 5,534,007 A | 7/1996 | St. Germain et al. |
| 5,540,712 A | 7/1996 | Kleshinski et al. |
| 5,545,210 A | 8/1996 | Hess et al. |
| 5,562,726 A | 10/1996 | Chuter |
| 5,562,728 A | 10/1996 | Lazarus et al. |
| 5,569,218 A | 10/1996 | Berg |
| 5,575,816 A | 11/1996 | Rudnick et al. |
| 5,575,817 A | 11/1996 | Martin |
| 5,591,195 A | 1/1997 | Taheri et al. |
| 5,597,378 A | 1/1997 | Jervis |
| 5,607,442 A | 3/1997 | Fischell et al. |
| 5,609,625 A | 3/1997 | Piplani et al. |
| 5,609,627 A | 3/1997 | Goicoechea et al. |
| 5,613,974 A | 3/1997 | Andreas et al. |
| 5,618,270 A | 4/1997 | Orejola |
| 5,628,754 A | 5/1997 | Shevlin et al. |
| 5,628,783 A | 5/1997 | Quiachon et al. |
| 5,632,763 A | 5/1997 | Glastra |
| 5,639,278 A | 6/1997 | Dereume et al. |
| 5,658,263 A | 8/1997 | Dang et al. |
| 5,662,675 A | 9/1997 | Polanskyj Stockert et al. |
| 5,662,700 A | 9/1997 | Lazarus |
| 5,674,208 A | 10/1997 | Berg et al. |
| 5,676,696 A | 10/1997 | Marcade |
| 5,683,449 A | 11/1997 | Marcade |
| 5,693,086 A | 12/1997 | Goicoechea et al. |
| 5,700,269 A * | 12/1997 | Pinchuk et al. ............... 606/108 |
| 5,709,703 A | 1/1998 | Lukic et al. |
| 5,713,917 A | 2/1998 | Leonhardt et al. |
| 5,716,365 A | 2/1998 | Goicoechea et al. |
| 5,716,393 A | 2/1998 | Lindenberg et al. |
| 5,720,776 A | 2/1998 | Chuter et al. |
| 5,723,003 A | 3/1998 | Winston et al. |
| 5,730,733 A | 3/1998 | Mortier et al. |
| 5,733,267 A | 3/1998 | Del Toro |
| 5,735,859 A | 4/1998 | Fischell et al. |
| 5,755,778 A | 5/1998 | Kleshinski |
| 5,782,811 A | 7/1998 | Samson et al. |
| 5,782,904 A | 7/1998 | White et al. |
| 5,782,909 A | 7/1998 | Quiachon et al. |
| 5,788,707 A | 8/1998 | Del Toro et al. |
| 5,792,144 A | 8/1998 | Fischell et al. |
| 5,800,515 A | 9/1998 | Nadal et al. |
| 5,800,517 A | 9/1998 | Anderson et al. |
| 5,800,520 A | 9/1998 | Fogarty et al. |
| 5,824,036 A | 10/1998 | Lauterjung |
| 5,824,037 A | 10/1998 | Fogarty et al. |
| 5,824,039 A | 10/1998 | Piplani et al. |
| 5,824,040 A | 10/1998 | Cox et al. |
| 5,824,041 A | 10/1998 | Lenker et al. |
| 5,824,042 A | 10/1998 | Lombardi et al. |
| 5,824,044 A | 10/1998 | Quiachon et al. |
| 5,843,158 A | 12/1998 | Lenker et al. |
| 5,843,160 A | 12/1998 | Rhodes |
| 5,843,164 A | 12/1998 | Frantzen et al. |
| 5,843,167 A | 12/1998 | Dwyer et al. |
| 5,851,228 A | 12/1998 | Pinheiro |
| 5,860,998 A | 1/1999 | Robinson et al. |
| 5,871,536 A * | 2/1999 | Lazarus ....................... 623/1.13 |
| 5,891,110 A | 4/1999 | Larson et al. |
| 5,891,114 A | 4/1999 | Chien et al. |
| 5,893,868 A | 4/1999 | Hanson et al. |
| 5,899,892 A | 5/1999 | Mortier et al. |
| 5,902,334 A | 5/1999 | Dwyer et al. |
| 5,904,713 A | 5/1999 | Leschinsky |
| 5,906,619 A | 5/1999 | Olson et al. |
| 5,910,101 A | 6/1999 | Andrews et al. |
| 5,911,715 A | 6/1999 | Berg et al. |
| 5,916,263 A | 6/1999 | Goicoechea et al. |
| 5,938,696 A | 8/1999 | Goicoechea et al. |
| 5,944,726 A | 8/1999 | Blaeser et al. |
| 5,947,939 A | 9/1999 | Mortier et al. |
| 5,951,495 A | 9/1999 | Berg et al. |
| 5,954,651 A | 9/1999 | Berg et al. |
| 5,957,949 A | 9/1999 | Leonhardt et al. |
| 5,961,511 A | 10/1999 | Mortier et al. |
| 5,968,069 A | 10/1999 | Dusbabek et al. |
| 5,984,955 A | 11/1999 | Wisselink |
| 5,993,481 A | 11/1999 | Marcade et al. |
| 6,004,310 A | 12/1999 | Bardsley et al. |
| 6,004,328 A | 12/1999 | Solar |
| 6,004,347 A | 12/1999 | McNamara et al. |
| 6,019,778 A | 2/2000 | Wilson et al. |
| 6,024,763 A | 2/2000 | Lenker et al. |
| 6,039,749 A | 3/2000 | Marin et al. |
| 6,039,758 A | 3/2000 | Quiachon et al. |
| 6,039,759 A | 3/2000 | Carpentier et al. |
| 6,045,557 A | 4/2000 | White et al. |
| 6,051,020 A | 4/2000 | Goicoechea et al. |
| 6,053,943 A | 4/2000 | Edwin et al. |
| 6,063,112 A | 5/2000 | Sgro |
| 6,071,307 A | 6/2000 | Rhee et al. |
| 6,099,548 A | 8/2000 | Taheri |
| 6,099,558 A | 8/2000 | White et al. |
| 6,099,559 A | 8/2000 | Nolting |
| 6,110,191 A | 8/2000 | Dehdashtian et al. |
| 6,110,198 A | 8/2000 | Fogarty et al. |
| 6,117,167 A | 9/2000 | Goicoechea et al. |
| 6,120,480 A | 9/2000 | Zhang et al. |
| 6,123,723 A | 9/2000 | Konya et al. |
| 6,152,944 A | 11/2000 | Holman et al. |
| 6,165,163 A | 12/2000 | Chien et al. |
| 6,165,213 A | 12/2000 | Goicoechea et al. |

(56) References Cited

U.S. PATENT DOCUMENTS

| | | | |
|---|---|---|---|
| 6,168,616 B1 | 1/2001 | Brown, III | |
| 6,168,623 B1 | 1/2001 | Fogarty et al. | |
| 6,183,481 B1 | 2/2001 | Lee et al. | |
| 6,183,505 B1 | 2/2001 | Mohn, Jr. et al. | |
| 6,183,506 B1 | 2/2001 | Penn et al. | |
| 6,193,705 B1 | 2/2001 | Mortier et al. | |
| 6,200,336 B1 | 3/2001 | Pavcnik et al. | |
| 6,200,339 B1 | 3/2001 | Leschinsky et al. | |
| 6,203,550 B1 | 3/2001 | Olson | |
| 6,203,568 B1 | 3/2001 | Lombardi et al. | |
| 6,210,435 B1 | 4/2001 | Piplani et al. | |
| 6,212,422 B1 | 4/2001 | Berg et al. | |
| 6,213,976 B1 * | 4/2001 | Trerotola | 604/104 |
| 6,214,038 B1 | 4/2001 | Piplani et al. | |
| 6,221,079 B1 | 4/2001 | Magovern et al. | |
| 6,221,102 B1 | 4/2001 | Baker et al. | |
| 6,224,609 B1 | 5/2001 | Ressemann et al. | |
| 6,228,063 B1 | 5/2001 | Aboul-Hosn | |
| 6,231,601 B1 | 5/2001 | Myers et al. | |
| 6,238,430 B1 * | 5/2001 | Klumb et al. | 623/1.11 |
| 6,245,052 B1 | 6/2001 | Orth et al. | |
| 6,248,112 B1 | 6/2001 | Gambale et al. | |
| 6,248,116 B1 | 6/2001 | Chevillon et al. | |
| 6,251,132 B1 | 6/2001 | Ravenscroft et al. | |
| 6,254,609 B1 | 7/2001 | Vrba et al. | |
| 6,267,775 B1 | 7/2001 | Clerc et al. | |
| 6,273,909 B1 | 8/2001 | Kugler et al. | |
| 6,280,466 B1 | 8/2001 | Kugler et al. | |
| 6,280,467 B1 | 8/2001 | Leonhardt | |
| 6,287,315 B1 | 9/2001 | Wijeratne et al. | |
| 6,302,906 B1 | 10/2001 | Goicoechea et al. | |
| 6,302,907 B1 | 10/2001 | Hijlkema | |
| 6,306,141 B1 | 10/2001 | Jervis | |
| 6,312,458 B1 | 11/2001 | Golds | |
| 6,319,275 B1 | 11/2001 | Lashinski et al. | |
| 6,319,278 B1 | 11/2001 | Quinn | |
| 6,334,869 B1 * | 1/2002 | Leonhardt et al. | 623/1.13 |
| 6,338,709 B1 | 1/2002 | Geoffrion et al. | |
| 6,342,066 B1 | 1/2002 | Toro et al. | |
| 6,344,044 B1 | 2/2002 | Fulkerson | |
| 6,344,052 B1 | 2/2002 | Greenan et al. | |
| 6,346,118 B1 * | 2/2002 | Baker et al. | 623/1.12 |
| 6,350,278 B1 | 2/2002 | Lenker et al. | |
| 6,355,056 B1 | 3/2002 | Pinheiro | |
| 6,355,060 B1 | 3/2002 | Lenker et al. | |
| 6,368,345 B1 | 4/2002 | Dehdashtian et al. | |
| 6,375,675 B2 | 4/2002 | Dehdashtian et al. | |
| 6,375,676 B1 | 4/2002 | Cox | |
| 6,379,372 B1 | 4/2002 | Dehdashtian et al. | |
| 6,389,946 B1 | 5/2002 | Frid et al. | |
| 6,395,017 B1 | 5/2002 | Dwyer et al. | |
| 6,395,022 B1 | 5/2002 | Piplani et al. | |
| 6,402,781 B1 | 6/2002 | Langberg et al. | |
| 6,416,542 B1 | 7/2002 | Marcade et al. | |
| 6,419,686 B1 | 7/2002 | McLeod et al. | |
| 6,425,898 B1 | 7/2002 | Wilson et al. | |
| 6,443,979 B1 | 9/2002 | Stalker et al. | |
| 6,443,980 B1 | 9/2002 | Wang et al. | |
| 6,450,988 B1 | 9/2002 | Bradshaw | |
| 6,451,053 B1 | 9/2002 | Dehdashtian et al. | |
| 6,454,796 B1 | 9/2002 | Barkman et al. | |
| 6,458,867 B1 | 10/2002 | Wang et al. | |
| 6,464,684 B1 | 10/2002 | Galdonik | |
| 6,464,719 B2 | 10/2002 | Jayaraman | |
| 6,464,721 B1 | 10/2002 | Marcade et al. | |
| 6,478,818 B1 | 11/2002 | Taheri | |
| 6,488,700 B2 | 12/2002 | Klumb et al. | |
| 6,503,274 B1 | 1/2003 | Howanec, Jr. et al. | |
| 6,505,066 B2 | 1/2003 | Berg et al. | |
| 6,517,571 B1 | 2/2003 | Brauker et al. | |
| 6,517,572 B2 | 2/2003 | Kugler et al. | |
| 6,517,573 B1 | 2/2003 | Pollock et al. | |
| 6,520,986 B2 | 2/2003 | Martin et al. | |
| 6,524,335 B1 | 2/2003 | Hartley et al. | |
| 6,524,336 B1 | 2/2003 | Papazolgou et al. | |
| 6,533,753 B1 | 3/2003 | Haarstad et al. | |
| 6,540,698 B1 | 4/2003 | Ishii | |
| 6,540,778 B1 | 4/2003 | Quiachon et al. | |
| 6,551,350 B1 | 4/2003 | Thornton et al. | |
| 6,562,022 B2 | 5/2003 | Hoste et al. | |
| 6,565,596 B1 | 5/2003 | White et al. | |
| 6,565,597 B1 | 5/2003 | Fearnot et al. | |
| 6,575,994 B1 | 6/2003 | Marin et al. | |
| 6,576,007 B2 | 6/2003 | Dehdashtian et al. | |
| 6,582,458 B1 | 6/2003 | White et al. | |
| 6,582,460 B1 | 6/2003 | Cryer | |
| 6,592,526 B1 | 7/2003 | Lenker | |
| 6,613,073 B1 | 9/2003 | White et al. | |
| 6,616,626 B2 | 9/2003 | Crank et al. | |
| 6,620,126 B2 | 9/2003 | Unsworth et al. | |
| 6,641,606 B2 | 11/2003 | Ouriel et al. | |
| 6,652,571 B1 | 11/2003 | White et al. | |
| 6,652,572 B2 | 11/2003 | Kugler et al. | |
| 6,660,033 B1 | 12/2003 | Marcade et al. | |
| 6,676,666 B2 | 1/2004 | Vrba et al. | |
| 6,682,536 B2 | 1/2004 | Vardi et al. | |
| 6,682,537 B2 | 1/2004 | Ouriel et al. | |
| 6,682,557 B1 | 1/2004 | Quiachon et al. | |
| 6,685,736 B1 | 2/2004 | White et al. | |
| 6,689,152 B2 | 2/2004 | Balceta et al. | |
| 6,689,158 B1 | 2/2004 | White et al. | |
| 6,692,458 B2 | 2/2004 | Forman et al. | |
| 6,692,483 B2 | 2/2004 | Vardi et al. | |
| 6,692,512 B2 | 2/2004 | Jang | |
| 6,695,875 B2 | 2/2004 | Stelter et al. | |
| 6,706,033 B1 | 3/2004 | Martinez et al. | |
| 6,726,712 B1 | 4/2004 | Raeder-Devens et al. | |
| 6,733,519 B2 | 5/2004 | Lashinski et al. | |
| 6,733,523 B2 | 5/2004 | Shaolian et al. | |
| 6,755,856 B2 | 6/2004 | Fierens et al. | |
| 6,761,731 B2 | 7/2004 | Majercak | |
| 6,790,222 B2 | 9/2004 | Kugler et al. | |
| 6,802,860 B2 | 10/2004 | Cosgrove et al. | |
| 6,808,529 B2 * | 10/2004 | Fulkerson | 606/108 |
| 6,811,559 B2 | 11/2004 | Thornton | |
| 6,814,748 B1 | 11/2004 | Baker et al. | |
| 6,821,291 B2 | 11/2004 | Bolea et al. | |
| 6,827,710 B1 | 12/2004 | Mooney et al. | |
| 6,827,711 B2 | 12/2004 | Sunseri | |
| 6,843,803 B2 | 1/2005 | Ryan et al. | |
| 6,849,084 B2 | 2/2005 | Rabkin et al. | |
| 6,849,088 B2 | 2/2005 | Dehdashtian et al. | |
| 6,858,034 B2 | 2/2005 | Hijlkema et al. | |
| 6,859,986 B2 | 3/2005 | Jackson et al. | |
| 6,860,901 B1 | 3/2005 | Baker et al. | |
| 6,863,668 B2 | 3/2005 | Gillespie et al. | |
| 6,866,660 B2 | 3/2005 | Garabedian et al. | |
| 6,884,260 B2 | 4/2005 | Kugler et al. | |
| 6,890,348 B2 | 5/2005 | Sydney et al. | |
| 6,911,039 B2 | 6/2005 | Shiu et al. | |
| 6,916,335 B2 | 7/2005 | Kanji | |
| 6,918,925 B2 | 7/2005 | Tehrani | |
| 6,932,829 B2 | 8/2005 | Majercak | |
| 6,938,646 B2 | 9/2005 | Litton | |
| 6,939,371 B2 | 9/2005 | Kugler et al. | |
| 6,945,989 B1 | 9/2005 | Betelia et al. | |
| 6,945,990 B2 * | 9/2005 | Greenan | 623/1.12 |
| 6,964,679 B1 | 11/2005 | Marcade et al. | |
| 6,989,024 B2 | 1/2006 | Hebert et al. | |
| 6,994,722 B2 | 2/2006 | DiCarlo | |
| 7,001,420 B2 | 2/2006 | Speck et al. | |
| 7,011,647 B2 | 3/2006 | Purdy et al. | |
| 7,014,653 B2 | 3/2006 | Ouriel et al. | |
| 7,070,582 B2 | 7/2006 | Freyman et al. | |
| 7,112,217 B1 | 9/2006 | Kugler et al. | |
| 7,115,134 B2 | 10/2006 | Chambers | |
| 7,125,419 B2 | 10/2006 | Sequin et al. | |
| 7,147,660 B2 | 12/2006 | Chobotov et al. | |
| 7,160,318 B2 | 1/2007 | Greenberg et al. | |
| 7,163,552 B2 | 1/2007 | Diaz | |
| 7,166,125 B1 | 1/2007 | Baker et al. | |
| 7,169,170 B2 | 1/2007 | Widenhouse | |
| 7,195,639 B2 | 3/2007 | Quiachon et al. | |
| 7,225,518 B2 | 6/2007 | Eidenschink et al. | |

(56) References Cited

U.S. PATENT DOCUMENTS

| | | |
|---|---|---|
| 7,238,197 B2 | 7/2007 | Sequin et al. |
| 7,264,632 B2 | 9/2007 | Wright et al. |
| 7,294,147 B2 | 11/2007 | Hartley |
| 7,351,256 B2 | 4/2008 | Hojeibane et al. |
| 7,708,771 B2 | 5/2010 | Chuter et al. |
| 7,717,950 B2 | 5/2010 | Greenan |
| 7,722,663 B1 | 5/2010 | Austin |
| 7,763,063 B2 | 7/2010 | Arbefeuille et al. |
| 8,043,354 B2 | 10/2011 | Greenberg et al. |
| 8,062,345 B2 | 11/2011 | Ouellette et al. |
| 8,062,349 B2 | 11/2011 | Moore et al. |
| 8,070,790 B2 | 12/2011 | Berra et al. |
| 8,292,943 B2 | 10/2012 | Berra et al. |
| 8,308,790 B2 | 11/2012 | Arbefeuille et al. |
| 8,449,595 B2 | 5/2013 | Ouellette et al. |
| 2001/0000801 A1 | 5/2001 | Miller et al. |
| 2001/0001833 A1 | 5/2001 | Ravenscroft et al. |
| 2001/0034549 A1 | 10/2001 | Bartholf et al. |
| 2001/0049547 A1 | 12/2001 | Moore |
| 2002/0007193 A1 | 1/2002 | Tanner et al. |
| 2002/0016597 A1 | 2/2002 | Dwyer et al. |
| 2002/0016627 A1 | 2/2002 | Golds |
| 2002/0035394 A1 | 3/2002 | Fierens |
| 2002/0045929 A1 | 4/2002 | Diaz |
| 2002/0052660 A1 | 5/2002 | Greenhalgh |
| 2002/0082523 A1* | 6/2002 | Kinsella et al. ............... 600/585 |
| 2002/0082674 A1 | 6/2002 | Anson et al. |
| 2002/0091439 A1 | 7/2002 | Baker et al. |
| 2002/0095140 A1 | 7/2002 | Lootz et al. |
| 2002/0107561 A1 | 8/2002 | Pinheiro |
| 2002/0108621 A1 | 8/2002 | Berg et al. |
| 2002/0138133 A1 | 9/2002 | Lenz et al. |
| 2002/0156518 A1 | 10/2002 | Tehrani |
| 2002/0156522 A1 | 10/2002 | Ivancev et al. |
| 2002/0161424 A1 | 10/2002 | Rapacki et al. |
| 2002/0188344 A1 | 12/2002 | Bolea et al. |
| 2002/0198587 A1 | 12/2002 | Greenberg et al. |
| 2003/0028237 A1 | 2/2003 | Sullivan et al. |
| 2003/0074049 A1 | 4/2003 | Hoganson et al. |
| 2003/0083734 A1 | 5/2003 | Friedrich et al. |
| 2003/0088305 A1 | 5/2003 | Van Schie et al. |
| 2003/0135269 A1 | 7/2003 | Swanstrom |
| 2003/0139803 A1 | 7/2003 | Sequin et al. |
| 2003/0163193 A1 | 8/2003 | Widenhouse |
| 2003/0176911 A1 | 9/2003 | Iancea et al. |
| 2003/0212431 A1 | 11/2003 | Brady et al. |
| 2003/0220682 A1 | 11/2003 | Kujawski |
| 2003/0236565 A1 | 12/2003 | DiMatteo et al. |
| 2004/0073284 A1 | 4/2004 | Bates et al. |
| 2004/0073289 A1 | 4/2004 | Hartley |
| 2004/0093063 A1* | 5/2004 | Wright et al. ............... 623/1.12 |
| 2004/0098084 A1 | 5/2004 | Hartley et al. |
| 2004/0117003 A1 | 6/2004 | Ouriel et al. |
| 2004/0148007 A1 | 7/2004 | Jackson et al. |
| 2004/0148009 A1 | 7/2004 | Buzzard et al. |
| 2004/0193141 A1 | 9/2004 | Leopold et al. |
| 2004/0193244 A1 | 9/2004 | Hartley et al. |
| 2004/0193252 A1 | 9/2004 | Perez et al. |
| 2004/0199240 A1 | 10/2004 | Dorn |
| 2004/0230286 A1 | 11/2004 | Moore et al. |
| 2004/0236403 A1 | 11/2004 | Leonhardt et al. |
| 2004/0236407 A1 | 11/2004 | Fierens et al. |
| 2004/0267281 A1 | 12/2004 | Harari et al. |
| 2005/0033406 A1 | 2/2005 | Barnhart et al. |
| 2005/0038495 A1 | 2/2005 | Greenan |
| 2005/0049667 A1 | 3/2005 | Arbefeuille et al. |
| 2005/0049674 A1 | 3/2005 | Berra et al. |
| 2005/0080476 A1 | 4/2005 | Gunderson et al. |
| 2005/0080477 A1 | 4/2005 | Sydney et al. |
| 2005/0096726 A1 | 5/2005 | Sequin et al. |
| 2005/0107862 A1 | 5/2005 | Ohlenschlaeger |
| 2005/0149166 A1 | 7/2005 | Schaeffer et al. |
| 2005/0159803 A1 | 7/2005 | Lad et al. |
| 2005/0159804 A1 | 7/2005 | Lad et al. |
| 2005/0171597 A1 | 8/2005 | Boatman et al. |
| 2005/0171598 A1 | 8/2005 | Schaeffer |
| 2005/0177222 A1 | 8/2005 | Mead |
| 2005/0183259 A1 | 8/2005 | Eidenschink et al. |
| 2005/0192659 A1 | 9/2005 | Dahl et al. |
| 2005/0222668 A1 | 10/2005 | Schaeffer et al. |
| 2005/0283223 A1 | 12/2005 | Greeman |
| 2006/0020319 A1 | 1/2006 | Kim et al. |
| 2006/0020320 A1 | 1/2006 | Shaolian et al. |
| 2006/0058864 A1 | 3/2006 | Schaeffer et al. |
| 2006/0127439 A1 | 6/2006 | Mattes et al. |
| 2006/0129169 A1 | 6/2006 | Fogarty et al. |
| 2006/0129224 A1 | 6/2006 | Arbefeuille et al. |
| 2006/0135961 A1 | 6/2006 | Rosenman et al. |
| 2006/0178726 A1 | 8/2006 | Douglas |
| 2006/0178733 A1 | 8/2006 | Pinchuk et al. |
| 2006/0188408 A1 | 8/2006 | Arbefeuille et al. |
| 2006/0200110 A1 | 9/2006 | Lentz et al. |
| 2006/0212105 A1 | 9/2006 | Dorn et al. |
| 2006/0265047 A1 | 11/2006 | Dorn |
| 2007/0048348 A1 | 3/2007 | Atanasoska et al. |
| 2007/0053952 A1 | 3/2007 | Chen et al. |
| 2007/0055338 A1 | 3/2007 | Dorn |
| 2007/0055340 A1 | 3/2007 | Pryor |
| 2007/0055341 A1 | 3/2007 | Edoga et al. |
| 2007/0055345 A1 | 3/2007 | Arbefeuille |
| 2007/0055347 A1 | 3/2007 | Arbefeuille |
| 2007/0083252 A1 | 4/2007 | McDonald |
| 2007/0100422 A1 | 5/2007 | Shumer et al. |
| 2007/0100425 A1 | 5/2007 | Sequin et al. |
| 2007/0123972 A1 | 5/2007 | Greenberg et al. |
| 2007/0135818 A1 | 6/2007 | Moore et al. |
| 2007/0135889 A1 | 6/2007 | Moore et al. |
| 2007/0142894 A1 | 6/2007 | Moore et al. |
| 2007/0156228 A1 | 7/2007 | Majercak et al. |
| 2007/0162109 A1 | 7/2007 | Davila et al. |
| 2007/0163668 A1 | 7/2007 | Arbefeuille et al. |
| 2007/0173929 A1 | 7/2007 | Boucher et al. |
| 2007/0179592 A1 | 8/2007 | Schaeffer |
| 2007/0179593 A1 | 8/2007 | Fierens et al. |
| 2007/0179601 A1 | 8/2007 | Fierens et al. |
| 2007/0198078 A1 | 8/2007 | Berra et al. |
| 2007/0203566 A1 | 8/2007 | Arbefeuille et al. |
| 2007/0207186 A1 | 9/2007 | Scanlon et al. |
| 2007/0213800 A1 | 9/2007 | Fierens et al. |
| 2007/0219620 A1 | 9/2007 | Eells et al. |
| 2007/0244545 A1 | 10/2007 | Birdsall et al. |
| 2008/0021538 A1 | 1/2008 | Wright et al. |
| 2008/0046065 A1 | 2/2008 | Hartley et al. |
| 2008/0071343 A1 | 3/2008 | Mayberry et al. |
| 2008/0077226 A1 | 3/2008 | Ouellette et al. |
| 2008/0077227 A1 | 3/2008 | Ouellette et al. |
| 2008/0114441 A1 | 5/2008 | Rust et al. |
| 2008/0132996 A1 | 6/2008 | Drasler et al. |
| 2008/0172122 A1 | 7/2008 | Mayberry et al. |
| 2008/0195191 A1 | 8/2008 | Luo et al. |
| 2008/0264102 A1 | 10/2008 | Berra |
| 2010/0030255 A1 | 2/2010 | Berra et al. |
| 2010/0030318 A1 | 2/2010 | Berra |
| 2010/0234932 A1 | 9/2010 | Arbefeuille et al. |
| 2010/0274340 A1 | 10/2010 | Hartley et al. |
| 2011/0208288 A1 | 8/2011 | Arbefeuille et al. |
| 2011/0218607 A1 | 9/2011 | Arbefeuille et al. |
| 2011/0313503 A1 | 12/2011 | Berra et al. |
| 2012/0296413 A1 | 11/2012 | Arbefeuille et al. |

FOREIGN PATENT DOCUMENTS

| | | | |
|---|---|---|---|
| DE | 10 2006 053748 | B3 | 4/2008 |
| EP | 0 873 733 | A1 | 10/1998 |
| EP | 0 960 607 | A1 | 12/1999 |
| EP | 0 696 447 | B1 | 1/2000 |
| EP | 0 990 426 | A1 | 4/2000 |
| EP | 1 177 779 | A2 | 2/2002 |
| EP | 1 302 178 | A2 | 4/2003 |
| EP | 1 358 903 | A2 | 11/2003 |
| EP | 1 369 098 | A1 | 12/2003 |
| EP | 1 522 277 | A2 | 4/2005 |
| EP | 1 772 120 | A2 | 4/2007 |
| EP | 1 923 024 | A2 | 5/2008 |

(56) References Cited

FOREIGN PATENT DOCUMENTS

| | | |
|---|---|---|
| EP | 1 440 673 B1 | 9/2008 |
| EP | 1 982 677 A2 | 10/2008 |
| EP | 1 508 313 B1 | 12/2008 |
| FR | 2 714 816 | 7/1995 |
| FR | 2 722 678 | 1/1996 |
| FR | 2 779 939 A1 | 12/1999 |
| WO | WO 95/23008 | 8/1995 |
| WO | WO 96/09013 | 3/1996 |
| WO | WO 96/23455 | 8/1996 |
| WO | WO 96/31174 | 10/1996 |
| WO | WO 96/38101 | 12/1996 |
| WO | WO 97/33532 | 9/1997 |
| WO | WO 98/20811 | 5/1998 |
| WO | WO 98/23242 | 6/1998 |
| WO | WO 98/42276 | 10/1998 |
| WO | WO 99/25273 | 5/1999 |
| WO | WO 99/37242 | 7/1999 |
| WO | WO 99/65420 | 12/1999 |
| WO | WO 00/02615 | 1/2000 |
| WO | WO 00/30562 | 6/2000 |
| WO | WO 01/17602 A1 | 3/2001 |
| WO | WO 01/21102 A1 | 3/2001 |
| WO | WO 03/015662 | 2/2003 |
| WO | WO 2004/002370 A1 | 1/2004 |
| WO | WO 2004/071352 A1 | 8/2004 |
| WO | WO 2005/023149 A2 | 3/2005 |
| WO | WO 2005/034808 A1 | 4/2005 |
| WO | WO 2005/067819 A1 | 7/2005 |
| WO | WO 2005/081936 A2 | 9/2005 |
| WO | WO 2005/112821 A2 | 12/2005 |
| WO | WO 2007/008533 A1 | 1/2007 |
| WO | WO 2007/092276 A2 | 8/2007 |
| WO | WO 2008/031103 A2 | 3/2008 |
| WO | WO 2008/098252 A2 | 8/2008 |
| WO | WO 2009/023221 A1 | 2/2009 |
| WO | WO 2009/124124 A1 | 10/2009 |
| WO | WO 2010/005524 A2 | 1/2010 |
| WO | WO 2010/105195 A2 | 9/2010 |
| WO | WO 2011/056638 A1 | 5/2011 |

OTHER PUBLICATIONS

Notification of Transmittal of the International Preliminary Report on Patentability for International Application No. PCT/US04/28530, mailed Jul. 26, 2006.
U.S. Office Action dated Jul. 9, 2010 for U.S. Appl. No. 11/700,510.
U.S. Office Action dated Jan. 12, 2010 for U.S. Appl. No. 11/828,675.
U.S. Office Action dated Oct. 14, 2010 for U.S. Appl. No. 11/828,675.
U.S. Office Action dated Dec. 8, 2010 for U.S. Appl. No. 11/700,510.
Notice of Allowance dated Jun. 7, 2011 for U.S. Appl. No. 11/700,510.
Notice of Allowance dated Jun. 23, 2011 for U.S. Appl. No. 11/828,675.
Notice of Allowance, Date Mailed: Oct. 3, 2011, U.S. Appl. No. 11/700,510.
Notice of Allowance, Date Mailed: Oct. 7, 2011, U.S. Appl. No. 11/828,675.
Office Action from U.S. Appl. No. 13/024,882, Dated: Nov. 27, 2012.
Office Action from U.S. Appl. No. 13/566,412, Dated: Dec. 5, 2012.

* cited by examiner

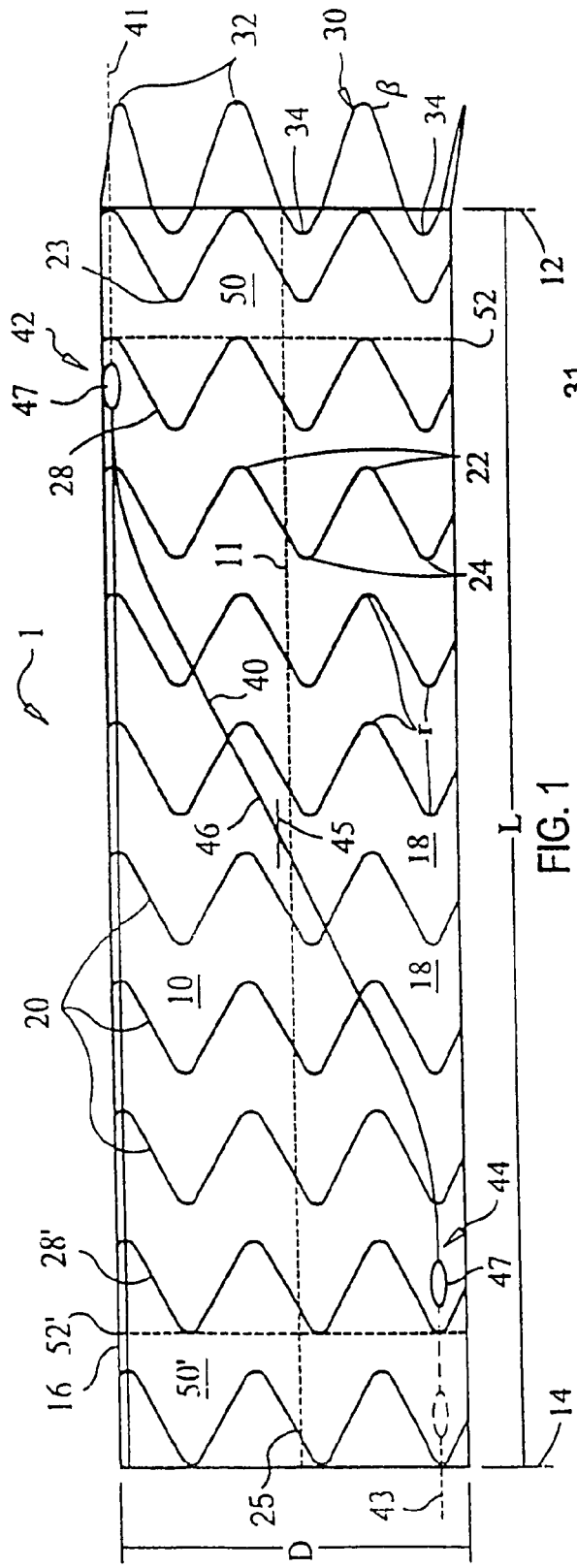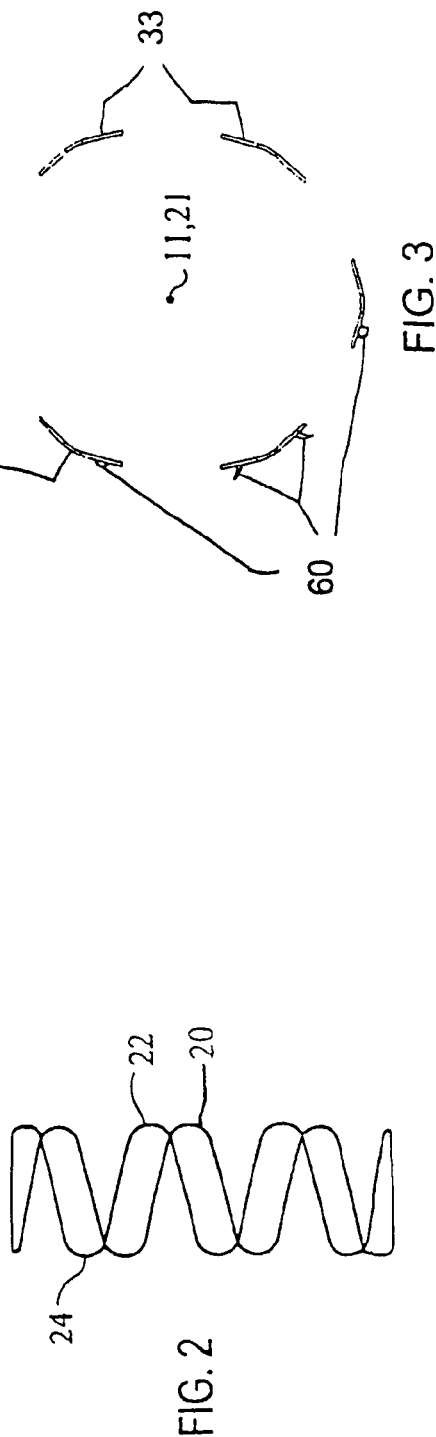

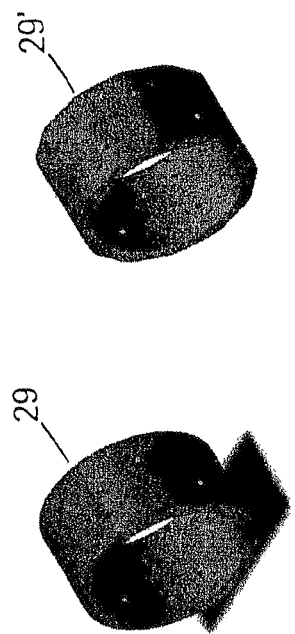
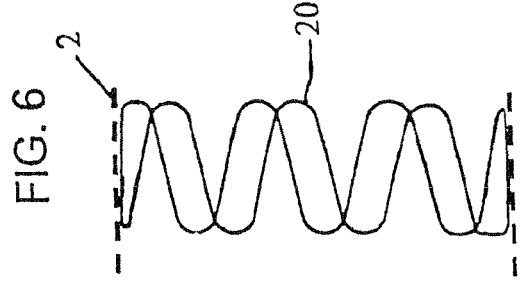
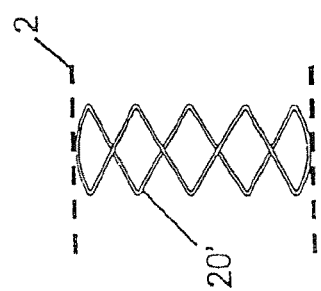
FIG. 4
PRIOR ART
FIG. 5
PRIOR ART
FIG. 6
FIG. 7

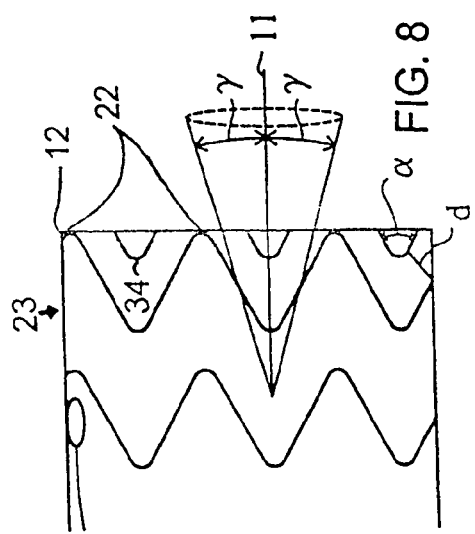
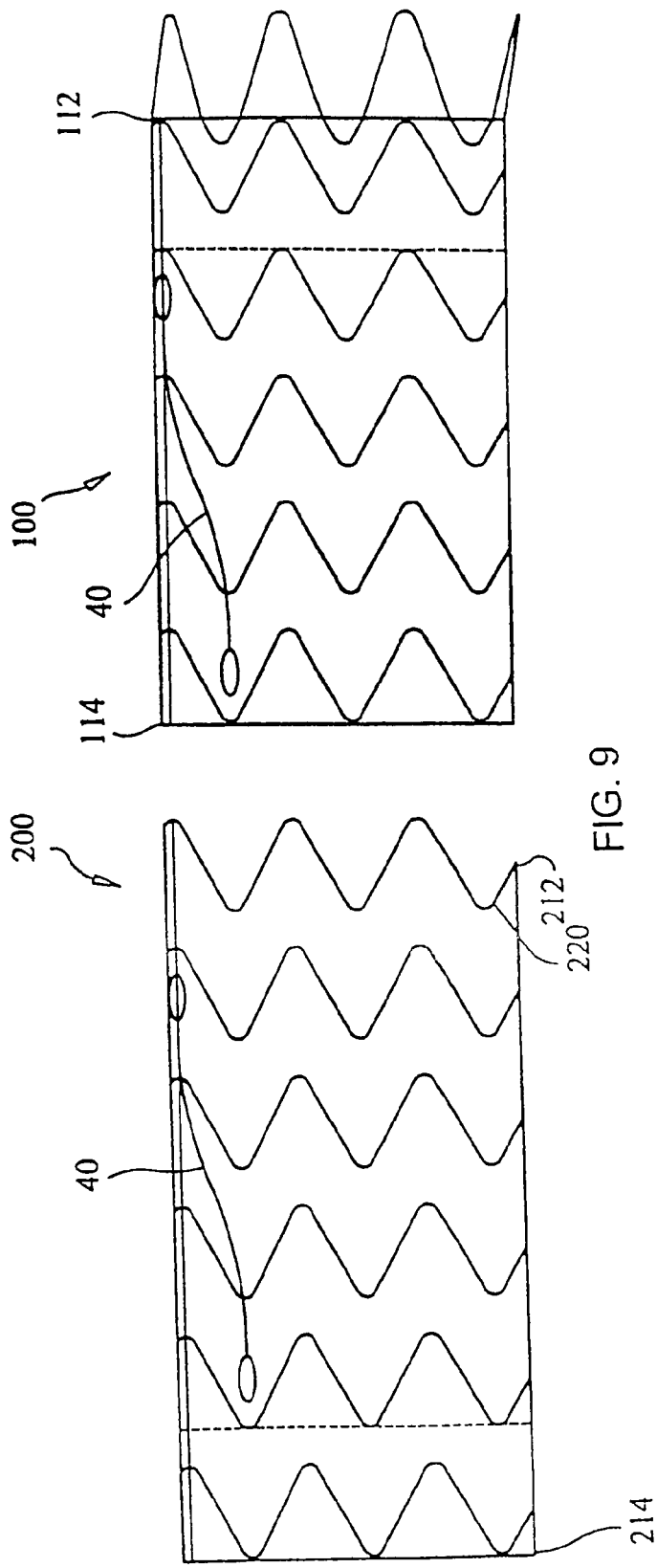
FIG. 8
FIG. 9

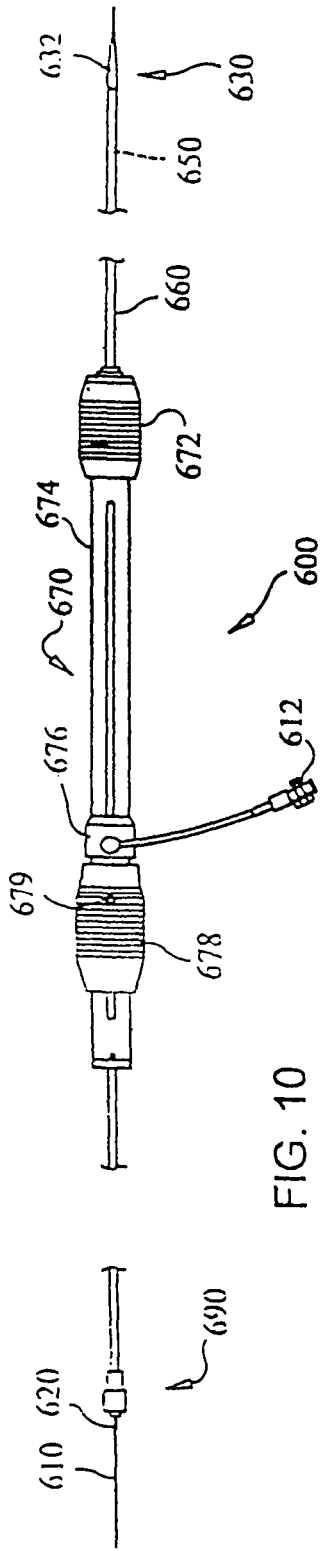
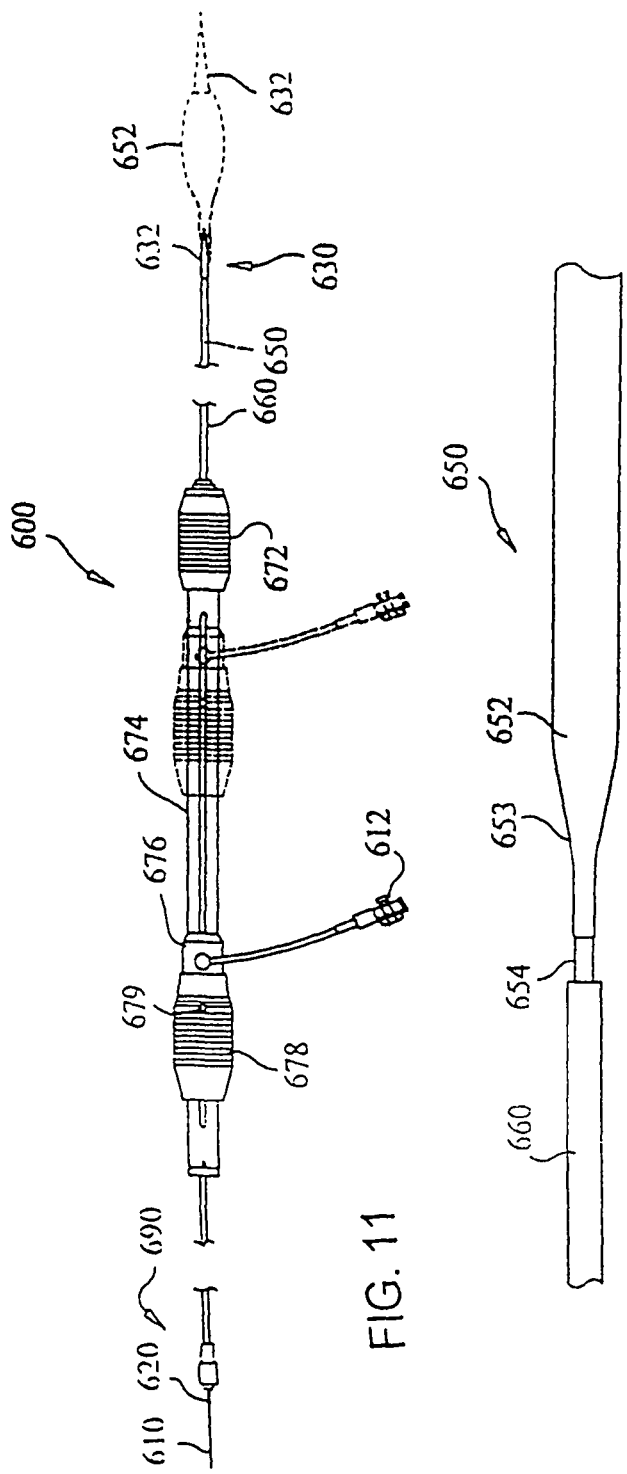
FIG. 10
FIG. 11
FIG. 12

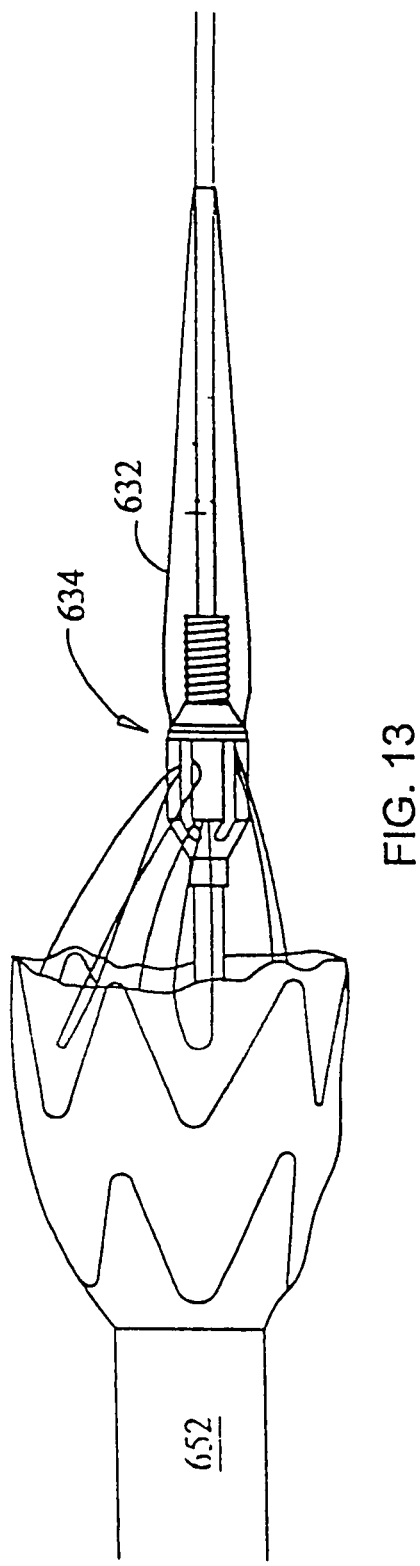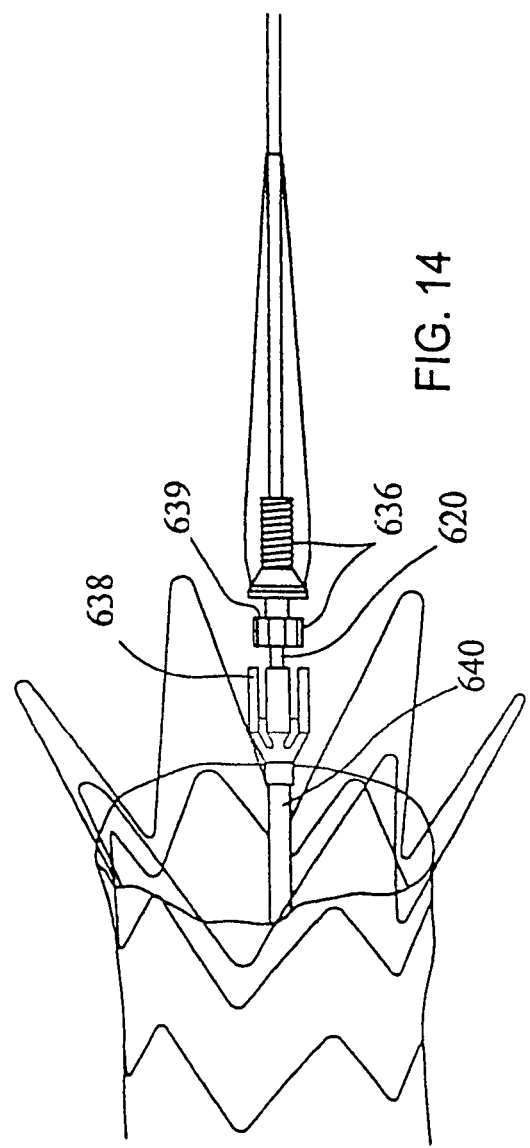

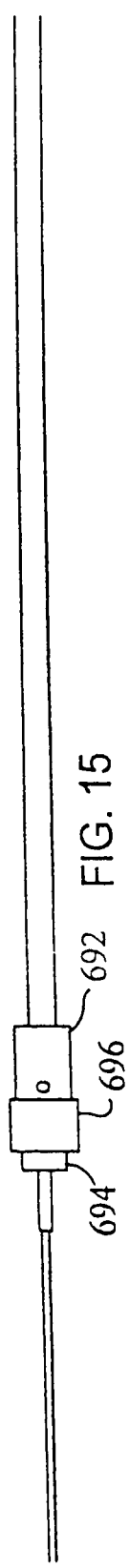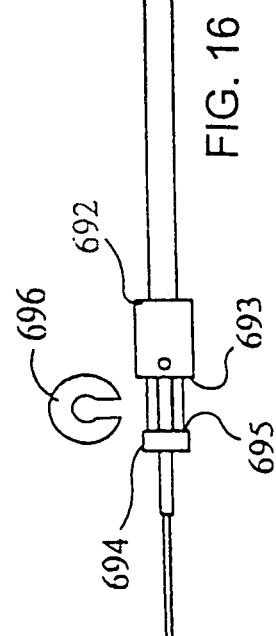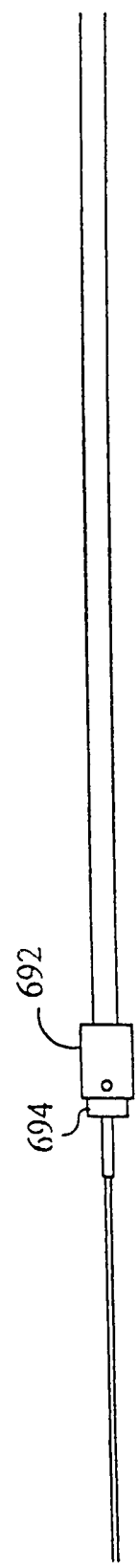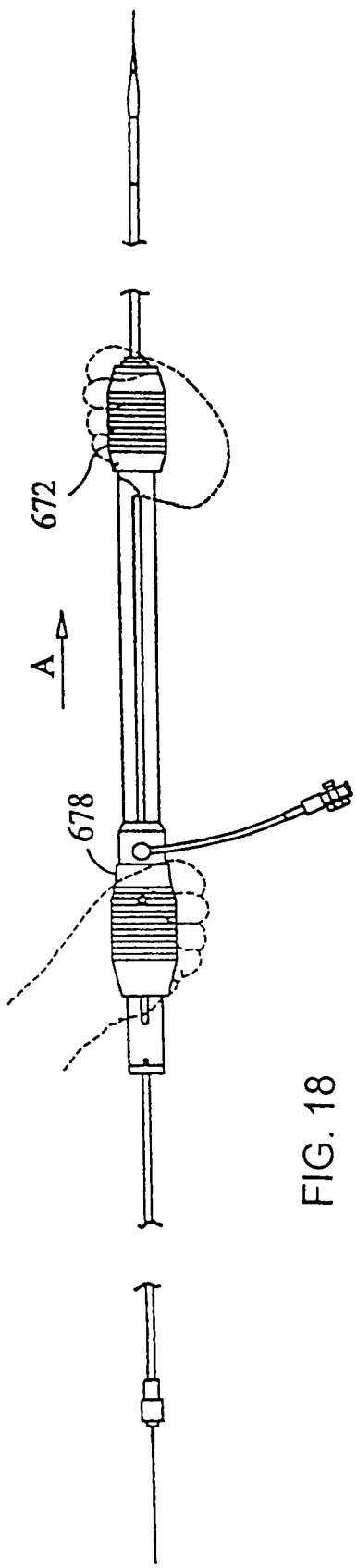
FIG. 15
FIG. 16
FIG. 17
FIG. 18

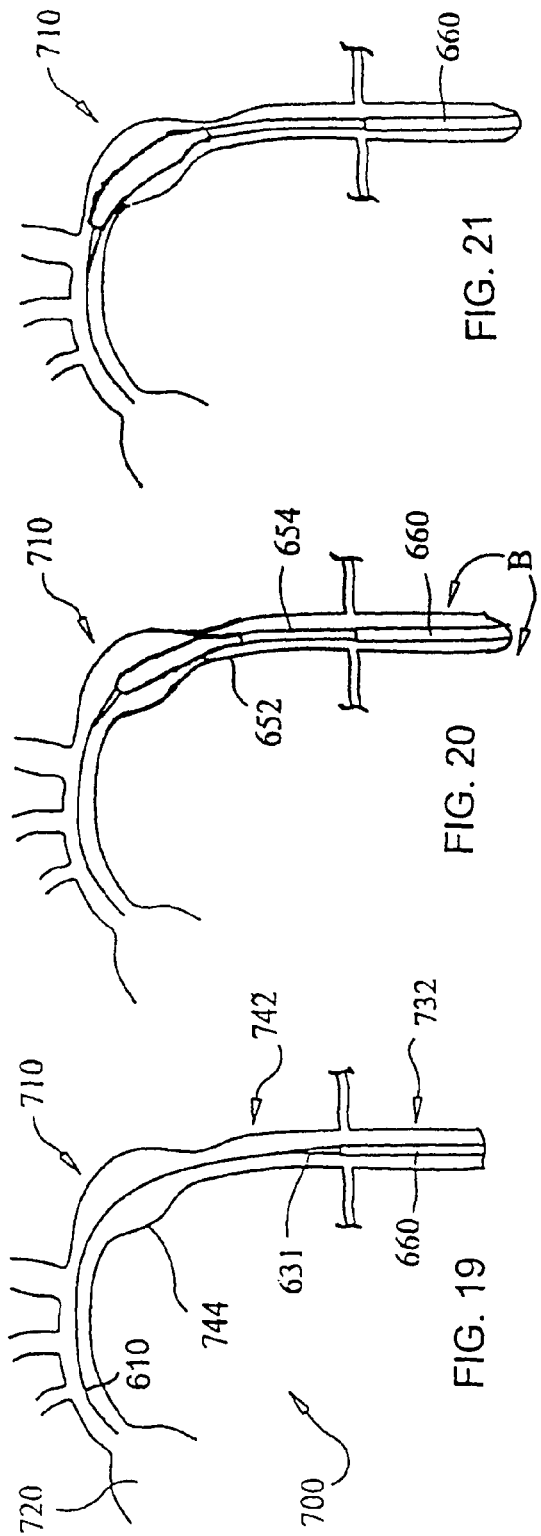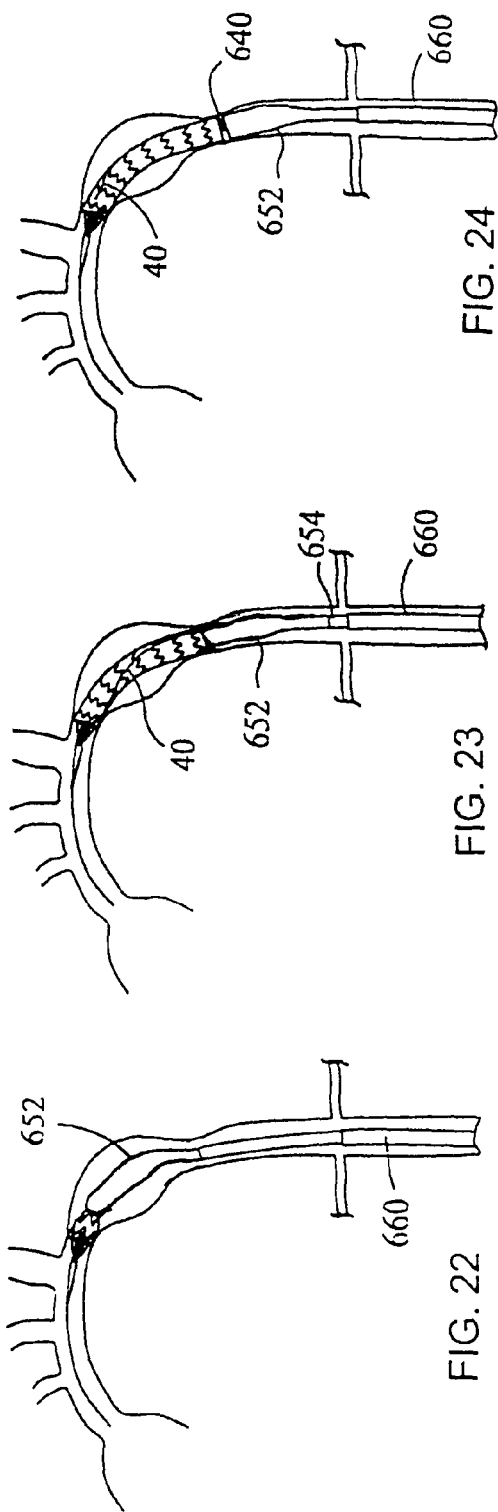

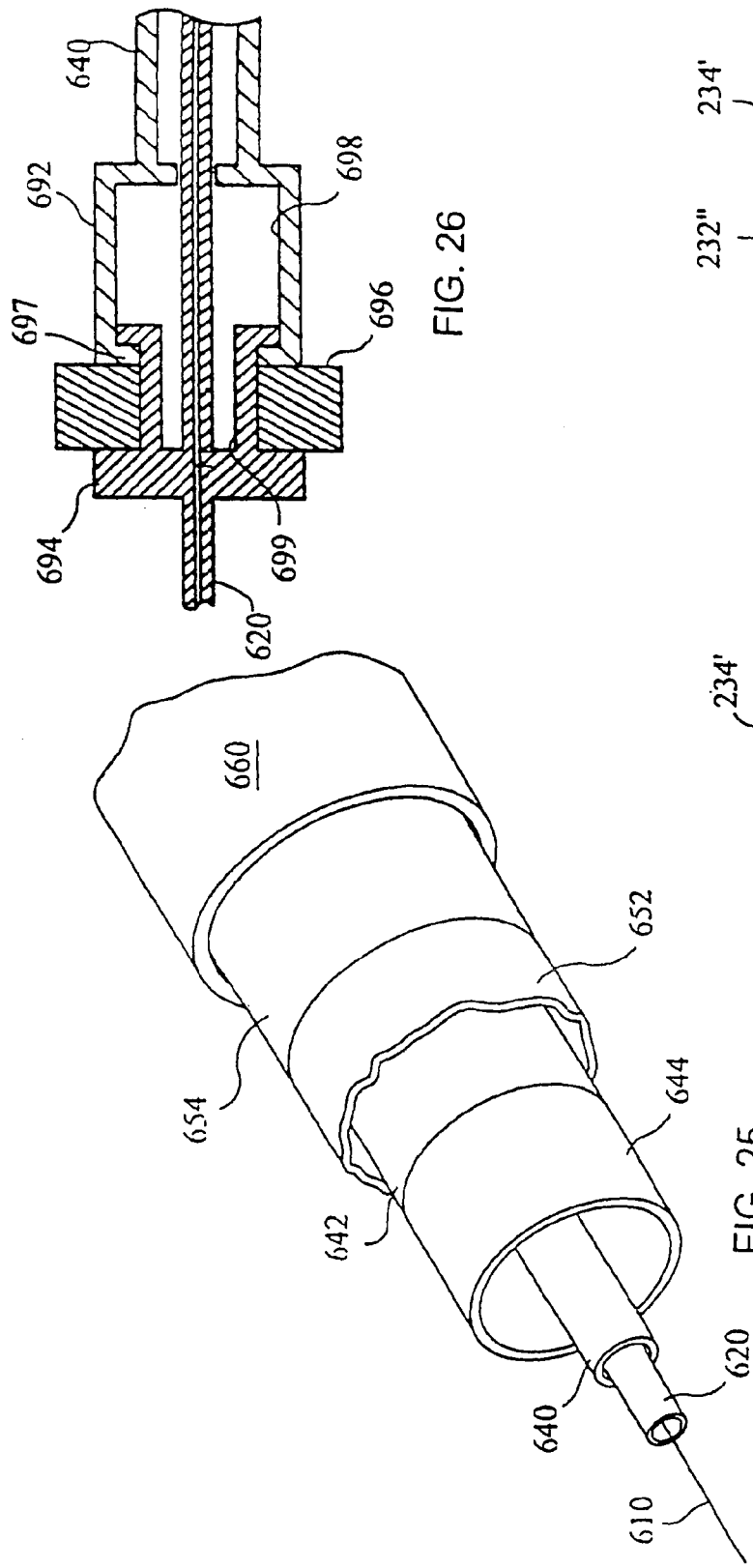

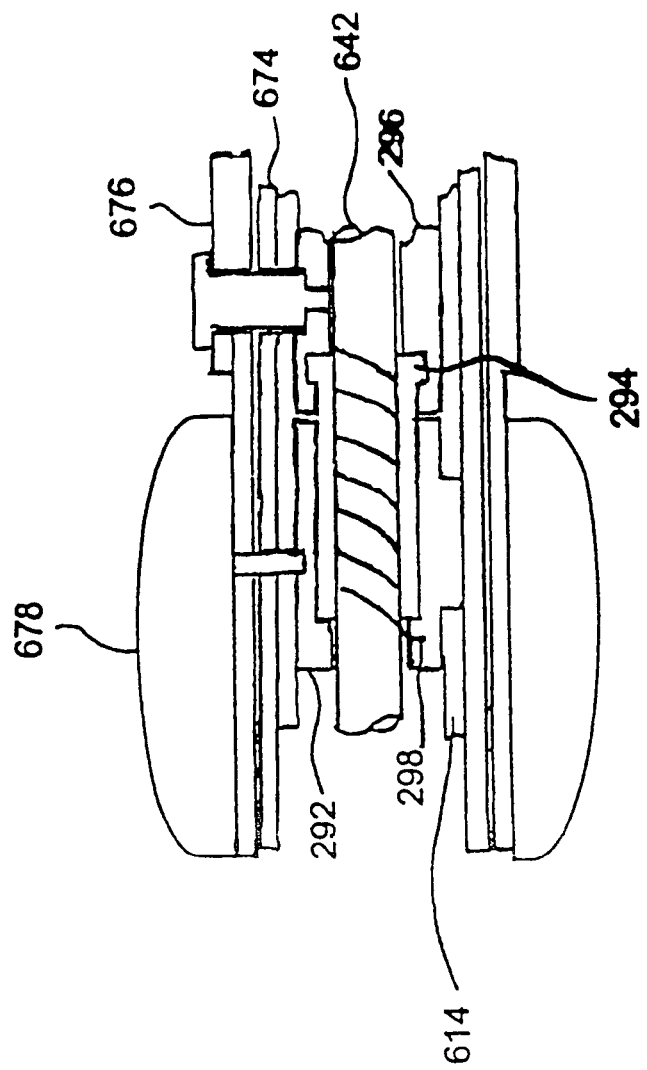

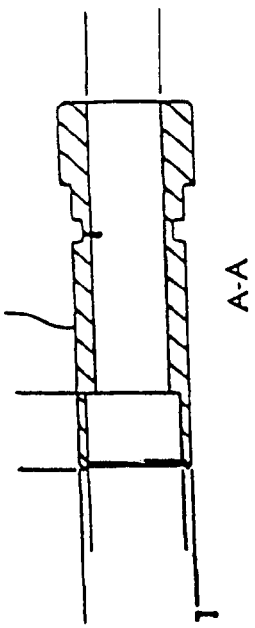
FIG. 42
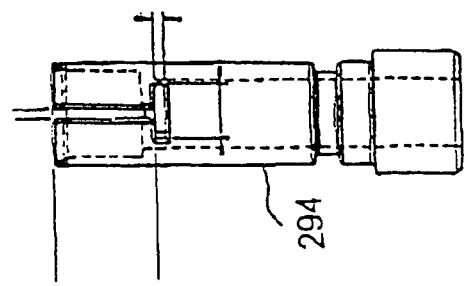
FIG. 43
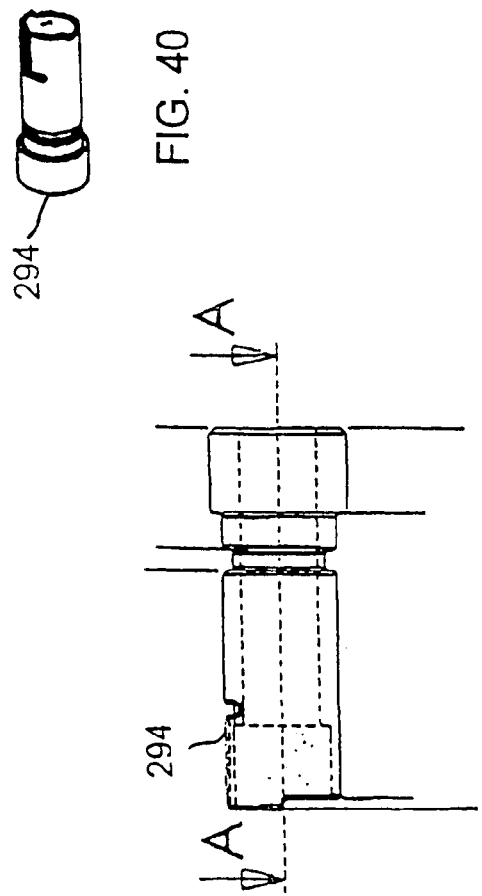
FIG. 40
FIG. 41

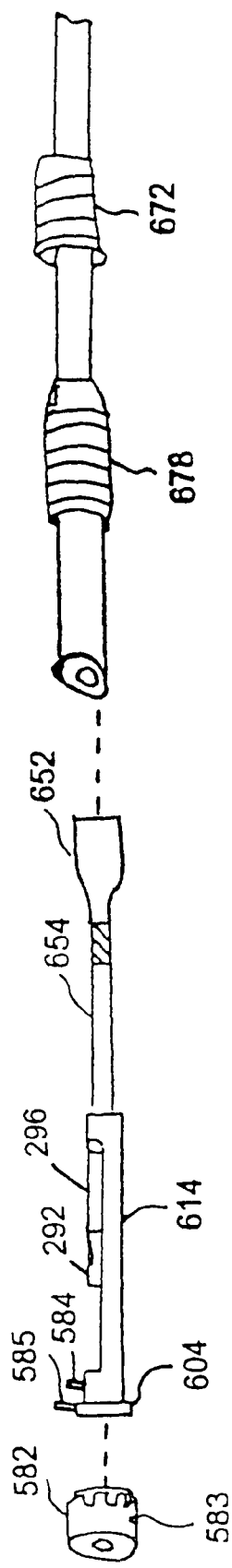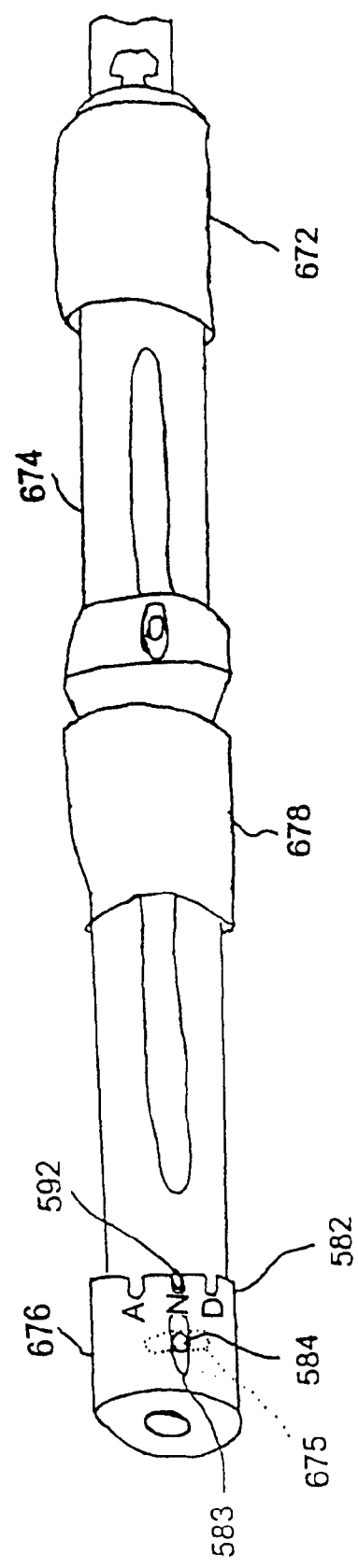
FIG. 50
FIG. 51

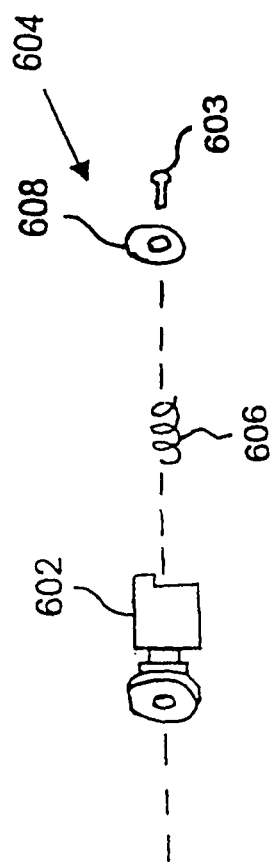
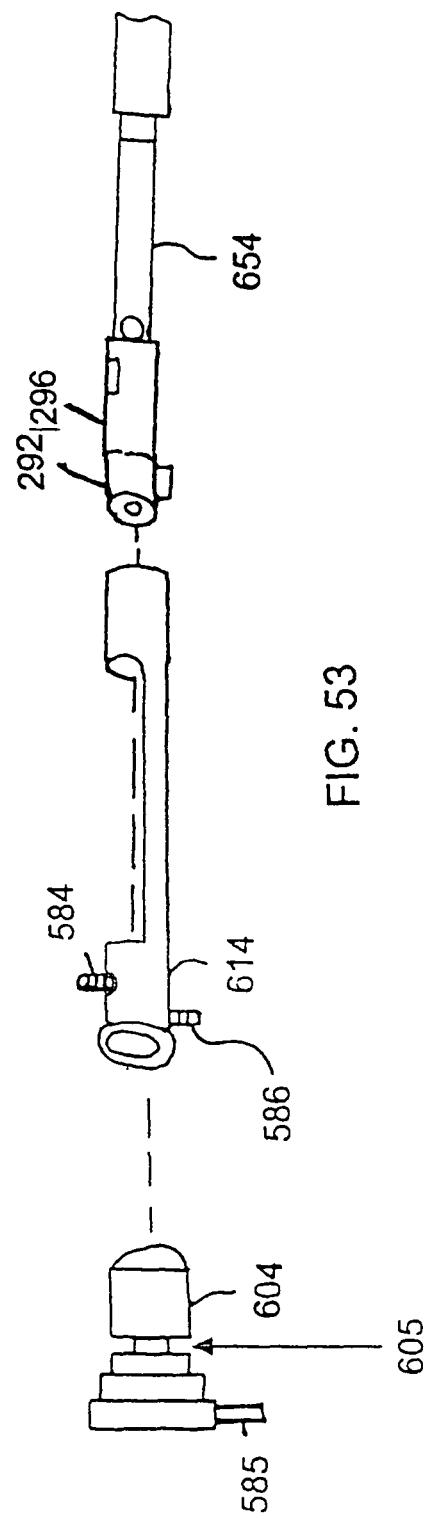
FIG. 52
FIG. 53

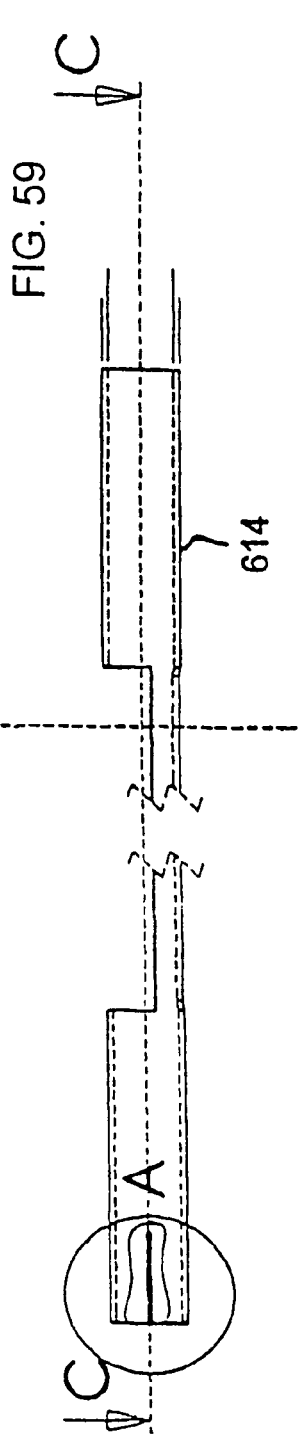
FIG. 59
FIG. 60
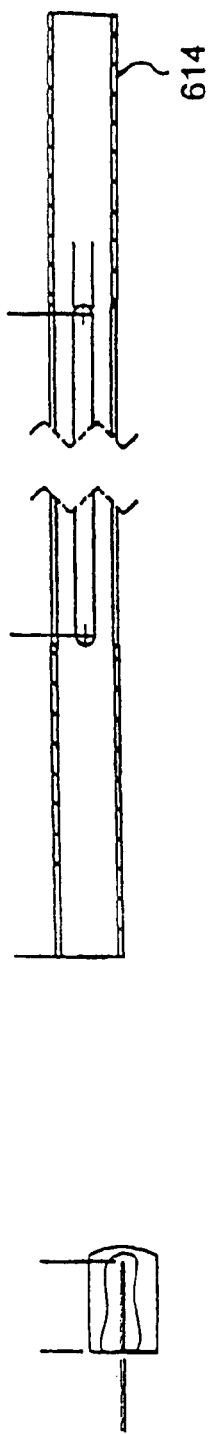
FIG. 61
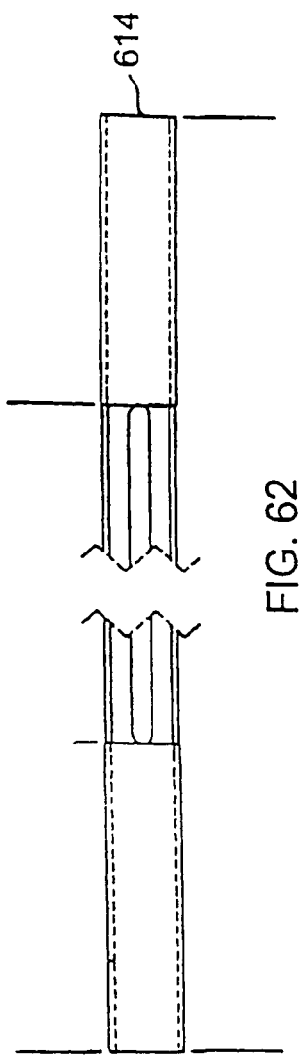
FIG. 62

METHODS OF IMPLANTING A PROSTHESIS AND TREATING AN ANEURYSM

CROSS-REFERENCE TO RELATED APPLICATION

This application is a continuation-in-part of U.S. patent application Ser. No. 10/784,462, filed Feb. 23, 2004 (entitled "Stent Graft"), now U.S. Pat. No. 8,292,943, issued on Oct. 23, 2012, which claims the benefit under 35 U.S.C. §119(e) of U.S. Provisional Application Nos. 60/499,652, filed Sep. 3, 2003, and 60/500,155, filed Sep. 4, 2003, and is a continuation-in-part of U.S. patent application Ser. No. 10/884,136, filed Jul. 2, 2004 (entitled "Self-Aligning Stent Graft Delivery System, Kit and Method"), now U.S. Pat. No. 7,763,063, issued on Jul. 27, 2010, which also claims the benefit under 35 U.S.C. §119(e) of U.S. Provisional Application Nos. 60/499, 652, filed Sep. 3, 2003, and 60/500,155, filed Sep. 4, 2003, the complete disclosures of all prior applications are hereby incorporated by reference herein in their entirety.

BACKGROUND OF THE INVENTION

1. Field of the Invention

The invention lies in the field of endoluminal blood vessel repairs. The invention specifically relates to a delivery system, a kit, and method for endoluminally repairing aneurysm and/or dissections of the thoracic transverse aortic arch, thoracic posterior aortic arch, and the descending thoracic portion of the aorta with a self-aligning stent graft.

2. Description of the Related Art

A stent graft is an implantable device made of a tube-shaped surgical graft covering and an expanding or self-expanding frame. The stent graft is placed inside a blood vessel to bridge, for example, an aneurismal, dissected, or other diseased segment of the blood vessel, and, thereby, exclude the hemodynamic pressures of blood flow from the diseased segment of the blood vessel.

In selected patients, a stent graft advantageously eliminates the need to perform open thoracic or abdominal surgical procedures to treat diseases of the aorta and eliminates the need for total aortic reconstruction. Thus, the patient has less trauma and experiences a decrease in hospitalization and recovery times. The time needed to insert a stent graft is substantially less than the typical anesthesia time required for open aortic bypass surgical repair, for example.

Use of surgical and/or endovascular grafts have widespread use throughout the world in vascular surgery. There are many different kinds of vascular graft configurations. Some have supporting framework over their entirety, some have only two stents as a supporting framework, and others simply have the tube-shaped graft material with no additional supporting framework, an example that is not relevant to the present invention.

One of the most commonly known supporting stent graft frameworks is that disclosed in U.S. Pat. Nos. 5,282,824 and 5,507,771 to Gianturco (hereinafter collectively referred to as "Gianturco"). Gianturco describes a zig-zag-shaped, self-expanding stent commonly referred to as a z-stent. The stents are, preferably, made of nitinol, but also have been made from stainless steel and other biocompatible materials.

There are various features characterizing a stent graft. The first significant feature is the tube of graft material. This tube is commonly referred to as the graft and forms the tubular shape that will, ultimately, take the place the diseased portion of the blood vessel. The graft is, preferably, made of a woven sheet (tube) of polyester or PTFE. The circumference of the graft tube is, typically, at least as large as the diameter and/or circumference of the vessel into which the graft will be inserted so that there is no possibility of blood flowing around the graft (also referred to as endoleak) to either displace the graft or to reapply hemodynamic pressure against the diseased portion of the blood vessel. Accordingly, to so hold the graft, self-expanding frameworks are attached typically to the graft material, whether on the interior or exterior thereof. Because blood flow within the lumen of the graft could be impaired if the framework was disposed on the interior wall of the graft, the framework is connected typically to the exterior wall of the graft. The ridges formed by such an exterior framework help to provide a better fit in the vessel by providing a sufficiently uneven outer surface that naturally grips the vessel where it contacts the vessel wall and also provides areas around which the vessel wall can endothelialize to further secure the stent graft in place.

One of the significant dangers in endovascular graft technology is the possibility of the graft migrating from the desired position in which it is installed. Therefore, various devices have been created to assist in anchoring the graft to the vessel wall.

One type of prior art prosthetic device is a stent graft made of a self-expanding metallic framework. For delivery, the stent graft is, first, radially compressed and loaded into an introducer system that will deliver the device to the target area. When the introducer system holding the stent graft positioned in an appropriate location in the vessel and allowed to open, the radial force imparted by the self-expanding framework is helpful, but, sometimes, not entirely sufficient, in endoluminally securing the stent graft within the vessel.

U.S. Pat. No. 5,824,041 to Lenker et al. (hereinafter "Lenker") discloses an example of a stent graft delivery system. Lenker discloses various embodiments in which a sheath is retractable proximally over a prosthesis to be released. With regard to FIGS. 7 and 8, Lenker names components 72 and 76, respectively, as "sheath" and "prosthesis-containment sheath." However, the latter is merely the catheter in which the prosthesis 74 and the sheath 72 are held. With regard to FIGS. 9 and 10, the sheath 82 has inner and outer layers 91, 92 fluid-tightly connected to one another to form a ballooning structure around the prosthesis P. This ballooning structure inflates when liquid is inflated with a non-compressible fluid medium and flares radially outward when inflated. With regard to FIGS. 13 to 15, Lenker discloses the "sheath" 120, which is merely the delivery catheter, and an eversible membrane 126 that "folds back over itself (everts) as the sheath 120 is retracted so that there are always two layers of the membrane between the distal end of the sheath [120] and the prosthesis P." Lenker at col. 9, lines 63 to 66. The eversion (peeling back) is caused by direct connection of the distal end 130 to the sheath 120. The Lenker delivery system shown in FIGS. 19A to 19D holds the prosthesis P at both ends 256, 258 while an outer catheter 254 is retracted over the prosthesis P and the inner sheath 260. The inner sheath 260 remains inside the outer catheter 254 before, during, and after retraction. Another structure for holding the prosthesis P at both ends is illustrated in FIGS. 23A and 23B. Therein, the proximal holder having resilient axial members 342 is connected to a proximal ring structure 346. FIGS. 24A to 24C also show an embodiment for holding the prosthesis at both ends inside thin-walled tube 362.

To augment radial forces of stents, some prior art devices have added proximal and/or distal stents that are not entirely covered by the graft material. By not covering with graft material a portion of the proximal/distal ends of the stent, these stents have the ability to expand further radially than those stents that are entirely covered by the graft material. By expanding further, the proximal/distal stent ends better secure to the interior wall of the vessel and, in doing so, press the extreme cross-sectional surface of the graft ends into the vessel wall to create a fixated blood-tight seal.

One example of such a prior art exposed stent can be found in United States Patent Publication US 2002/0198587 to Greenberg et al. The modular stent graft assembly therein has a three-part stent graft: a two-part graft having an aortic section 12 and an iliac section 14 (with four sizes for each) and a contralateral iliac occluder 80. FIGS. 1, 2, and 4 to 6 show the attachment stent 32. As illustrated in FIGS. 1, 2, and 4, the attachment stent 32, while rounded, is relatively sharp and, therefore, increases the probability of puncturing the vessel.

A second example of a prior art exposed stent can be found in U.S. Patent Publication 2003/0074049 to Hoganson et al. (hereinafter "Hoganson"), which discloses a covered stent 10 in which the elongated portions or sections 24 of the ends 20a and 20b extend beyond the marginal edges of the cover 22. See Hoganson at FIGS. 1, 3, 9, 11a, 11b, 12a, 12b, and 13. However, these extending exposed edges are triangular, with sharp apices pointing both upstream and downstream with regard to a graft placement location. Such a configuration of the exposed stent 20a, 20b increases the possibility of puncturing the vessel. In various embodiments shown in FIGS. 6a, 6b, 6c, 10, 14a, Hoganson teaches completely covering the extended stent and, therefore, the absence of a stent extending from the cover 22. It is noted that the Hoganson stent is implanted by inflation of a balloon catheter.

Another example of a prior art exposed stent can be found in U.S. Pat. No. 6,565,596 to White et al. (hereinafter "White I"), which uses a proximally extending stent to prevent twisting or kinking and to maintain graft against longitudinal movement. The extending stent is expanded by a balloon and has a sinusoidal amplitude greater than the next adjacent one or two sinusoidal wires. White I indicates that it is desirable to space wires adjacent upstream end of graft as close together as is possible. The stent wires of White I are actually woven into graft body by piercing the graft body at various locations. See White I at FIGS. 6 and 7. Thus, the rips in the graft body can lead to the possibility of the exposed stent moving with respect to the graft and of the graft body ripping further. Between the portions of the extending stent 17, the graft body has apertures.

The stent configuration of U.S. Pat. No. 5,716,393 to Lindenberg et al. is similar to White I in that the outermost portion of the one-piece stent—made from a sheet that is cut/punched and then rolled into cylinder—has a front end with a greater amplitude than the remaining body of the stent A further example of a prior art exposed stent can be found in U.S. Pat. No. 6,524,335 to Hartley et al. (hereinafter "Hartley"). FIGS. 1 and 2 of Hartley particularly disclose a proximal first stent 1 extending proximally from graft proximal end 4 with both the proximal and distal apices narrowing to pointed ends.

Yet another example of a prior art exposed stent can be found in U.S. Pat. No. 6,355,056 to Pinheiro (hereinafter "Pinheiro I"). Like the Hartley exposed stent, Pinheiro discloses exposed stents having triangular, sharp proximal apices.

Still a further example of a prior art exposed stent can be found in U.S. Pat. No. 6,099,558 to White et al. (hereinafter "White II"). The White II exposed stent is similar to the exposed stent of White I and also uses a balloon to expand the stent.

An added example of a prior art exposed stent can be found in U.S. Pat. No. 5,871,536 to Lazarus, which discloses two support members 68 longitudinally extending from proximal end to a rounded point. Such points, however, create a very significant possibility of piercing the vessel.

An additional example of a prior art exposed stent can be found in U.S. Pat. No. 5,851,228 to Pinheiro (hereinafter "Pinheiro II"). The Pinheiro II exposed stents are similar to the exposed stents of Pinheiro I and, as such, have triangular, sharp, proximal apices.

Still another example of a prior art exposed stent can be found in Lenker (U.S. Pat. No. 5,824,041), which shows a squared-off end of the proximal and distal exposed band members 14. A portion of the exposed members 14 that is attached to the graft material 18, 20 is longitudinally larger than a portion of the exposed members 14 that is exposed and extends away from the graft material 18, 20. Lenker et al. does not describe the members 14 in any detail.

Yet a further example of a prior art exposed stent can be found in U.S. Pat. No. 5,824,036 to Lauterjung, which, of all of the prior art embodiments described herein, shows the most pointed of exposed stents. Specifically, the proximal ends of the exposed stent are apices pointed like a minaret. The minaret points are so shaped intentionally to allow forks 300 (see Lauterjung at FIG. 5) external to the stent 154 to pull the stent 154 from the sheath 302, as opposed to being pushed.

A final example of a prior art exposed stent can be found in U.S. Pat. No. 5,755,778 to Kleshinski. The Kleshinski exposed stents each have two different shaped portions, a triangular base portion and a looped end portion. The totality of each exposed cycle resembles a castellation. Even though the end-most portion of the stent is curved, because it is relatively narrow, it still creates the possibility of piercing the vessel wall.

All of these prior art stents suffer from the disadvantageous characteristic that the relatively sharp proximal apices of the exposed stents have a shape that is likely to puncture the vessel wall.

Devices other than exposed stents have been used to inhibit graft migration. A second of such devices is the placement of a relatively stiff longitudinal support member longitudinally extending along the entirety of the graft.

The typical stent graft has a tubular body and a circumferential framework. This framework is not usually continuous. Rather, it typically takes the form of a series of rings along the tubular graft. Some stent grafts have only one or two of such rings at the proximal and/or distal ends and some have many stents tandemly placed along the entirety of the graft material. Thus, the overall stent graft has an "accordion" shape. During the systolic phase of each cardiac cycle, the hemodynamic pressure within the vessel is substantially parallel with the longitudinal plane of the stent graft. Therefore, a device having unsecured stents, could behave like an accordion or concertina with each systolic pulsation, and may have a tendency to migrate downstream. (A downstream migration, to achieve forward motion, has a repetitive longitudinal compression and extension of its cylindrical body.) Such movement is entirely undesirable. Connecting the stents with support along the longitudinal extent of the device thereof can prevent such movement. To provide such support, a second antimigration device can be embodied as a relatively stiff longitudinal bar connected to the framework.

A clear example of a longitudinal support bar can be found in Pinheiro I (U.S. Pat. No. 6,355,056) and Pinheiro II (U.S. Pat. No. 5,851,228). Each of these references discloses a plurality of longitudinally extending struts 40 extending between and directly interconnecting the proximal and distal exposed stents 20a, 20b. These struts 40 are designed to extend generally parallel with the inner lumen 15 of the graft 10, in other words, they are straight.

Another example of a longitudinal support bar can be found in U.S. Pat. No. 6,464,719 to Jayaraman. The Jayaraman stent is formed from a graft tube 21 and a supporting sheet 1 made of nitinol. This sheet is best shown in FIG. 3. The end pieces 11, 13 of the sheet are directly connected to one another by wavy longitudinal connecting pieces 15 formed by cutting the sheet 1. To form the stent graft, the sheet 1 is coiled with or around the cylindrical tube 21. See FIGS. 1 and 4. Alternatively, a plurality of connecting pieces 53 with holes at each end thereof can be attached to a cylindrical fabric tube 51 by stitching or sutures 57, as shown in FIG. 8. Jayaraman requires more than one of these serpentine shaped connecting pieces 53 to provide longitudinal support.

United States Patent Publication 2002/0016627 and U.S. Pat. No. 6,312,458 to Golds each disclose a variation of a coiled securing member 20.

A different kind of supporting member is disclosed in FIG. 8 of U.S. Pat. No. 6,053,943 to Edwin et al.

Like Jayaraman, U.S. Pat. No. 5,871,536 to Lazarus discloses a plurality of straight, longitudinal support structures 38 attached to the circumferential support structures 36, see FIGS. 1, 6, 7, 8, 10, 11, 12, 14. FIG. 8 of Lazarus illustrates the longitudinal support structures 38 attached to a distal structure 36 and extending almost all of the way to the proximal structure 36. The longitudinal structures 38, 84, 94 can be directly connected to the body 22, 80 and can be telescopic 38, 64.

United States Patent Publication 2003/0088305 to Van Schie et al. (hereinafter "Van Schie") does not disclose a support bar. Rather, it discloses a curved stent graft using an elastic material 8 connected to stents at a proximal end 2 and at a distal end 3 (see FIGS. 1, 2) thereof to create a curved stent graft. Because Van Schie needs to create a flexible curved graft, the elastic material 8 is made of silicone rubber or another similar material. Thus, the material 8 cannot provide support in the longitudinal extent of the stent graft. Accordingly, an alternative to the elastic support material 8 is a suture material 25 shown in FIGS. 3 to 6.

SUMMARY OF THE INVENTION

The invention provides a two-part expanding stent graft delivery system and method for implanting a prosthesis with the delivery system that overcome the hereinafore-mentioned disadvantages of the heretofore-known devices and methods of this general type and that provides a vessel repair device that implants/conforms more efficiently within the natural or diseased course of the aorta by aligning with the natural curve of the aorta, decreases the likelihood of vessel puncture, increases the blood-tight vascular connection, retains the intraluminal wall of the vessel position, is more resistant to migration, and delivers the stent graft into a curved vessel while minimizing intraluminal forces imparted during delivery and while minimizing the forces needed for a user to deliver the stent graft into a curved vessel.

With the foregoing and other objects in view, there is provided, in accordance with the invention, a method of implanting a prosthesis in a patient at a treatment site, including the steps of providing a prosthesis delivery system with an inner sheath and an outer sheath, loading a prosthesis inside the inner sheath, loading the inner sheath containing the prosthesis within the outer sheath, advancing the outer sheath in a patient towards the treatment site up to a given position at a distance from the treatment site, while retaining the outer sheath in the given position: advancing the inner sheath out from the outer sheath to the treatment site to align the prosthesis with the treatment site, and retracting the inner sheath to at least partially implant the prosthesis at the treatment site, and upon completion of prosthesis implantation, retracting both of the inner and outer sheaths from the patient.

In accordance with another mode of the invention, the advancing step is carried out by advancing the inner sheath out from the outer sheath to the treatment site to axially align the prosthesis with the treatment site and rotating the inner sheath to circumferentially align the prosthesis with the treatment site.

In accordance with a further mode of the invention, the advancing step is carried out by advancing the outer sheath towards the treatment site only up to a point at a distance from the treatment site greater than a length of the prosthesis.

In accordance with an added mode of the invention, the advancing step is carried out by advancing the outer sheath in vasculature of a patient towards a vascular treatment site.

In accordance with an additional mode of the invention, the advancing step is carried out by advancing the outer sheath in aortic vasculature of the patient no closer to the heart than a celiac axis of the patient.

In accordance with yet another mode of the invention, the advancing step is carried out by advancing the outer sheath in aortic vasculature of the patient to a point in the aorta no closer to a heart of the patient than a celiac axis of the patient.

In accordance with yet a further mode of the invention, the outer sheath is provided with a length sufficient to reach only up to a celiac axis of a patient.

In accordance with yet an added mode of the invention, the outer sheath is provided with a length no greater than a distance from the patient's femoral arterial access site to the patient's celiac axis.

In accordance with yet an additional mode of the invention, the retracting step is carried out upon completion of prosthesis implantation by retracting the inner sheath into the outer sheath and, subsequently, the outer sheath containing the inner sheath is retracted from the patient.

In accordance with again another mode of the invention, the inner sheath is of a material relatively more flexible than a material of the outer sheath.

In accordance with again a further mode of the invention, the prosthesis delivery system has an inner sheath that relatively more flexible than the outer sheath.

In accordance with again an added mode of the invention, the inner sheath has a prosthesis holding inner diameter at least as great as an inner diameter of the outer sheath.

With the objects of the invention in view, there is also provided a method of implanting a prosthesis in a patient at a treatment site, including the steps of axially locking a set of inner catheters with respect to an outer catheter, at least a portion of one of the inner catheters constraining the prosthesis, threading the inner and outer catheters onto a guidewire and into a patient to place the outer catheter into an aorta of the patient only up to a point at a distance from the treatment site greater than a length of the prosthesis, unlocking the inner catheters with respect to the outer catheter, advancing the inner catheters distally out of the outer catheter in the aorta towards the patient's heart to transport the prosthesis further upstream into the aorta, unlocking the one inner catheter that is constraining the prosthesis from the remainder of the inner catheters, and retracting the one inner catheter in a proximal direction to at least partially implant the prosthesis in the vessel.

With the objects of the invention in view, there is also provided a method of implanting a prosthesis in a patient at a treatment site, including the steps of axially locking a set of inner catheters with respect to an outer catheter, at least a portion of one of the inner catheters constraining the prosthesis, threading the inner and outer catheters onto a guidewire and into a patient to place the outer catheter into an aorta of the patient no closer to the heart than approximately at the patient's celiac axis, unlocking the inner catheters with respect to the outer catheter, advancing the inner catheters distally out of the outer catheter in the aorta towards the patient's heart to transport the prosthesis further upstream into the aorta, unlocking the one inner catheter that is constraining the prosthesis from the remainder of the inner catheters, and retracting the one inner catheter in a proximal direction to at least partially implant the prosthesis in the vessel.

In accordance with again an additional mode of the invention, the threading step is carried out by threading the inner and outer catheters into the patient at a femoral access site.

In accordance with still another mode of the invention, before axially locking the inner catheters with respect to the outer catheter: the prosthesis is loaded within a sheath connected to the one inner catheter, the sheath being smaller in diameter than the prosthesis to radially compress the prosthesis therein, the inner catheters are loaded within the outer catheter to radially compress the sheath and to further radially compress the prosthesis, and the inner catheters are axially locked with respect to one another.

In accordance with still a further mode of the invention, the loading step is carried out by additionally releasably connecting a distal portion of the prosthesis with a portion of one of the inner catheters different from the one inner catheter and, after retracting the one inner catheter, the prosthesis is finally deployed in the vessel by releasing the distal portion of the prosthesis from the portion.

In accordance with still an added mode of the invention, the sheath is of a relatively flexible material and the outer catheter is of a relatively stiff material.

In accordance with still an additional mode of the invention, the advancing step is carried out by advancing the inner catheters distally out of the outer catheter and into the curved thoracic aorta.

In accordance with another mode of the invention, prior to unlocking the one inner catheter from the remainder of the inner catheters, the axially locked inner catheters are rotated to place the prosthesis in a desired rotational implanting position.

In accordance with a concomitant mode of the invention, the prosthesis is provided with a supporting rod, and the rotation step is carried out by rotating the prosthesis to approximately align the supporting rod along a superior longitudinal line of a curved portion of the thoracic aorta.

Other features that are considered as characteristic for the invention are set forth in the appended claims.

Although the invention is illustrated and described herein as embodied in a two-part expanding stent graft delivery system and method for implanting a prosthesis with the delivery system, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

The features of the present invention, which are believed to be novel, are set forth with particularity in the appended claims. The invention, together with further objects and advantages thereof, may best be understood by reference to the following description, taken in conjunction with the accompanying drawings, in the several figures of which like reference numerals identify like elements, and in which:

FIG. 1 is a side elevational view of a stent graft according to the invention;

FIG. 2 is a side elevational view of a stent of the stent graft of FIG. 1;

FIG. 3 is a cross-sectional view of the stent of FIG. 2 with different embodiments of protrusions;

FIG. 4 is a perspective view of a prior art round mandrel for forming prior art stents;

FIG. 5 is a fragmentary, side elevational view of a prior art stent in a portion of a vessel;

FIG. 6 is a perspective view of a dodecahedral-shaped mandrel for forming stents in FIGS. 1 to 3;

FIG. 7 is a fragmentary, side elevational view of the stent of FIGS. 1 to 3 in a portion of a vessel;

FIG. 8 is a fragmentary, enlarged side elevational view of the proximal end of the stent graft of FIG. 1 illustrating movement of a gimbaled end;

FIG. 9 is a side elevational view of a two-part stent graft according to the invention;

FIG. 10 is a fragmentary, side elevational view of a delivery system according to the invention with a locking ring in a neutral position;

FIG. 11 is a fragmentary, side elevational view of the delivery system of FIG. 10 with the locking ring in an advancement position and, as indicated by dashed lines, a distal handle and sheath assembly in an advanced position;

FIG. 12 is a fragmentary, enlarged view of a sheath assembly of the delivery system of FIG. 10;

FIG. 13 is a fragmentary, enlarged view of an apex capture device of the delivery system of FIG. 10 in a captured position;

FIG. 14 is a fragmentary, enlarged view of the apex capture device of FIG. 13 in a released position;

FIG. 15 is a fragmentary, enlarged view of an apex release assembly of the delivery system of FIG. 10 in the captured position;

FIG. 16 is a fragmentary, enlarged view of the apex release assembly of FIG. 15 in the captured position with an intermediate part removed;

FIG. 17 is a fragmentary, enlarged view of the apex release assembly of FIG. 16 in the released position;

FIG. 18 is a fragmentary, side elevational view of the delivery system of FIG. 11 showing how a user deploys the prosthesis;

FIG. 19 is a fragmentary cross-sectional view of human arteries including the aorta with the assembly of the present invention in a first step of a method for inserting the prosthesis according to the invention;

FIG. 20 is a fragmentary cross-sectional view of the arteries of FIG. 19 with the assembly in a subsequent step of the method for inserting the prosthesis;

FIG. 21 is a fragmentary cross-sectional view of the arteries of FIG. 20 with the assembly in a subsequent step of the method for inserting the prosthesis;

FIG. 22 is a fragmentary cross-sectional view of the arteries of FIG. 21 with the assembly in a subsequent step of the method for inserting the prosthesis;

FIG. 23 is a fragmentary cross-sectional view of the arteries of FIG. 22 with the assembly in a subsequent step of the method for inserting the prosthesis;

FIG. 24 is a fragmentary cross-sectional view of the arteries of FIG. 23 with the assembly in a subsequent step of the method for inserting the prosthesis;

FIG. 25 is a fragmentary, diagrammatic, perspective view of the coaxial relationship of delivery system lumen according to the invention;

FIG. 26 is a fragmentary, cross-sectional view of the apex release assembly according to the invention;

FIG. 27 is a fragmentary, side elevational view of the stent graft of FIG. 1 with various orientations of radiopaque markers according to the invention;

FIG. 28 is a fragmentary perspective view of the stent graft of FIG. 1 with various orientations of radiopaque markers according to the invention;

FIG. 33 is a fragmentary, cross-sectional view of an embodiment of handle assemblies according to the invention;

FIG. 40 is a perspective view of a rotator body of the handle assembly of FIG. 33;

FIG. 41 is an elevational and partially hidden side view of the rotator body of FIG. 40;

FIG. 42 is a cross-sectional view of the rotator body of FIG. 41 along section line A-A;

FIG. 43 is an elevational and partially hidden side view of the rotator body of FIG. 40;

FIG. 50 is a fragmentary, exploded side elevational view of a portion of a second embodiment of the handle assembly according to the invention;

FIG. 51 is a fragmentary, side elevational view of the portion of FIG. 50 in a neutral position;

FIG. 52 is an exploded view of a first portion of the second embodiment of the handle assembly;

FIG. 53 is a fragmentary, exploded view of a larger portion of the second embodiment of the handle assembly as compared to FIG. 52 with the first portion and the sheath assembly;

FIG. 59 is a fragmentary and partially hidden side elevational view of a clasp sleeve of the second embodiment of the handle assembly;

FIG. 60 is a fragmentary, cross-sectional view of a portion the clasp sleeve of FIG. 59 along section line A;

FIG. 61 is a fragmentary, cross-sectional view of the clasp sleeve of FIG. 59 along section line C-C;

FIG. 62 is a fragmentary and partially hidden side elevational view of the clasp sleeve of FIG. 59 rotated with respect to FIG. 59;

DESCRIPTION OF THE PREFERRED EMBODIMENTS

Figure 29:
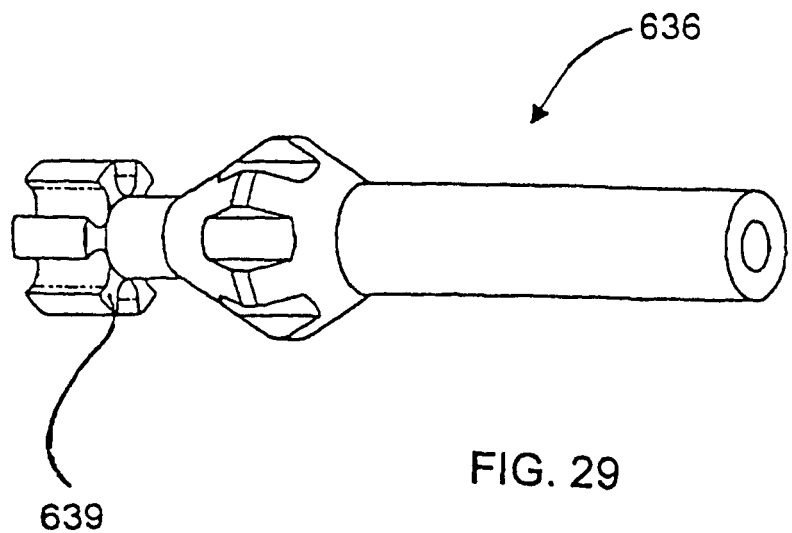
FIG. 29 is a perspective view of a distal apex head of the apex capture device of FIG. 13.
Figure 30:
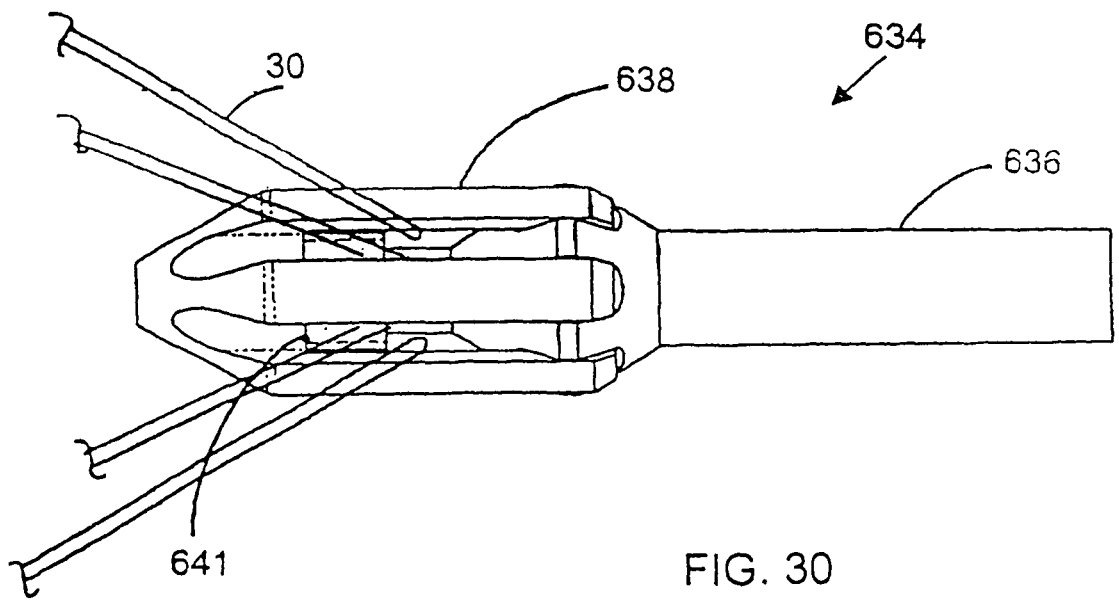
FIG. 30 is a fragmentary side elevational view of the distal apex head of FIG. 29 and a proximal apex body of the apex capture device of FIG. 13 with portions of a bare stent in the captured position.
Figure 31:
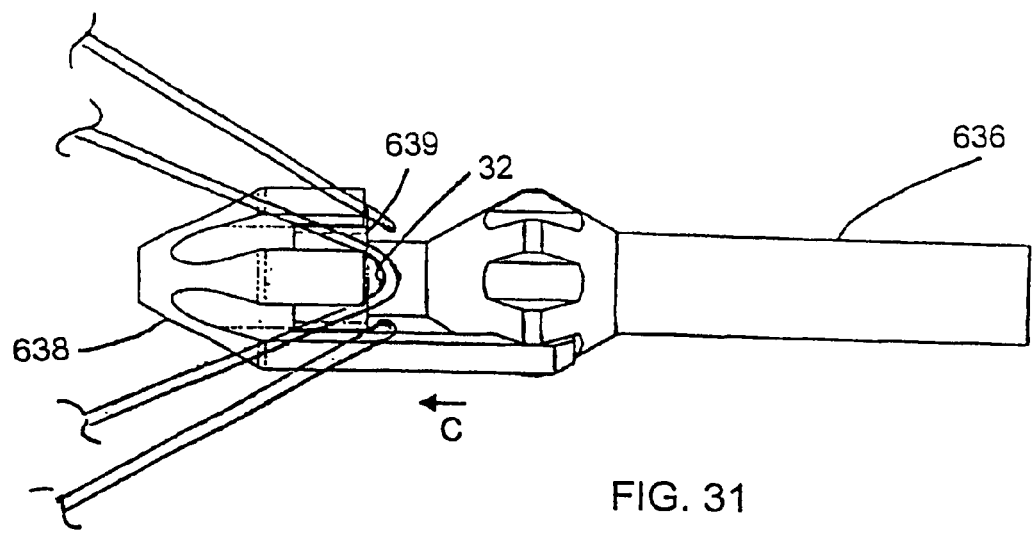
FIG. 31 is a fragmentary, side elevational view of the distal apex head and proximal apex body of FIG. 30 with a portion of the proximal apex body cut away to illustrate the bare stent in the captured position.

While the specification concludes with claims defining the features of the invention that are regarded as novel, it is believed that the invention will be better understood from a consideration of the following description in conjunction with the drawing figures, in which like reference numerals are carried forward.

The present invention provides a stent graft, delivery system, and method for implanting a prosthesis with a two-part expanding delivery system that treats, in particular, thoracic aortic defects from the brachiocephalic level of the aortic arch distally to a level just superior to the celiac axis and provides an endovascular foundation for an anastomosis with the thoracic aorta, while providing an alternative method for partial/total thoracic aortic repair by excluding the vessel defect and making surgical repair of the aorta unnecessary. The stent graft of the present invention, however, is not limited to use in the aorta. It can be endoluminally inserted in any accessible artery that could accommodate the stent graft's dimensions.

Stent Graft

The stent graft according to the present invention provides various features that, heretofore, have not been applied in the art and, thereby, provide a vessel repair device that implants/conforms more efficiently within the natural or diseased course of the aorta, decreases the likelihood of vessel puncture, and increases the blood-tight vascular connection, and decreases the probability of graft mobility.

The stent graft is implanted endovascularly before or during or in place of an open repair of the vessel (i.e., an arch, in particular, the ascending and/or descending portion of the aorta) through a delivery system described in detail below. The typical defects treated by the stent graft are aortic aneurysms, aortic dissections, and other diseases such as penetrating aortic ulcer, coarctation, and patent ductus arteriosus, related to the aorta. When endovascularly placed in the aorta, the stent graft forms a seal in the vessel and automatically affixes itself to the vessel with resultant effacement of the pathological lesion.

Referring now to the figures of the drawings in detail and first, particularly to FIG. 1 thereof, there is shown an improved stent graft 1 having a graft sleeve 10 and a number of stents 20. These stents 20 are, preferably, made of nitinol, an alloy having particularly special properties allowing it to rebound to a set configuration after compression, the rebounding property being based upon the temperature at which the alloy exists. For a detailed explanation of nitinol and its application with regard to stents, see, e.g., U.S. Pat. Nos. 4,665,906, 5,067,957, and 5,597,378 to Jervis and to Gianturco.

The graft sleeve 10 is cylindrical in shape and is made of a woven graft material along its entire length. The graft material is, preferably, polyester, in particular, polyester referred to under the name DACRON® or other material types like Expanded Polytetrafluoroethylene ("EPTFE"), or other polymeric based coverings. The tubular graft sleeve 10 has a framework of individual lumen-supporting wires each referred to in the art as a stent 20. Connection of each stent 20 is, preferably, performed by sewing a polymeric (nylon, polyester) thread around an entirety of the stent 20 and through the graft sleeve 10. The stitch spacings are sufficiently close to prevent any edge of the stent 20 from extending substantially further from the outer circumference of the graft sleeve 10 than the diameter of the wire itself. Preferably, the stitches have a 0.5 mm to 5 mm spacing.

The stents 20 are sewn either to the exterior or interior surfaces of the graft sleeve 10. FIG. 1 illustrates all stents 20, 30 on the exterior surface 16 of the graft sleeve 10. In a preferred non-illustrated embodiment, the most proximal 23 and distal stents and a bare stent 30 are connected to the interior surface of the graft sleeve 10 and the remainder of the stents 20 are connected to the exterior surface 16. Another possible non-illustrated embodiment alternates connection of the stents 20, 30 to the graft sleeve 10 from the graft exterior surface to the graft interior surface, the alternation having any periodic sequence.

A stent 20, when connected to the graft sleeve 10, radially forces the graft sleeve 10 open to a predetermined diameter D. The released radial force creates a seal with the vessel wall and affixes the graft to the vessel wall when the graft is implanted in the vessel and is allowed to expand.

Typically, the stents 20 are sized to fully expand to the diameter D of the fully expanded graft sleeve 10. However, a characteristic of the present invention is that each of the stents 20 and 30 has a diameter larger than the diameter D of the fully expanded graft sleeve 10. Thus, when the stent graft 1 is fully expanded and resting on the internal surface of the vessel where it has been placed, each stent 20 is imparting independently a radially directed force to the graft sleeve 10. Such pre-compression, as it is referred to herein, is applied (1) to ensure that the graft covering is fully extended, (2) to ensure sufficient stent radial force to make sure sealing occurs, (3) to affix the stent graft and prevent it from kinking, and (4) to affix the stent graft and prevent migration.

Preferably, each of the stents 20 is formed with a single nitinol wire. Of course other biocompatible materials can be used, for example, stainless steel, biopolymers, cobalt chrome, and titanium alloys.

The preferred shape of each stent 20 corresponds to what is referred in the art as a Z-stent, see, e.g., Gianturco (although the shape of the stents 20 can be in any form that satisfies the functions of a self-expanding stent). Thus, the wire forming the stent 20 is a ring having a wavy or sinusoidal shape. In particular, an elevational view orthogonal to the center axis 21 of the stent 20 reveals a shape somewhere between a triangular wave and a sinusoidal wave as shown in FIG. 2. In other words, the view of FIG. 2 shows that the stents 20 each have alternating proximal 22 and distal 24 apices. Preferably, the apices have a radius r that does not present too great of a point towards a vessel wall to prevent any possibility of puncturing the vessel, regardless of the complete circumferential connection to the graft sleeve 10. In particular, the radius r of curvature of the proximal 22 and distal 24 apices of the stent 20 are, preferably, equal. The radius of curvature r is between approximately 0.1 mm and approximately 3.0 mm, in particular, approximately 0.5 mm.

Another advantageous feature of a stent lies in extending the longitudinal profile along which the stent contacts the inner wall of a vessel. This longitudinal profile can be explained with reference to FIGS. 3 to 7.

Prior art stents and stents according to the present invention are formed on mandrels 29, 29' by winding the wire around the mandrel 29, 29' and forming the apexes 22, 24, 32, 34 by wrapping the wire over non-illustrated pins that protrude perpendicular from the axis of the mandrel. Such pins, if illustrated, would be located in the holes illustrated in the mandrels 29, 29' of FIGS. 4 and 6. Prior art stents are formed on a round mandrel 29 (also referred to as a bar). A stent 20' formed on a round mandrel 29 has a profile that is rounded (see FIG. 5). Because of the rounded profile, the stent 20' does not conform evenly against the inner wall of the vessel 2 in which it is inserted. This disadvantage is critical in the area of stent graft 1 seal zones—areas where the ends of the graft 10 need to be laid against the inner wall of the vessel 2. Clinical experience reveals that stents 20' formed with the round mandrel 29 do not lie against the vessel 2; instead, only a mid-section of the stent 20' rests against the vessel 2, as shown in FIG. 5. Accordingly, when such a stent 20' is present at either of the proximal 12 or distal 14 ends of the stent graft 1, the graft material flares away from the wall of the vessel 2 into the lumen—a condition that is to be avoided. An example of this flaring can be seen by comparing the upper and lower portions of the curved longitudinal profile of the stent 20' in FIG. 5 with the linear longitudinal profile of the vessel 2.

To remedy this problem and ensure co-columnar apposition of the stent and vessel, stents 20 of the present invention are formed on a multiple-sided mandrel. In particular, the stents 20 are formed on a polygonal-shaped mandrel 29'. The mandrel 29' does not have sharp edges. Instead, it has flat sections and rounded edge portions between the respective flat sections. Thus, a stent formed on the mandrel 29' will have a cross-section that is somewhat round but polygonal, as shown in FIG. 3. The cross-sectional view orthogonal to the center axis 21 of such a stent 20 will have beveled or rounded edges 31 (corresponding to the rounded edge portions of the mandrel 29') disposed between flat sides or struts 33 (corresponding to the flat sections of the mandrel 29').

To manufacture the stent 20, apexes of the stents 20 are formed by winding the wire over non-illustrated pins located on the rounded portions of the mandrel 29'. Thus, the struts 33 lying between the apexes 22, 24, 32, 34 of the stents 20 lie flat against the flat sides of the mandrel 29'. When so formed on the inventive mandrel 29', the longitudinal profile is substantially less rounded than the profile of stent 20' and, in practice, is substantially linear.

For stents 20 having six proximal 22 and six distal 24 apices, the stents 20 are formed on a dodecahedron-shaped mandrel 29' (a mandrel having twelve sides), which mandrel 29' is shown in FIG. 6. A stent 20 formed on such a mandrel 29' will have the cross-section illustrated in FIG. 3.

The fourteen-apex stent 20 shown in FIG. 7 illustrates a stent 20 that has been formed on a fourteen-sided mandrel. The stent 20 in FIG. 7 is polygonal in cross-section (having fourteen sides) and, as shown in FIG. 7, has a substantially linear longitudinal profile. Clinically, the linear longitudinal profile improves the stent's 20 ability to conform to the vessel 2 and press the graft sleeve 10 outward in the sealing zones at the extremities of the individual stent 20.

Another way to improve the performance of the stent graft 1 is to provide the distal-most stent 25 on the graft 10 (i.e., downstream) with additional apices and to give it a longer longitudinal length (i.e., greater amplitude) and/or a longer circumferential length. When a stent 25 having a longer circumferential length is sewn to a graft, the stent graft 1 will perform better clinically. The improvement, in part, is due to a need for the distal portion of the graft material 10 to be pressed firmly against the wall of the vessel. The additional apices result in additional points of contact between the stent graft 1 and vessel wall, thus ensuring better apposition to the wall of the vessel and better sealing of the graft material 10 to the vessel. The increased apposition and sealing substantially improves the axial alignment of the distal end 14 of the stent graft 1 to the vessel. As set forth above, each of the stents 20 and 30 has a diameter larger than the diameter D of the fully expanded graft sleeve 10. Thus, if the distal stent 25 also has a diameter larger than the diameter D, it will impart a greater radial bias on all 360 degrees of the corresponding section of the graft than stents not having such an oversized configuration.

A typical implanted stent graft 1 typically does not experience a lifting off at straight portions of a vessel because the radial bias of the stents acting upon the graft sleeve give adequate pressure to align the stent and graft sleeve with the vessel wall. However, when a typical stent graft is implanted in a curved vessel (such as the aorta), the distal end of the stent graft 1 does experience a lift off from the vessel wall. The increased apposition and sealing of the stent graft 1 according to the present invention substantially decreases the probability of lift off because the added height and additional apices enhance the alignment of the stent graft perpendicular to the vessel wall as compared to prior art stent grafts (no lift off occurs).

The number of total apices of a stent is dependent upon the diameter of the vessel in which the stent graft 1 is to be implanted. Vessels having a smaller diameter have a smaller total number of apices than a stent to be implanted in a vessel having a larger diameter. Table 1 below indicates preferred stent embodiments for vessels having different diameters. For example, if a vessel has a 26 or 27 mm diameter, then a preferred diameter of the graft sleeve 10 is 30 mm. For a 30 mm diameter graft sleeve, the intermediate stents 20 will have 5 apices on each side (proximal and distal) for a total of 10 apices. In other words, the stent defines 5 periodic "waves." The distal-most stent 25, in comparison, defines 6 periodic "waves" and, therefore, has 12 total apices. It is noted that the distal-most stent 25 in FIG. 1 does not have the additional apex. While Table 1 indicates preferred embodiments, these configurations can be adjusted or changed as needed.

TABLE 1

| Vessel Diameter (mm) | Graft Diameter (mm) | Stent Apices/Side (Distal-most Stent #) |
|---|---|---|
| 19 | 22 | 5(5) |
| 20-21 | 24 | 5(5) |
| 22-23 | 26 | 5(5) |
| 24-25 | 28 | 5(6) |
| 26-27 | 30 | 5(6) |
| 28-29 | 32 | 6(7) |
| 30-31 | 34 | 6(7) |
| 32-33 | 36 | 6(7) |
| 34 | 38 | 6(7) |
| 35-36 | 40 | 7(8) |
| 37-38 | 42 | 7(8) |
| 39-40 | 44 | 7(8) |
| 41-42 | 46 | 7(8) |

To increase the security of the stent graft 1 in a vessel, an exposed or bare stent 30 is provided on the stent graft 1, preferably, only at the proximal end 12 of the graft sleeve 10—proximal meaning that it is attached to the portion of the graft sleeve 10 from which the blood flows into the sleeve, i.e., blood flows from the bare stent 30 and through the sleeve 10 to the left of FIG. 1. The bare stent 30 is not limited to being attached at the proximal end 12. Another non-illustrated bare stent can be attached similarly to the distal end 14 of the graft sleeve 10.

Significantly, the bare stent 30 is only partially attached to the graft sleeve 10. Specifically, the bare stent 30 is fixed to the graft sleeve 10 only at the distal apices 34 of the bare stent 30. Thus, the bare stent 30 is partially free to extend the proximal apices 32 away from the proximal end of the graft sleeve 10.

The bare stent 30 has various properties, the primary one being to improve the apposition of the graft material to the contour of the vessel wall and to align the proximal portion of the graft covering in the lumen of the arch and provide a blood-tight closure of the proximal end 12 of the graft sleeve 10 so that blood does not pass between the vascular inside wall and outer surface 16 of the sleeve 10 (endoleak).

The preferred configuration for the radius of curvature α of the distal apices 34 is substantially equal to the radius r of the proximal 22 and distal 24 apices of the stent 20, in particular, it is equal at least to the radius of curvature r of the proximal apices of the stent 20 directly adjacent the bare stent 30. Thus, as shown in FIG. 8, a distance between the proximal apices 22 of the most proximal stent 23 and crossing points of the exposed portions of the bare stent 30 are substantially at a same distance from one another all the way around the circumference of the proximal end 12 of the graft sleeve 10. Preferably, this distance varies based upon the graft diameter. Accordingly, the sinusoidal portion of the distal apices 34 connected to the graft sleeve 10 traverse substantially the same path as that of the stent 23 closest to the bare stent 30. Thus, the distance d between the stent 22 and all portions of the bare stent 30 connected to the graft sleeve 10 remain constant. Such a configuration is advantageous because it maintains the symmetry of radial force of the device about the circumference of the vessel and also aids in the synchronous, simultaneous expansion of the device, thus increasing apposition of the graft material to the vessel wall to induce a proximal seal and substantially improve the proximal seal—due to increasing outward force members in contact with the vessel wall.

Inter-positioning the stents 23, 30 in phase with one another, creates an overlap, i.e., the apices 34 of the bare stent 30 are positioned within the troughs of the stent 23. A further advantage of such a configuration is that the overlap provides twice as many points of contact between the proximal opening of the graft 10 and the vessel in which the stent graft 1 is implanted. The additional apposition points keep the proximal opening of the graft sleeve 10 open against the vessel wall, which substantially reduces the potential for endoleaks. In addition, the overlap of the stents 23, 30 increases the radial load or resistance to compression, which functionally increases fixation and reduces the potential for device migration.

In contrast to the distal apices 34 of the bare stent 30, the radius of curvature β of the proximal apices 32 (those apices that are not sewn into the graft sleeve 10) is significantly larger than the radius of curvature α of the distal apices 34. A preferred configuration for the bare stent apices has a radius approximately equal to 1.5 mm for the proximal apices 32 and approximately equal to 0.5 mm for the distal apices 34. Such a configuration substantially prevents perforation of the blood vessel by the proximal apices 32, or, at a minimum, makes is much less likely for the bare stent 30 to perforate the vessel because of the less-sharp curvature of the proximal apices 32.

The bare stent 30 also has an amplitude greater than the other stents 20. Preferably, the peak-to-peak amplitude of the stents 20 is approximately 1.3 cm to 1.5 cm, whereas the peak-to-peak amplitude of the bare stent 30 is approximately 2.5 cm to 4.0 cm. Accordingly, the force exerted by the bare stent 30 on the inner wall of the aorta (due to the bare stent 30 expanding to its native position) is spread over a larger surface area. Thus, the bare stent 30 of the present invention presents a less traumatic radial stress to the interior of the vessel wall—a characteristic that, while less per square mm than an individual one of the stents 20 would be, is sufficient, nonetheless, to retain the proximal end 12 in position. Simultaneously, the taller configuration of the bare stent 30 guides the proximal opening of the stent graft in a more "squared-off" manner. Thus, the proximal opening of the stent graft is more aligned with the natural curvature of the vessel in the area of the proximal opening.

As set forth above, because the vessel moves constantly, and due to the constantly changing pressure imparted by blood flow, any stent graft placed in the vessel has the natural tendency to migrate downstream. This is especially true when the stent graft 1 has graft sleeve segments 18 with lengths defined by the separation of the stents on either end of the segment 18, giving the stent graft 1 an accordion, concertina, or caterpillar-like shape. When such a shape is pulsating with the vessel and while hemodynamic pressure is imparted in a pulsating manner along the stent graft from the proximal end 12 to the downstream distal end 14, the stent graft 1 has a tendency to migrate downstream in the vessel. It is desired to have such motion be entirely prohibited.

Support along a longitudinal extent of the graft sleeve 10 assists in preventing such movement. Accordingly, as set forth above, prior art stent grafts have provided longitudinal rods extending in a straight line from one stent to another.

The present invention, however, provides a longitudinal, spiraling/helical support member 40 that, while extending relatively parallel to the longitudinal axis 11 of the graft sleeve 10, is not aligned substantially parallel to a longitudinal extent of the entirety of the stent graft 1 as done in the prior art. "Relatively parallel" is referred to herein as an extent that is more along the longitudinal axis 11 of the stent graft 1 than along an axis perpendicular thereto.

Specifically, the longitudinal support member 40 has a somewhat S-turn shape, in that, a proximal portion 42 is relatively parallel to the axis 11 of the graft sleeve 10 at a first degree 41 (being defined as a degree of the 360 degrees of the circumference of the graft sleeve 10), and a distal portion 44 is, also, relatively parallel to the axis 11 of the tube graft, but at a different second degree 43 on the circumference of the graft sleeve 10. The difference between the first and second degrees 41, 43 is dependent upon the length L of the graft sleeve 10. For an approximately 20 cm (approx. 8") graft sleeve, for example, the second degree 43 is between 80 and 110 degrees away from the first degree 41, in particular, approximately 90 degrees away. In comparison, for an approximately 9 cm (approx. 3.5") graft sleeve, the second degree 43 is between 30 and 60 degrees away from the first degree 41, in particular, approximately 45 degrees away. As set forth below, the distance between the first and second degrees 41, 43 is also dependent upon the curvature and the kind of curvature that the stent graft 1 will be exposed to when in vivo.

The longitudinal support member 40 has a curved intermediate portion 46 between the proximal and distal portions 42, 44. By using the word "portion" it is not intended to mean that the rod is in three separate parts (of course, in a particular configuration, a multi-part embodiment is possible). A preferred embodiment of the longitudinal support member 40 is a single, one-piece rod made of stainless steel, cobalt chrome, nitinol, or polymeric material that is shaped as a fully curved helix 42, 44, 46 without any straight portion. In an alternative stent graft embodiment, the proximal and distal portions 42, 44 can be substantially parallel to the axis 11 of the stent graft 1 and the central portion 46 can be helically curved.

One way to describe the preferred curvature embodiment of the longitudinal support member 40 can be using an analogy of asymptotes. If there are two asymptotes extending parallel to the longitudinal axis 11 of the graft sleeve 10 at the first and second degrees 41, 43 on the graft sleeve 10, then the proximal portion 42 can be on the first degree 41 or extend approximately asymptotically to the first degree 41 and the distal portion 44 can be on the second degree 43 or extend approximately asymptotically to the second degree 43. Because the longitudinal support member 40 is one piece in a preferred embodiment, the curved portion 46 follows the natural curve formed by placing the proximal and distal portions 42, 44 as set forth herein.

In such a position, the curved longitudinal support member 40 has a centerline 45 (parallel to the longitudinal axis 11 of the graft sleeve 10 halfway between the first and second degrees 41, 43 on the graft sleeve 10). In this embodiment, therefore, the curved portion intersects the centerline 45 at approximately 20 to 40 degrees in magnitude, preferably at approximately 30 to 35 degrees.

Another way to describe the curvature of the longitudinal support member can be with respect to the centerline 45. The portion of the longitudinal support member 40 between the first degree 41 and the centerline 45 is approximately a mirror image of the portion of the longitudinal support member 40 between the second degree 43 and the centerline 45, but rotated one-hundred eighty degrees (180°) around an axis orthogonal to the centerline 45. Such symmetry can be referred to herein as "reverse-mirror symmetrical."

The longitudinal support member 40 is, preferably, sewn to the graft sleeve 10 in the same way as the stents 20. However, the longitudinal support member 40 is not sewn directly to any of the stents 20 in the proximal portions of the graft. In other words, the longitudinal support member 40 is independent of the proximal skeleton formed by the stents 20. Such a configuration is advantageous because an independent proximal end creates a gimbal that endows the stent graft with additional flexibility. Specifically, the gimbaled proximal end allows the proximal end to align better to the proximal point of apposition, thus reducing the chance for endoleak. The additional independence from the longitudinal support member allows the proximal fixation point to be independent from the distal section that is undergoing related motion due to the physiological motion of pulsatile flow of blood. Also in a preferred embodiment, the longitudinal support member 40 is pre-formed in the desired spiral/helical shape (counter-clockwise from proximal to distal), before being attached to the graft sleeve 10.

Because vessels receiving the stent graft 1 are not typically straight (especially the aortic arch), the final implanted position of the stent graft 1 will, most likely, be curved in some way. In prior art stent grafts (which only provide longitudinally parallel support rods), there exist, inherently, a force that urges the rod, and, thereby, the entire stent graft, to the straightened, natural shape of the rod. This force is disadvantageous for stent grafts that are to be installed in an at least partly curved manner.

The curved shape of the longitudinal support member 40 according to the present invention eliminates at least a majority, or substantially all, of this disadvantage because the longitudinal support member's 40 natural shape is curved. Therefore, the support member 40 imparts less of a force, or none at all, to straighten the longitudinal support member 40, and, thereby, move the implanted stent graft in an undesirable way. At the same time, the curved longitudinal support member 40 negates the effect of the latent kinetic force residing in the aortic wall that is generated by the propagation of the pulse wave and systolic blood pressure in the cardiac cycle, which is, then, released during diastole. As set forth in more detail below, the delivery system of the present invention automatically aligns the stent graft 1 to the most optimal position while traversing the curved vessel in which it is to be implanted, specifically, the longitudinal support member 40 is placed substantially at the superior longitudinal surface line of the curved aorta (with respect to anatomical position).

In a preferred embodiment, the longitudinal support member 40 can be curved in a patient-customized way to accommodate the anticipated curve of the actual vessel in which the graft will be implanted. Thus, the distance between the first and second degrees 41, 43 will be dependent upon the curvature and the kind of curvature that the stent graft 1 will be exposed to when in vivo. As such, when implanted, the curved longitudinal support member 40 will, actually, exhibit an opposite force against any environment that would alter its conformance to the shape of its resident vessel's existing course(es).

Preferably, the support member 40 is sewn, in a similar manner as the stents 20, on the outside surface 16 of the graft sleeve 10.

In prior art support rods, the ends thereof are merely a terminating end of a steel or nitinol rod and are, therefore, sharp. Even though these ends are sewn to the tube graft in the prior art, the possibility of tearing the vessel wall still exists. It is, therefore, desirable to not provide the support rod with sharp ends that could puncture the vessel in which the stent graft is placed.

The two ends of the longitudinal support member 40 of the present invention do not end abruptly. Instead, each end of the longitudinal support member loops 47 back upon itself such that the end of the longitudinal support member along the axis of the stent graft is not sharp and, instead, presents an exterior of a circular or oval shape when viewed from the ends 12, 14 of the graft sleeve 10. Such a configuration substantially prevents the possibility of tearing the vessel wall and also provides additional longitudinal support at the oval shape by having two longitudinally extending sides of the oval 47.

In addition, in another embodiment, the end of the longitudinal support member may be connected to the second proximal stent 28 and to the most distal stent. This configuration would allow the longitudinal support member to be affixed to stent 28 (see FIG. 1) and the most distal stent for support while still allowing for the gimbaled feature of the proximal end of the stent graft to be maintained.

A significant feature of the longitudinal support member 40 is that the ends of the longitudinal support member 40 may not extend all the way to the two ends 12, 14 of the graft sleeve 10. Instead, the longitudinal support member 40 terminates at or prior to the second-to-last stent 28 at the proximal end 12, and, if desired, prior to the second-to-last stent 28' at the distal end 14 of the graft sleeve 10. Such an ending configuration (whether proximal only or both proximal and distal) is chosen for a particular reason—when the longitudinal support member 40 ends before either of the planes defined by cross-sectional lines 52, 52', the sleeve 10 and the stents 20 connected thereto respectively form gimbaled portions 50, 50'. In other words, when a grasping force acting upon the gimbaled ends 50, 50' moves or pivots the cross-sectional plane defining each end opening of the graft sleeve 10 about the longitudinal axis 11 starting from the planes defined by the cross-sectional lines 52, 52', then the moving portions 50, 50' can be oriented at any angle γ about the center of the circular opening in all directions (360 degrees), as shown in FIG. 8. The natural gimbal, thus, allows the ends 50, 50' to be inclined in any radial direction away from the longitudinal axis 11.

Among other things, the gimbaled ends 50, 50' allow each end opening to dynamically align naturally to the curve of the vessel in which it is implanted. A significant advantage of the gimbaled ends 50, 50' is that they limit propagation of the forces acting upon the separate parts. Specifically, a force that, previously, would act upon the entirety of the stent graft 1, in other words, both the end portions 50, 50' and the middle portion of the stent graft 1 (i.e., between planes 52, 52'), now principally acts upon the portion in which the force occurs. For example, a force that acts only upon one of the end portions 50, 50' substantially does not propagate into the middle portion of the stent graft 1 (i.e., between planes 52, 52'). More significantly, however, when a force acts upon the middle portion of the stent graft 1 (whether moving longitudinally, axially (dilation), or in a torqued manner), the ends 50, 50', because they are gimbaled, remain relatively completely aligned with the natural contours of the vessel surrounding the respective end 50, 50' and have virtually none of the force transferred thereto, which force could potentially cause the ends to grate, rub, or shift from their desired fixed position in the vessel. Accordingly, the stent graft ends 50, 50' remain fixed in the implanted position and extend the seating life of the stent graft 1.

Another advantage of the longitudinal support member 40 is that it increases the columnar strength of the graft stent 1. Specifically, the material of the graft sleeve can be compressed easily along the longitudinal axis 11, a property that remains true even with the presence of the stents 20 so long as the stents 20 are attached to the graft sleeve 10 with a spacing between the distal apices 24 of one stent 20 and the proximal apices 22 of the next adjacent stent 20. This is especially true for the amount of force imparted by the flow of blood along the extent of the longitudinal axis 11. However, with the longitudinal support member 40 attached according to the present invention, longitudinal strength of the stent graft 1 increases to overcome the longitudinal forces imparted by blood flow.

Another benefit imparted by having such increased longitudinal strength is that the stent graft 1 is further prevented from migrating in the vessel because the tube graft is not compressing and expanding in an accordion-like manner—movement that would, inherently, cause graft migration.

A further measure for preventing migration of the stent graft 1 is to equip at least one of any of the individual stents 20, 30 or the longitudinal support member 40 with protuberances 60, such as barbs or hooks (FIG. 3). See, e.g., United States Patent Publication 2002/0052660 to Greenhalgh. In the preferred embodiment of the present invention, the stents 20, 30 are secured to the outer circumferential surface 16 of the graft sleeve 10. Accordingly, if the stents 20 (or connected portions of stent 30) have protuberances 60 protruding outwardly, then such features would catch the interior wall of the vessel and add to the prevention of stent graft 1 migration. Such an embodiment can be preferred for aneurysms but is not preferred for the fragile characteristics of dissections because such protuberances 60 can excoriate the inner layer(s) of the vessel and cause leaks between layers, for example.

As shown in FIG. 9, the stent graft 1 is not limited to a single graft sleeve 10. Instead, the entire stent graft can be a first stent graft 100 having all of the features of the stent graft 1 described above and a second stent graft 200 that, instead of having a circular extreme proximal end 12, as set forth above, has a proximal end 212 with a shape following the contour of the most proximal stent 220 and is slightly larger in circumference than the distal circumference of the first stent graft 100. Therefore, an insertion of the proximal end 212 of the second stent graft 200 into the distal end 114 of the first stent graft 100 results, in total, in a two-part stent graft. Because blood flows from the proximal end 112 of the first stent graft 100 to the distal end 214 of the second stent graft 200, it is preferable to have the first stent graft 100 fit inside the second stent graft 200 to prevent blood from leaking out therebetween. This configuration can be achieved by implanting the devices in reverse order (first implant graft 200 and, then, implant graft 100. Each of the stent grafts 100, 200 can have its own longitudinal support member 40 as needed.

It is not significant if the stent apices of the distal-most stent of the first stent graft 100 are not aligned with the stent apices of the proximal-most stent 220 of the second stent graft 200. What is important is the amount of junctional overlap between the two grafts 100, 200.

Delivery System

As set forth above, the prior art includes many different systems for endoluminally delivering a prosthesis, in particular, a stent graft, to a vessel. Many of the delivery systems have similar parts and most are guided along a guidewire that is inserted, typically, through an insertion into the femoral artery near a patient's groin prior to use of the delivery system. To prevent puncture of the arteries leading to and including the aorta, the delivery system is coaxially connected to the guidewire and tracks the course of the guidewire up to the aorta. The parts of the delivery system that will track over the wire are, therefore, sized to have an outside diameter smaller than the inside diameter of the femoral artery of the patient. The delivery system components that track over the guidewire include the stent graft and are made of a series of coaxial lumens referred to as catheters and sheaths. The stent graft is constrained, typically, by an outer catheter, requiring the stent graft to be compressed to fit inside the outer catheter. Doing so makes the portion of the delivery system that constrains the stent graft very stiff, which, therefore, reduces that portion's flexibility and makes it difficult for the delivery system to track over the guidewire, especially along curved vessels such as the aortic arch. In addition, because the stent graft exerts very high radial forces on the constraining catheter due to the amount that it must be compressed to fit inside the catheter, the process of deploying the stent graft by sliding the constraining catheter off of the stent graft requires a very high amount of force, typically referred to as a deployment force. Also, the catheter has to be strong enough to constrain the graft, requiring it to be made of a rigid material. If the rigid material is bent, such as when tracking into the aortic arch, the rigid material tends to kink, making it difficult if not impossible to deploy the stent graft.

Common features of vascular prosthesis delivery systems include a tapered nose cone fixedly connected to a guidewire lumen, which has an inner diameter substantially corresponding to an outer diameter of the guidewire such that the guidewire lumen slides easily over and along the guidewire. A removable, hollow catheter covers and holds a compressed prosthesis in its hollow and the catheter is fixedly connected to the guidewire lumen. Thus, when the prosthesis is in a correct position for implantation, the physician withdraws the hollow catheter to gradually expose the self-expanding prosthesis from its proximal end towards its distal end. When the catheter has withdrawn a sufficient distance from each portion of the expanding framework of the prosthesis, the framework can expand to its native position, preferably, a position that has a diameter at least as great as the inner diameter of the vessel wall to, thereby, tightly affix the prosthesis in the vessel. When the catheter is entirely withdrawn from the prosthesis and, thereby, allows the prosthesis to expand to the diameter of the vessel, the prosthesis is fully expanded and connected endoluminally to the vessel along the entire extent of the prosthesis, e.g., to treat a dissection. When treating an aneurysm, for example, the prosthesis is in contact with the vessel's proximal and distal landing zones when completely released from the catheter. At such a point in the delivery, the delivery system can be withdrawn from the patient. The prosthesis, however, cannot be reloaded in the catheter if implantation is not optimal.

The aorta usually has a relatively straight portion in the abdominal region and in a lower part of the thoracic region. However, in the upper part of the thoracic region, the aorta is curved substantially, traversing an upside-down U-shape from the back of the heart over to the front of the heart. As explained above, prior art delivery systems are relatively hard and inflexible (the guidewire/catheter portion of the prior art delivery systems). Therefore, if the guidewire/catheter must traverse the curved portion of the aorta, it will kink as it is curved or it will press against the top portion of the aortic curve, possibly puncturing the aorta if the diseased portion is located where the guidewire/catheter is exerting its force. Such a situation must be avoided at all costs because the likelihood of patient mortality is high. The prior art does not provide any way for substantially reducing the stress on the curved portion of the aorta or for making the guidewire/catheter sufficiently flexible to traverse the curved portion without causing damage to the vessel.

The present invention, however, provides significant features not found in the prior art that assist in placing a stent graft in a curved portion of the aorta in a way that substantially reduces the stress on the curved portion of the aorta and substantially reduces the insertion forces needed to have the compressed graft traverse the curved portion of the aorta. As set forth above, the longitudinal support member 40 is preformed in a desired spiral/helical shape before being attached to the graft sleeve 10 and, in a preferred embodiment, is curved in a patient-customized way to accommodate the anticipated curve of the actual vessel in which the graft will be implanted. As such, optimal positioning of the stent graft 1 occurs when the longitudinal support member 40 is placed substantially at the superior longitudinal surface line of the curved aorta (with respect to anatomical position). Such placement can be effected in two ways. First, the stent graft 1, the support member 40, or any portion of the delivery system that is near the target site can be provided with radiopaque markers that are monitored by the physician and used to manually align the support member 40 in what is perceived as an optimal position. The success of this alignment technique, however, is dependent upon the skill of the physician. Second, the delivery system can be made to automatically align the support member 40 at the optimal position. No such system existed in the prior art. However, the delivery system of the present invention provides such an alignment device, thereby, eliminating the need for physician guesswork as to the three-dimensional rotational position of the implanted stent graft 1. This alignment device is explained in further detail below with respect to FIGS. 64 to 67.

The delivery system of the present invention also has a very simple to use handle assembly. The handle assembly takes advantage of the fact that the inside diameter of the aorta is substantially larger that the inside diameter of the femoral arteries. The present invention, accordingly, uses a two-stage approach in which, after the device is inserted in through the femoral artery and tracks up into the abdominal area of the aorta (having a larger diameter (see FIG. 19) than the femoral artery), a second stage is deployed (see FIG. 20) allowing a small amount of expansion of the stent graft while still constrained in a sheath; but this sheath, made of fabric/woven polymer or similar flexible material, is very flexible. Such a configuration gives the delivery system greater flexibility for tracking, reduces deployment forces because of the larger sheath diameter, and easily overcome kinks because the sheath is made of fabric.

To describe the delivery system of the present invention, the method for operating the delivery assembly 600 will be described first in association with FIGS. 10, 11, and 12. Thereafter, the individual components will be described to allow a better understanding of how each step in the process is effected for delivering the stent graft 1 to any portion of the aorta 700 (see FIGS. 19 to 24), in particular, the curved portion 710 of the aorta.

Initially, the distal end 14 of the stent graft 1 is compressed and placed into a hollow, cup-shaped, or tubular-shaped graft holding device, in particular, the distal sleeve 644 (see, e.g., FIG. 25). At this point, it is noted that the convention for indicating direction with respect to delivery systems is opposite that of the convention for indicating direction with respect to stent grafts. Therefore, the proximal direction of the delivery system is that portion closest to the user/physician employing the system and the distal direction corresponds to the portion farthest away from the user/physician, i.e., towards the distal-most nose cone 632.

Figure 68:
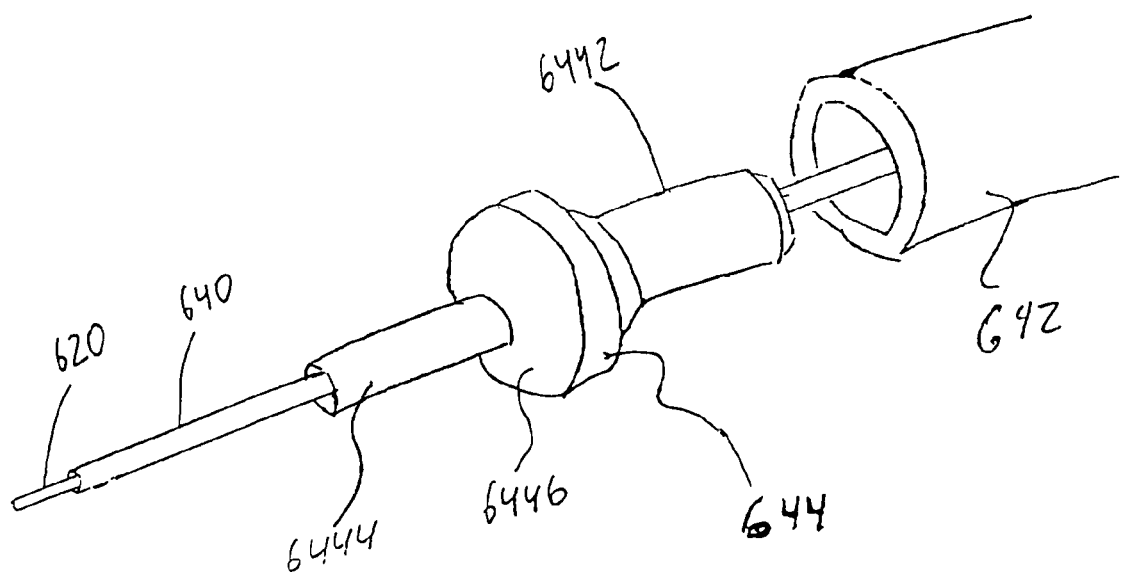
FIG. 68 is a fragmentary, enlarged, partially exploded perspective view of an alternative embodiment of a distal end of the graft push lumen of FIG. 25.

The distal sleeve 644 is fixedly connected to the distal end of the graft push lumen 642, which lumen 642 provides an end face for the distal end 14 of the stent graft 1. Alternatively, the distal sleeve 644 can be removed entirely. In such a configuration, as shown in FIG. 12, for example, the proximal taper of the inner sheath 652 can provide the measures for longitudinally holding the compressed distal end of the graft 1. If the sleeve 644 is removed, it is important to prevent the distal end 14 of the stent graft 1 from entering the space between the interior surface of the hollow sheath lumen 654 and the exterior surface of the graft push lumen 642 slidably disposed in the sheath lumen 654. Selecting a radial thickness of the space to be less than the diameter of the wire making up the stent 20, 30 (in particular, no greater than half a diameter thereof) insures reliable movement of the distal end 14 of the stent graft 1. In another alternative configuration shown in FIG. 68, the distal sleeve 644 can be a disk-shaped buttress 644 present at the distal end of the graft push lumen 642. An example configuration can provide the buttress 644 with a hollow proximal insertion peg 6442, a hollow distal stiffening tube 6444, and an intermediate buttress wall 6446. The buttress 644 is concentric to the center axis of the delivery system 600 and allows the co-axial guidewire lumen 620 and apex release lumen 640 to pass therethrough. The peg 6442 allows for easy connection to the graft push lumen 643. The stiffening tube 64 creates a transition in stiffness from the graft push lumen 642 to the apex release lumen 620 and guidewire lumen 640 and provides support to the lumen 620, 640 located therein. Such a transition in stiffness reduces any possibility of kinking at the distal end of the graft push lumen 642 and aids in transferring force from the graft push lumen 642 to the lumen therein 620, 640 when all are in a curved orientation. The buttress wall 6446 provides a flat surface that will contact the distal-end-facing side of the stent graft 1 and can be used to push the stent graft distally when the graft push lumen 642 is moved distally. The alternative configuration of the buttress 644 insures that the stent graft 1 does not become impinged within the graft push lumen 642 and the lumen therein 620, 640 when these components are moved relative to each other.

Figure 63:
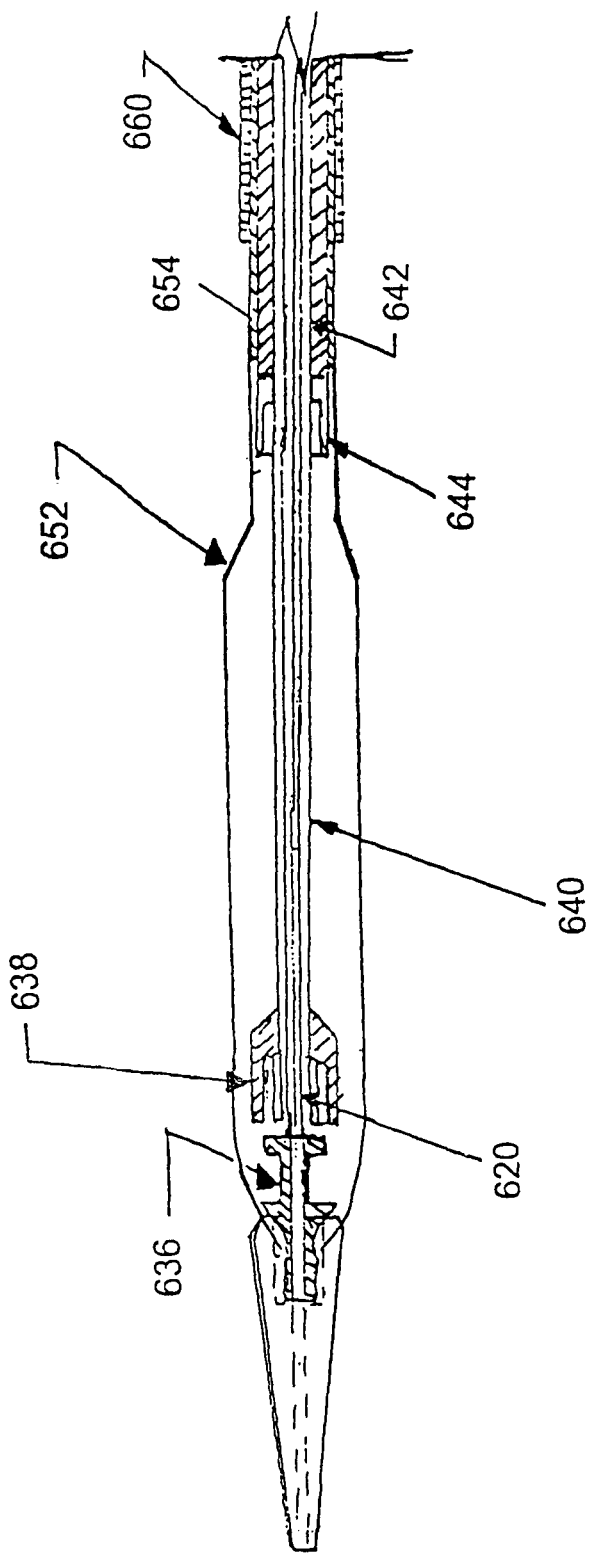
FIG. 63 is a fragmentary, cross-sectional view of the nose cone and sheath assemblies of FIG. 10.

As set forth in more detail below, each apex 32 of the bare stent 30 is, then, loaded into the apex capture device 634 so that the stent graft 1 is held at both its proximal and distal ends. The loaded distal end 14, along with the distal sleeve 644 and the graft push lumen 642, are, in turn, loaded into the inner sheath 652, thus, further compressing the entirety of the stent graft 1. The captured bare stent 30, along with the nose cone assembly 630 (including the apex capture device 634), is loaded until the proximal end of the nose cone 632 rests on the distal end of the inner sheath 652. The entire nose cone assembly 630 and sheath assembly 650 is, then, loaded proximally into the rigid outer catheter 660, further compressing the stent graft 1 (resting inside the inner sheath 652) to its fully compressed position for later insertion into a patient. See FIG. 63.

The stent graft 1 is, therefore, held both at its proximal and distal ends and, thereby, is both pushed and pulled when moving from a first position (shown in FIG. 19 and described below) to a second position (shown in FIG. 21 and described below). Specifically, pushing is accomplished by the non-illustrated interior end face of the hollow distal sleeve 644 (or the taper 653 of the inner sheath 652) and pulling is accomplished by the hold that the apex capture device 634 has on the apices 32 of the bare stent 30.

The assembly 600 according to the present invention tracks along a guidewire 610 already inserted in the patient and extending through the aorta and up to, but not into, the left ventricle of the heart 720. Therefore, a guidewire 610 is inserted through the guidewire lumen 620 starting from the nose cone assembly 630, through the sheath assembly 650, through the handle assembly 670, and through the apex release assembly 690. The guidewire 610 extends out the proximal-most end of the assembly 600. The guidewire lumen 620 is coaxial with the nose cone assembly 630, the sheath assembly 650, the handle assembly 670, and the apex release assembly 690 and is the innermost lumen of the assembly 600 immediately surrounding the guidewire 610.

Before using the delivery system assembly 600, all air must be purged from inside the assembly 600. Therefore, a liquid, such as sterile U.S.P. saline, is injected through a non-illustrated tapered luer fitting to flush the guidewire lumen at a non-illustrated purge port located near a proximal end of the guidewire lumen. Second, saline is also injected through the luer fitting 612 of the lateral purge-port (see FIG. 11), which liquid fills the entire internal co-axial space of the delivery system assembly 600. It may be necessary to manipulate the system to facilitate movement of the air to be purged to the highest point of the system.

After purging all air, the system can be threaded onto the guidewire and inserted into the patient. Because the outer catheter 660 has a predetermined length, the fixed front handle 672 can be disposed relatively close to the entry port of the femoral artery. It is noted, however, that the length of the outer catheter 660 is sized such that it will not have the fixed proximal handle 672 directly contact the entry port of the femoral artery in a patient who has the longest distance between the entry port and the thoracic/abdominal junction 742, 732 of the aorta expected in a patient (this distance is predetermined). Thus, the delivery assembly 600 of the present invention can be used with typical anatomy of the patient. Of course, the assembly 600 can be sized to any usable length.

The nose cone assembly 630 is inserted into a patient's femoral artery and follows the guidewire 610 until the nose cone 632 reaches the first position at least to a level of the celiac axis and possibly further but not into the intended stent graft deployment site, which would prevent deployment of at least the downstream end of the stent graft. The first position is shown in FIG. 19. The nose cone assembly 630 is radiopaque, whether wholly or partially, to enable the physician to determine fluoroscopically, for example, that the nose cone assembly 630 is in the first position. For example, the nose cone 632 can have a radiopaque marker 631 anywhere thereon or the nose cone 632 can be entirely radiopaque.

FIGS. 19 to 24 illustrate the catheter 660 extending approximately up to the renal arteries. However, the catheter 660 of the present invention is configured to travel up to at least the celiac axis (not shown in FIGS. 19 to 24). As used herein, the celiac axis is to be defined according to common medical terms. In a simplistic definition, the celiac axis is a plane that intersects and is parallel to a central axis of a patient's celiac at the intersection of the celiac and the aorta and, therefore, this plane is approximately orthogonal to the longitudinal axis of the abdominal/thoracic aorta at the point where the celiac intersects the aorta. Therefore, with respect to extension of the catheter 660 into the aorta, it is extended into the aorta up to but not past the intended downstream end of the implant. After arriving at this distal-most position, the distal end of the catheter 660 remains substantially steady along the longitudinal axis of the aorta until after the stent graft 1 is implanted (see FIG. 24) and the entire delivery system is to be removed from the patient. While the delivery system of the present invention can be retracted in the orientation shown in FIG. 24 except for one difference (the bare stent 32 is open and the apex release device 634 is released from compressing the bare stent 32), the preferred embodiment for removal of the catheter 660 from the aorta after implantation of the stent graft 1 occurs with reference to the condition shown in FIG. 19—where all of the interior lumens 620, 640, 642, 654 are retracted inside the catheter 660 and the nose cone 631 is in contact with the distal end of the catheter 660.

After the nose cone assembly 630 is in the first position shown in FIG. 19, the locking ring 676 is placed from its neutral position N, shown in FIG. 10, into its advancement position A, shown in FIG. 11. As will be described below, placing the locking ring 676 into its advancement position A allows both the nose cone assembly 630 and the internal sheath assembly 650 to move as one when the proximal handle 678 is moved in either the proximal or distal directions because the locking ring 676 radially locks the graft push lumen 642 to the lumens of the apex release assembly 690 (including the guidewire lumen 620 and an apex release lumen 640). The locking ring 676 is fixedly connected to a sheath lumen 654.

Before describing how various embodiments of the handle assembly 670 function, a summary of the multi-lumen connectivity relationships, throughout the neutral N, advancement A, and deployment D positions, is described.

Figure 48:
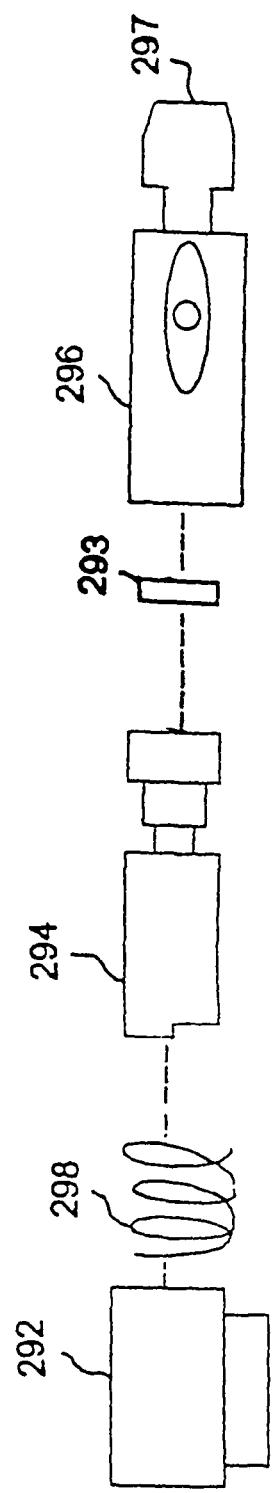
FIG. 48 is an exploded side elevational view of a portion of the handle assembly of FIG. 47.

When the locking ring is in the neutral position N shown in FIG. 10, the pusher clasp spring 298 shown in FIG. 48 and the proximal spring 606 shown in FIG. 52 are both disengaged. This allows free movement of the graft push lumen 642 with the guidewire lumen 620 and the apex release lumen 640 within the handle body 674.

When the locking ring 676 is moved into the advancement position A, shown in FIG. 11, the pusher clasp spring 298 shown in FIG. 48 is engaged and the proximal spring 606 shown in FIG. 52 is disengaged. The sheath lumen 654 (fixedly attached to the inner sheath 652) is, thereby, locked to the graft push lumen 642 (fixedly attached to the distal sleeve 644) so that, when the proximal handle 678 is moved toward the distal handle 672, both the sheath lumen 654 and the graft push lumen 642 move as one. At this point, the graft push lumen 642 is also locked to both the guidewire lumen 620 and the apex release lumen 640 (which are locked to one another through the apex release assembly 690 as set forth in more detail below). Accordingly, as the proximal handle 678 is moved to the second position, shown with dashed lines in FIG. 11, the sheath assembly 650 and the nose cone assembly 630 progress distally out of the outer catheter 660 as shown in FIGS. 20 and 21 and with dashed lines in FIG. 11.

At this point, the sheath lumen 654 needs to be withdrawn from the stent graft 1 to, thereby, expose the stent graft 1 from its proximal end 12 to its distal end 14 and, ultimately, entirely off of its distal end 14. Therefore, movement of the locking ring 676 into the deployment position D will engage the proximal spring 606 shown in FIG. 52 and disengage the pusher clasp spring 298 shown in FIG. 48. Accordingly, the graft push lumen 642 along with the guidewire lumen 620 and the apex release lumen 640 are locked to the handle body 674 so as not to move with respect to the handle body 674. The sheath lumen 654 is unlocked from the graft push lumen 642.

Movement of the distal handle 678 back to the third position (proximally), therefore, pulls the sheath lumen 654 proximally, thus, proximally withdrawing the inner sheath 652 from the stent graft 1.

At this point, the delivery assembly 600 only holds the bare stent 30 of the stent graft 1. Therefore, final release of the stent graft 1 occurs by releasing the bare stent 30 from the nose cone assembly 630, which is accomplished using the apex release assembly 690 as set forth below.

In order to explain how the locking and releasing of the lumen occur as set forth above, reference is made to FIGS. 33 to 62.

Figure 44:
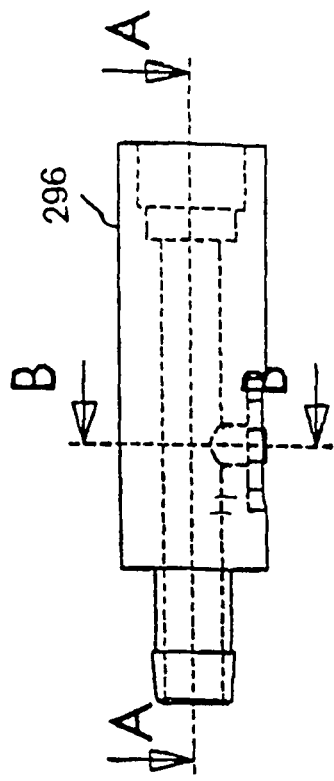
FIG. 44 is an elevational and partially hidden side view of a pusher clasp body of the handle assembly of FIG. 33.
Figure 46:
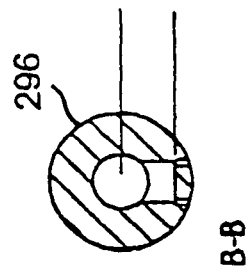
FIG. 46 is a cross-sectional view of the pusher clasp body of FIG. 44 along section line B-B.
Figure 45:
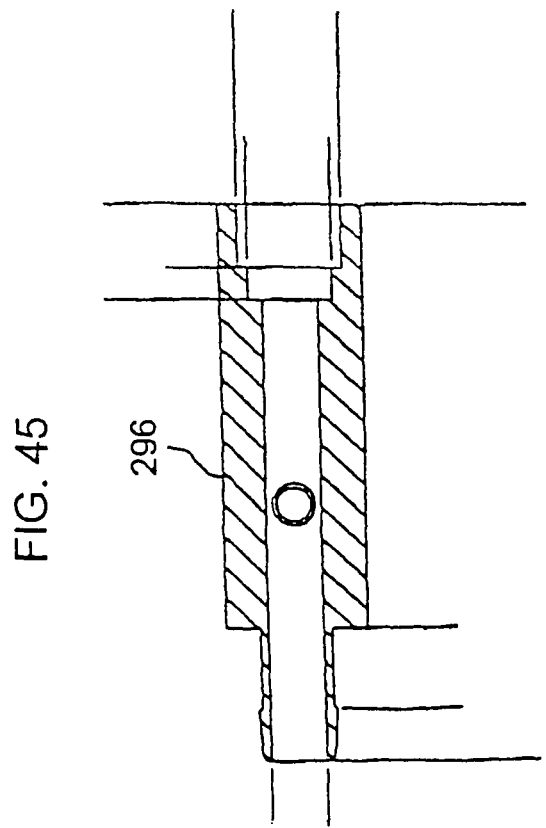
FIG. 45 is a cross-sectional view of the pusher clasp body of FIG. 44 along section line A-A.
Figure 47:
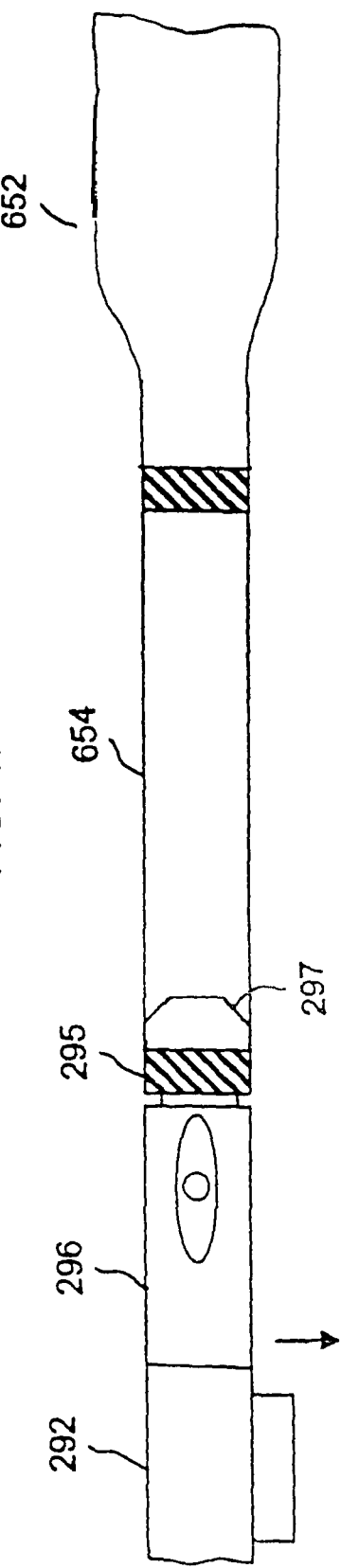
FIG. 47 is a fragmentary, side elevational view of a portion of the handle assembly of FIG. 33 with a sheath assembly according to the invention.

FIG. 33 is a cross-sectional view of the proximal handle 678 and the locking ring 676. A pusher clasp rotator 292 is disposed between a clasp sleeve 614 and the graft push lumen 642. A specific embodiment of the pusher clasp rotator 292 is illustrated in FIGS. 34 through 39. Also disposed between the clasp rotator 292 and the graft push lumen 642 is a rotator body 294, which is directly adjacent the graft push lumen 642. A specific embodiment of the rotator body 294 is illustrated in FIGS. 40 through 43. Disposed between the rotator body 294 and the sheath lumen 654 is a pusher clasp body 296, which is fixedly connected to the rotator body 294 and to the locking ring 676. A specific embodiment of the pusher clasp body 296 is illustrated in FIGS. 44 through 46. A pusher clasp spring 298 operatively connects the pusher clasp rotator 292 to the rotator body 294 (and, thereby, the pusher clasp body 296).

Figure 49:
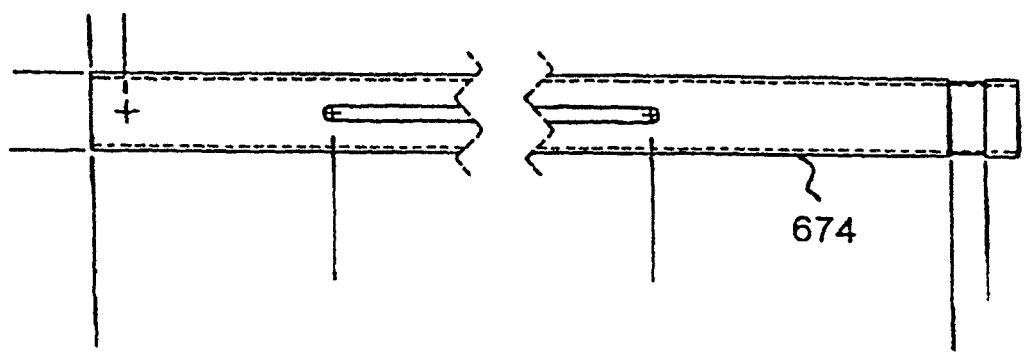
FIG. 49 is a fragmentary elevational and partially hidden side view of a handle body of the handle assembly of FIG. 33.
Figure 56:
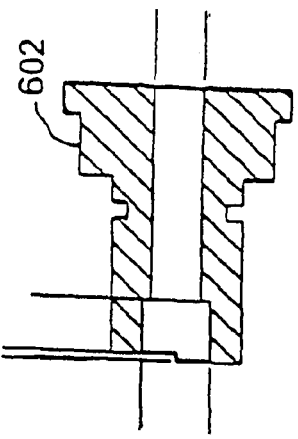
FIG. 56 is a cross-sectional view of the clasp body of FIG. 55 along section line A-A.
Figure 54:
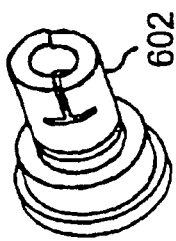
FIG. 54 is perspective view of a clasp body of the second embodiment of the handle assembly.
Figure 58:
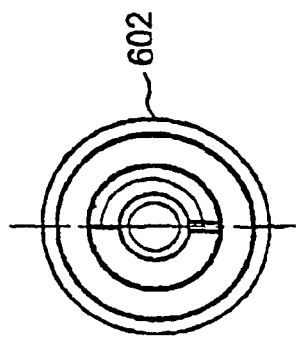
FIG. 58 is a plan view of the clasp body of FIG. 57 viewed from section line B-B.
Figure 55:
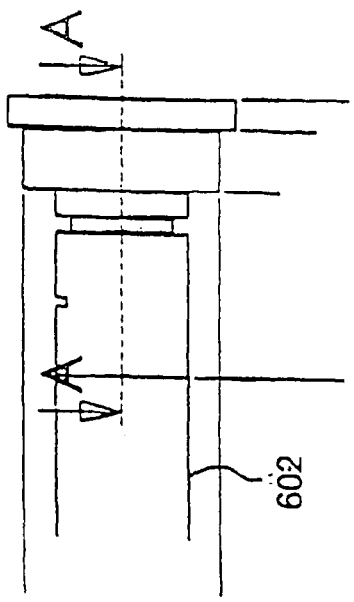
FIG. 55 is an elevational side view of the clasp body of FIG. 54.
Figure 57:
FIG. 57 is a plan view of the clasp body of FIG. 54.

An exploded view of these components is presented in FIG. 48, where an O-ring 293 is disposed between the rotator body 294 and the pusher clasp body 296. As shown in the plan view of FIG. 47, a crimp ring 295 connects the sheath lumen 654 to the distal projection 297 of the pusher clasp body 296. A hollow handle body 674 (see FIGS. 10, 11, and 33), on which the proximal handle 678 and the locking ring 676 are slidably mounted, holds the pusher clasp rotator 292, the rotator body 294, the pusher clasp body 296, and the pusher clasp spring 298 therein. This entire assembly is rotationally mounted to the distal handle 672 for rotating the stent graft 1 into position (see FIGS. 23 and 24 and the explanations thereof below). A specific embodiment of the handle body 674 is illustrated in FIG. 49.

Figure 36:
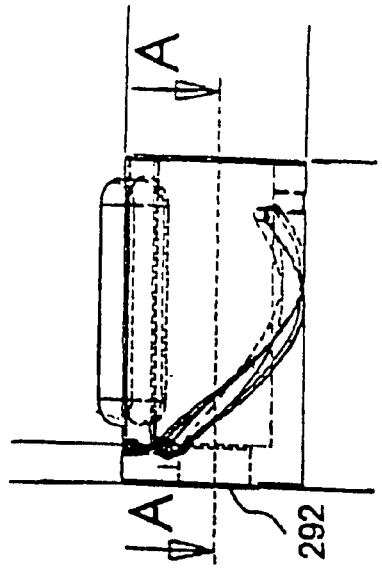
FIG. 36 is a plan and partially hidden view of the pusher clasp rotator of FIG. 34 with a helix groove for a first embodiment of the handle assembly of FIGS. 10, 11, and 18.
Figure 39:
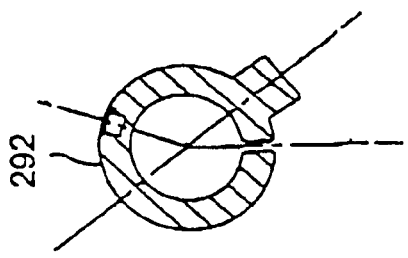
FIG. 39 is a cross-sectional view of the pusher clasp rotator of FIG. 38 along section line B-B.
Figure 35:
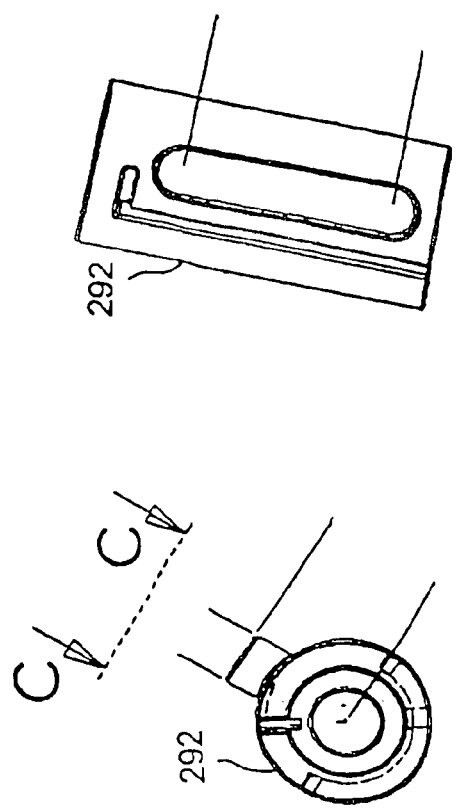
FIG. 35 is a plan view of the pusher clasp rotator of FIG. 34 viewed along line C-C.
Figure 38:
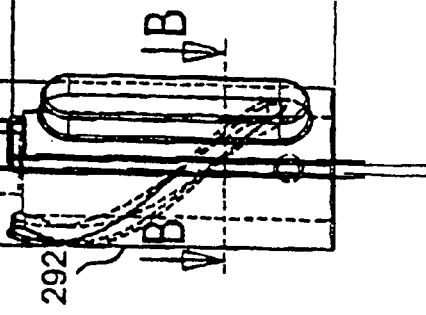
FIG. 38 is a plan and partially hidden view of the pusher clasp rotator of FIG. 36.
Figure 34:
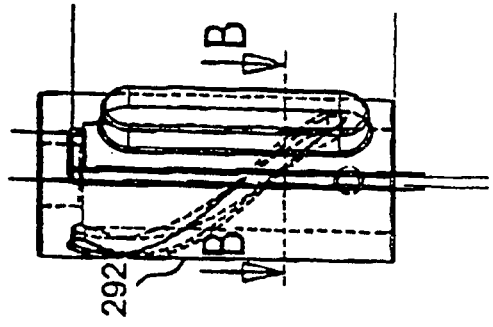
FIG. 34 is a cross-sectional view of a pusher clasp rotator of the handle assembly of FIG. 33.
Figure 37:
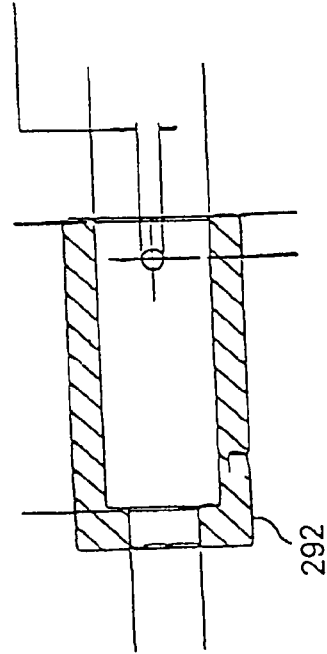
FIG. 37 is a cross-sectional view of the pusher clasp rotator of FIG. 36 along section line A-A.

A setscrew 679 extends from the proximal handle 678 to contact a longitudinally helixed groove in the pusher clasp rotator 292 (shown in FIGS. 36 and 38). Thus, when moving the proximal handle 678 proximally or distally, the pusher clasp rotator 292 rotates clockwise or counter-clockwise.

An alternative embodiment of the locking ring 676 is shown in FIG. 50 et seq., which is the preferred embodiment because, instead of applying a longitudinal movement to rotate the pusher clasp spring 298 through the cam/follower feature of the proximal handle 678 and pusher clasp rotator 292, a rotating locking knob 582 is located at the proximal end of the handle body 674. The knob 582 has three positions that are clearly shown in FIG. 51: a neutral position N, an advancement position A, and a deployment position D. The functions of these positions N, A, D correspond to the positions N, A, D of the locking ring 676 and the proximal handle 678 as set forth above.

In the alternative embodiment, a setscrew 584 is threaded into the clasp sleeve 614 through a slot 675 in the handle body 674 and through a slot 583 in the knob 582 to engage the locking knob 582. Because of the x-axis orientation of the slot 583 in the knob 582 and the y-axis orientation of the slot 675 in the handle body 674, when the knob 582 is slid over the end of the handle body 674 and the setscrew 584 is screwed into the clasp sleeve 614, the knob 582 is connected fixedly to the handle body 674. When the locking knob 582 is, thereafter, rotated between the neutral N, advancement A, and deployment D positions, the clasp sleeve 614 rotates to actuate the spring lock (see FIGS. 48 and 52).

A setscrew 586, shown in FIG. 53, engages a groove 605 in the proximal clasp assembly 604 to connect the proximal clasp assembly 604 to the clasp sleeve 614 but allows the clasp sleeve 614 to rotate around the clasp body 602. The clasp sleeve 614 is shown in FIGS. 50 and 53 and, in particular, in FIGS. 59 to 62. The proximal clasp assembly 604 of FIG. 53 is more clearly shown in the exploded view of FIG. 52. The proximal clasp assembly 604 is made of the components including a proximal spring 606, a locking washer 608, a fastener 603 (in particular, a screw fitting into internal threads of the proximal clasp body 602), and a proximal clasp body 602. The proximal clasp body 602 is shown, in particular, in FIGS. 54 through 58. The proximal clasp assembly 604 is connected fixedly to the handle body 674, preferably, with a screw 585 shown in FIG. 50 and hidden from view in FIG. 51 under knob 582.

The handle body 674 has a position pin 592 for engaging in position openings at the distal end of the locking knob 582. The position pin 592 can be a setscrew that only engages the handle body 674. When the locking knob 582 is pulled slightly proximally, therefore, the knob can be rotated clockwise or counter-clockwise to place the pin 592 into the position openings corresponding to the advancement A, neutral N, and deployment D positions.

As shown in FIG. 18, to begin deployment of the stent graft 1, the user/physician grasps both the distal handle 672 and the proximal handle 678 and slides the proximal handle 678 towards the distal handle 672 in the direction indicated by arrow A. This movement, as shown in FIGS. 19 to 21, causes the flexible inner sheath 652, holding the compressed stent graft 1 therein, to emerge progressively from inside the outer catheter 660. Such a process allows the stent graft 1, while constrained by the inner sheath 652, to expand to a larger diameter shown in FIG. 12, this diameter being substantially larger than the inner diameter of the outer catheter 660 but smaller than the inner diameter of the vessel in which it is to be inserted. Preferably, the outer catheter 660 is made of a polymer (co-extrusions or teflons) and the inner sheath 652 is made of a material, such as a fabric/woven polymer or other similar material. Therefore, the inner sheath 652 is substantially more flexible than the outer catheter 660.

It is noted, at this point, that the inner sheath 652 contains a taper 653 at its proximal end, distal to the sheath's 652 connection to the sheath lumen 654 (at which connection the inner sheath 652 has a similar diameter to the distal sleeve 644 and works in conjunction with the distal sleeve 644 to capture the distal end 14 of the stent graft 1. The taper 653 provides a transition that substantially prevents any kinking of the outer catheter 660 when the stent graft 1 is loaded into the delivery assembly 600 (as in the position illustrated in FIGS. 10 and 11) and, also, when the outer catheter 660 is navigating through the femoral and iliac vessels. One specific embodiment of the sheath lumen 654 has a length between approximately 30 and approximately 40 inches, in particular, 36 inches, an outer diameter of between approximately 0.20 and approximately 0.25 inches, in particular 0.238 inches, and an inner diameter between approximately 0.18 and approximately 0.22 inches, in particular, 0.206 inches.

When the proximal handle 678 is moved towards its distal position, shown by the dashed lines in FIG. 11, the nose cone assembly 630 and the sheath assembly 650 move towards a second position where the sheath assembly 650 is entirely out of the outer catheter 660 as shown in FIGS. 20 and 21. As can be seen most particularly in FIGS. 20 and 21, as the nose cone assembly 630 and the sheath assembly 650 are emerging out of the outer catheter 660, they are traversing the curved portion 710 of the descending aorta. The tracking is accomplished visually by viewing radiopaque markers on various portions of the delivery system and/or the stent graft 1 with fluoroscopic measures. Such markers will be described in further detail below. The delivery system can be made visible, for example, by the nose cone 630 being radiopaque or containing radiopaque materials.

It is noted that if the harder outer catheter 660 was to have been moved through the curved portion 710 of the aorta 700, there is a great risk of puncturing the aorta 700, and, particularly, a diseased portion 744 of the proximal descending aorta 710 because the outer catheter 660 is not as flexible as the inner sheath 652. But, because the inner sheath 652 is so flexible, the nose cone assembly 630 and the sheath assembly 650 can be extended easily into the curved portion 710 of the aorta 700 with much less force on the handle than previously needed with prior art systems while, at the same time, imparting harmless forces to the intraluminal surface of the curved aorta 710 due to the flexibility of the inner sheath 652.

At the second position shown in FIG. 21, the user/physician, using fluoroscopic tracking of radiopaque markers (e.g., marker 631) on any portion of the nose cone or on the stent graft 1 and/or sheath assemblies 630, 650, for example, makes sure that the proximal end 112 of the stent graft 1 is in the correct longitudinal position proximal to the diseased portion 744 of the aorta 700. Because the entire inserted assembly 630, 650 in the aorta 700 is still rotationally connected to the portion of the handle assembly 670 except for the distal handle 672 (distal handle 672 is connected with the outer sheath 660 and rotates independently of the remainder of the handle assembly 670), the physician can rotate the entire inserted assembly 630, 650 clockwise or counterclockwise (indicated in FIG. 20 by arrow B) merely by rotating the proximal handle 678 in the desired direction. Such a feature is extremely advantageous because the non-rotation of the outer catheter 660 while the inner sheath 652 is rotating eliminates stress on the femoral and iliac arteries when the rotation of the inner sheath 652 is needed and performed.

Accordingly, the stent graft 1 can be pre-aligned by the physician to place the stent graft 1 in the optimal circumferential position. FIG. 23 illustrates the longitudinal support member 40 not in the correct superior position and FIG. 24 illustrates the longitudinal support member 40 in the correct superior position. The optimal superior surface position is, preferably, near the longest superior longitudinal line along the circumference of the curved portion of the aorta as shown in FIGS. 23 and 24. As set forth above, when the longitudinal support member 40 extends along the superior longitudinal line of the curved aorta, the longitudinal support member 40 substantially eliminates any possibility of forming a kink in the inferior radial curve of the stent graft 1 during use and also allows transmission of longitudinal forces exerted along the inside lumen of the stent graft 1 to the entire longitudinal extent of the stent graft 1, thereby allowing the entire outer surface of the stent graft 1 to resist longitudinal migration. Because of the predefined curvature of the support member 40, the support member 40 cannot align exactly and entirely along the superior longitudinal line of the curved aorta. Accordingly, an optimal superior surface position of the support member 40 places as much of the central portion of the support member 40 (between the two ends 47 thereof) as possible close to the superior longitudinal line of the curved aorta. A particularly desirable implantation position has the superior longitudinal line of the curved aorta intersecting the proximal half of the support member 40—the proximal half being defined as that portion of the support member 40 located between the centerline 45 and the proximal support member loop 47. However, for adequate implantation purposes, the centerline 45 of the support member 40 can be as much as seventy circumferential degrees away from either side of the superior longitudinal line of the curved aorta. Adequate implantation can mean that the stent graft 1 is at least approximately aligned. When implantation occurs with the stent graft 1 being less than seventy degrees, for example, less than forty degrees, away from either side of the superior longitudinal line of the curved aorta, then it is substantially aligned.

In prior art stent grafts and stent graft delivery systems, the stent graft is, typically, provided with symmetrically-shaped radiopaque markers along one longitudinal line and at least one other symmetrically-shaped radiopaque marker disposed along another longitudinal line on the opposite side (one-hundred eighty degrees (180°)) of the stent graft. Thus, using two-dimensional fluoroscopic techniques, the only way to determine if the stent graft is in the correct rotational position is by having the user/physician rotate the stent graft in both directions until it is determined that the first longitudinal line is superior and the other longitudinal line is anterior. Such a procedure requires more work by the physician and is, therefore, undesirable.

According to a preferred embodiment of the invention illustrated in FIGS. 27 and 28, unique radiopaque markers 232, 234 are positioned on the stent graft 1 to assist the user/physician in correctly positioning the longitudinal support member 40 in the correct aortic superior surface position with only one directional rotation, which corresponds to the minimal rotation needed to place the stent graft 1 in the rotationally correct position.

Specifically, the stent graft 1 is provided with a pair of symmetrically shaped but diametrically opposed markers 232, 234 indicating to the user/physician which direction the stent graft 1 needs to be rotated to align the longitudinal support member 40 to the superior longitudinal line of the curved aorta (with respect to anatomical position). Preferably, the markers 232, 234 are placed at the proximate end 12 of the graft sleeve 10 on opposite sides (one-hundred eighty degrees (180°)) of the graft sleeve 10.

The angular position of the markers 232, 234 on the graft sleeve 10 is determined by the position of the longitudinal support member 40. In a preferred embodiment, the support member 40 is between the two markers 232, 234. To explain such a position, if the marker 232 is at a 0 degree position on the graft sleeve 10 and the marker 234 is at a one-hundred eighty degree (180°) position, then the centerline 45 of the support member 40 is at a ninety degree position. However, an alternative position of the markers can place the marker 234 ninety degrees away from the first degree 41 (see FIG. 1). Such a positioning is dependent somewhat upon the way in which the implantation is to be viewed by the user/physician and can be varied based on other factors. Thus, the position can be rotated in any beneficial way.

Preferred ancillary equipment in endovascular placement of the stent graft 1 is a fluoroscope with a high-resolution image intensifier mounted on a freely angled C-arm. The C-arm can be portable, ceiling, or pedestal mounted. It is important that the C-arm have a complete range of motion to achieve AP to lateral projections without moving the patient or contaminating the sterile field. Capabilities of the C-arm should include: Digital Subtraction Angiography, High-resolution Angiography, and Roadmapping.

For introduction of the delivery system into the groin access arteries, the patient is, first, placed in a sterile field in a supine position. To determine the exact target area for placement of the stent graft 1, the C-arm is rotated to project the patient image into a left anterior oblique projection, which opens the radial curve of the thoracic aortic arch for optimal visualization without superimposition of structures. The degree of patient rotation will vary, but is usually 40 to 50 degrees. At this point, the C-arm is placed over the patient with the central ray of the fluoroscopic beam exactly perpendicular to the target area. Such placement allows for the markers 232, 234 to be positioned for correct placement of the stent graft 1. Failure to have the central ray of the fluoroscopic beam perpendicular to the target area can result in parallax, leading to visual distortion to the patient anatomy due to the divergence of the fluoroscopic x-ray beam, with a resultant misplacement of the stent graft 1. An angiogram is performed and the proposed stent graft landing zones are marked on the visual monitor. Once marked, neither the patient, the patient table, nor the fluoroscopic C-arm can be moved, otherwise, the reference markers become invalid. The stent graft 1 is, then, placed at the marked landing zones.

In a preferred embodiment, the markers 232, 234 are hemispherical, in other words, they have the approximate shape of a "D". This shape is chosen because it provides special, easy-to-read indicators that instantly direct the user/physician to the correct placement position for the longitudinal support member 40. FIG. 27, for example, illustrates a plan view of the markers 232, 234 when they are placed in the upper-most superior longitudinal line of the curved aorta. The correct position is indicated clearly because the two hemispheres have the flat diameters aligned on top of or immediately adjacent to one another such that a substantially complete circle is formed by the two hemispherically rounded portions of the markers 232, 234. This position is also indicated in the perspective view of FIG. 28.

Each of FIGS. 27 and 28 have been provided with examples where the markers 232, 234 are not aligned and, therefore, the stent graft 1 is not in the correct insertion position. For example, in FIG. 27, two markers 232', 234' indicate a misaligned counter-clockwise-rotated stent graft 1 when viewed from the plane 236 at the right end of the stent graft 1 of FIG. 23 looking toward the left end thereof and down the axis 11. Thus, to align the markers 232', 234' in the most efficient way possible (the shortest rotation), the user/physician sees that the distance between the two flat diameters is closer than the distance between the highest points of the hemispherical curves. Therefore, it is known that the two flat diameters must be joined together by rotating the stent graft 1 clockwise.

FIG. 28 has also been provided with two markers 232", 234" indicating a misaligned clockwise-rotated stent graft 1 when viewed from the plane 236 at the right end of the stent graft 1 of FIG. 27 looking toward the left end thereof and down the axis 11. Thus, to align the markers 232", 234" in the most efficient way possible (the shortest rotation), the user/physician sees that the distance between the highest points of the hemispherical curves is smaller than the distance between the two flat diameters. Therefore, it is known that the two flat diameters must be joined together by rotating the stent graft 1 in the direction that the highest points of the hemispherical curves point; in other words, the stent graft 1 must be rotated counter-clockwise.

A significant advantage provided by the diametrically opposed symmetric markers 232, 234 is that they can be used for migration diagnosis throughout the remaining life of a patient after the stent graft 1 has been placed inside the patient's body. If fluoroscopic or radiographic techniques are used any time after the stent graft 1 is inserted in the patient's body, and if the stent graft 1 is viewed from the same angle as it was viewed when placed therein, then the markers' 232, 234 relative positions observed should give the examining individual a very clear and instantaneous determination as to whether or not the stent graft 1 has migrated in a rotational manner.

The hemispherical shape of the markers 232, 234 are only provided as an example shape. The markers 232, 234 can be any shape that allows a user/physician to distinguish alignment and direction of rotation for alignment. For example, the markers 232, 234 can be triangular, in particular, an isosceles triangle having the single side be visibly longer or shorter than the two equal sides.

As set forth above, alignment to the optimal implantation position is dependent upon the skill of the physician(s) performing the implantation. The present invention improves upon the embodiments having longitudinal and rotational radiopaque markers 232, 234 and substantially eliminates the need for rotational markers. Specifically, it is noted that the guidewire 610 travels through a curve through the aortic arch towards the heart 720. It is, therefore, desirable to pre-shape the delivery system to match the aorta of the patient.

Figure 64:
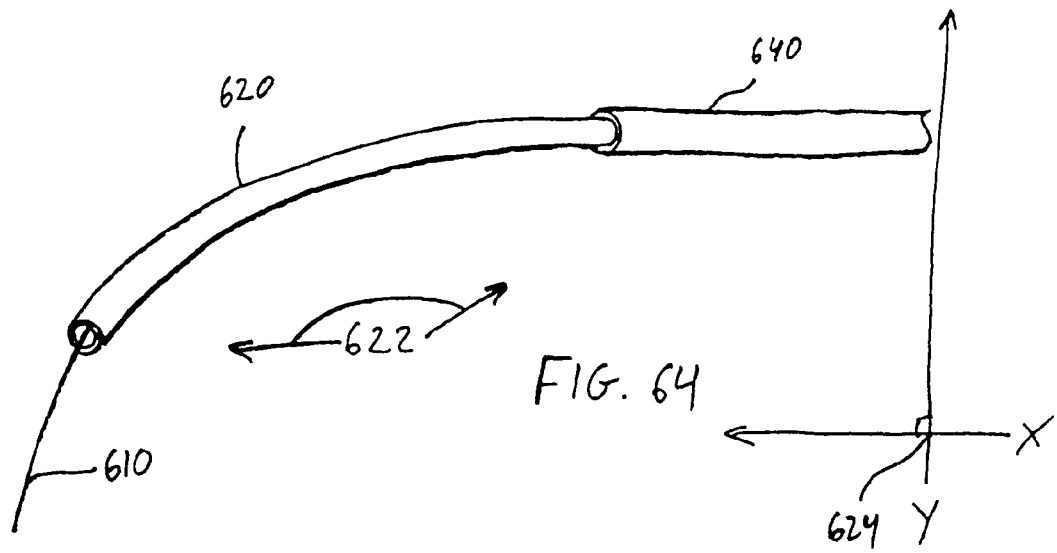
FIG. 64 is a fragmentary, perspective view of a portion of self-alignment configuration according to the invention.

The guidewire lumen 620 is formed from a metal, preferably, stainless steel. Thus, the guidewire lumen 620 can be deformed plastically into any given shape. In contrast, the apex release lumen 640 is formed from a polymer, which tends to retain its original shape and cannot plastically deform without an external force, e.g., the use of heat. Therefore, to effect the pre-shaping of the delivery assembly 600, the guidewire lumen 620, as shown in FIG. 64, is pre-shaped with a curve at a distal-most area 622 of the lumen 620. The pre-shape can be determined, for example, using the fluoroscopic pre-operative techniques described above, in which the guidewire lumen 620 can be customized to the individual patient's aortic shape. Alternatively, the guidewire lumen 620 can be pre-shaped in a standard manner that is intended to fit an average patient. Another alternative is to provide a kit that can be used to pre-shape the guidewire lumen 620 in a way that is somewhat tailored to the patient, for example, by providing a set of delivery systems 600 or a set of different guidewire lumens 620 that have different radii of curvature.

With the pre-curved guidewire lumen 620, when the nose cone 632 and inner sheath 652 exit the outer catheter 660 and begin to travel along the curved guidewire 610, the natural tendency of the pre-curved guidewire lumen 620 will be to move in a way that will best align the two curves to one another (see FIGS. 20 and 21). The primary factor preventing the guidewire lumen 620 from rotating itself to cause such an alignment is the torque generated by rotating the guidewire lumen 620 around the guidewire 610. The friction between the aorta and the device also resists rotational motion. The delivery system 600, however, is configured naturally to minimize such torque. As set forth above with respect to FIGS. 15 to 17, the guidewire lumen 620 freely rotates within the apex release lumen 640 and is only connected to the apex release lumen 640 at the proximal-most area of both lumen 620, 640. While the inner sheath 652 advances through the aortic arch, the two lumen 620, 640 are rotationally connected only at the apex release assembly 690. This means that rotation of the guidewire lumen 620 about the guidewire 610 and within the apex release lumen 640 occurs along the entire length of the guidewire lumen 620. Because the metallic guidewire lumen 620 is relatively rotationally elastic along its length, rotation of the distal-most portion (near the nose cone assembly 630) with respect to the proximal-most portion (near the apex release assembly 690) requires very little force. In other words, the torque resisting rotation of the distal-most portion to conform to the curve of the guidewire 610 is negligible. Specifically, the torque is so low that the force resisting the alignment of the guidewire lumen 620 to the guidewire 610 causes little, negligible, or no damage to the inside of the aorta, especially to a dissecting inner wall of a diseased aorta.

Due to the configuration of the delivery system 600 of the present invention, when the guidewire lumen 620 is extended from the outer catheter 660 (along with the apex release lumen 640, the stent graft 1, the inner sheath 652 as shown in FIGS. 20 and 21, for example), the pre-shape of the guidewire lumen 620 causes automatic and natural rotation of the entire distal assembly—including the stent graft 1—along its longitudinal axis. This means that the length and connectivity of the guidewire lumen 620, and the material from of which the guidewire lumen 620 is made, allow the entire distal assembly (1, 620, 630, 640, 650) to naturally rotate and align the pre-curved guidewire lumen 620 with the curve of the guidewire 610—this is true even if the guidewire lumen 620 is inserted into the aorta entirely opposite the curve of the aorta (one-hundred eighty degrees (180°)). In all circumstances, the curved guidewire lumen 620 will cause rotation of the stent graft 1 into an optimal implantation position, that is, aligning the desired portion of the support member 40 within ±70 degrees of the superior longitudinal line of the curved aorta. Further, the torque forces acting against rotation of the guidewire lumen 620 will not be too high to cause damage to the aorta while carrying out the rotation.

The self-aligning feature of the invention begins with a strategic loading of the stent graft 1 in the inner sleeve 652. To describe the placement of the supporting member 40 of the stent graft 1 relative to the curve 622 of the guidewire lumen 620, an X-Y coordinate curve plane is defined and shown in FIG. 64. In particular, the guidewire lumen 620 is curved and that curve 622 defines the curve plane 624.

To insure optimal implantation, when loading the stent graft 1 into the inner sheath 652, a desired point on the supporting member 40 between the centerline 45 of the stent graft 1 and the proximal support member loop 47 is aligned to intersect the curve plane 624. The preferred, but not required, location of the desired point on the supporting member 40 is located forty-five (45) degrees around the circumference of the stent graft 1 shown in FIG. 1 beginning from the first degree 41 in line with the proximal support member loop 47. When the stent graft 1 is loaded in the preferred orientation, it is ready for insertion into the inner sleeve 652. During the loading process, the stent graft 1 and the guidewire lumen 620 are held constant rotationally. After such loading, the inner sleeve 652 is retracted into the outer catheter 660 and the delivery system 600 is ready for purging with saline and use with a patient.

Figure 65:
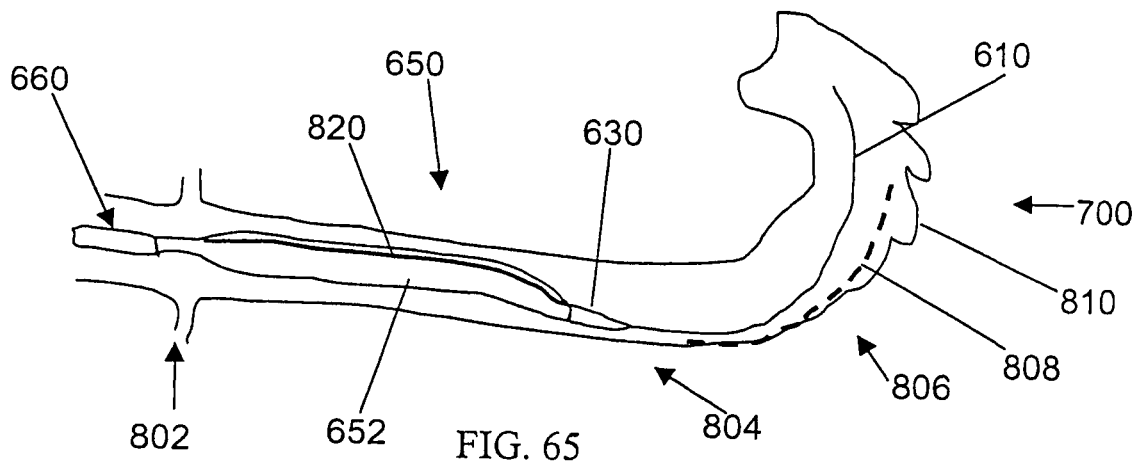
FIG. 65 is a diagrammatic, fragmentary, cross-sectional view of a distal portion of the delivery system with the self-alignment configuration according to the invention inside the descending thoracic aorta and with the self-alignment configuration in an orientation opposite a desired orientation.
Figure 66:
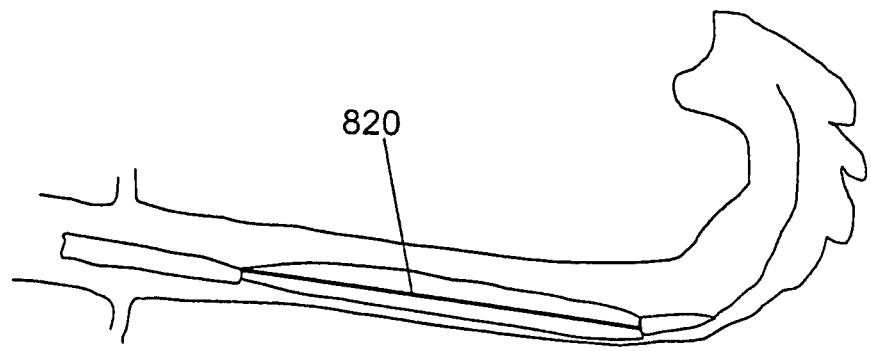
FIG. 66 is a diagrammatic, fragmentary, cross-sectional view of the distal portion of the delivery system of FIG. 65 with the self-alignment configuration partially inside the descending thoracic aorta and partially inside the aortic arch and with the self-alignment configuration in an orientation closer to the desired orientation.
Figure 67:
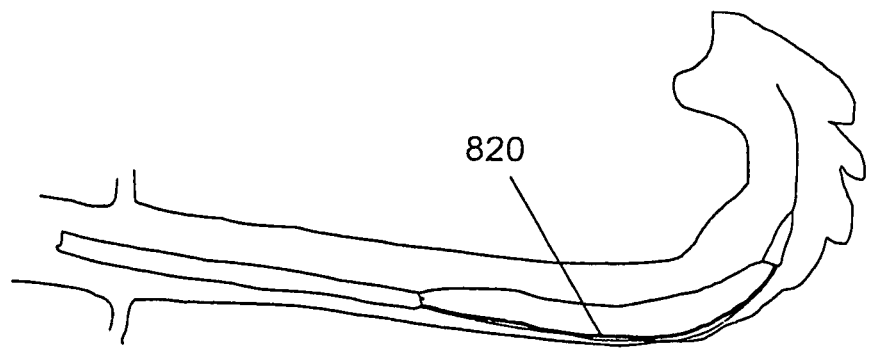
FIG. 67 is a diagrammatic, fragmentary, cross-sectional view of the distal portion of the delivery system of FIG. 65 with the self-alignment configuration primarily inside the aortic arch and with the self-alignment configuration substantially in the desired orientation.

FIGS. 65 to 67 illustrate self-alignment of the distal assembly 620, 630, 640, 650 after it is pushed out from the distal end of the outer catheter 660 (see FIGS. 20 and 21). FIG. 65 shows an aorta 700 and the distal assembly after it has traversed the iliac arteries 802 and enters the descending thoracic portion 804 of the aorta. The nose cone assembly 630 is positioned just before the aortic arch 806 and the stent graft 1 is contained within the inner sheath 652. A reference line 820 is placed on the stent graft 1 at a longitudinal line of the stent graft 1 that is intended to align with the superior longitudinal line 808 (indicated with dashes) of the aortic arch 806. In FIG. 65, the reference line 820 also lies on the curved plane 624 defined by the pre-curved guidewire lumen 620. As can be clearly seen from FIG. 65, the reference line 820 is positioned almost on or on the inferior longitudinal line of the curved aorta—thus, the stent graft 1 is one-hundred eighty degrees (180°) out of alignment. FIG. 66 shows the nose cone assembly 630 fully in the aortic arch 806 and the inner sleeve 652 at the entrance of the aortic arch 806. With the self-aligning configuration of the pre-curved guidewire lumen 620, movement of the distal assembly from the position shown in FIG. 65 to the position shown in FIG. 66 causes a rotation of the reference line 820 almost ninety degrees (90°) clockwise (with respect to a view looking upward within the descending aorta) towards the superior longitudinal line 808. In FIG. 67, the nose cone assembly 630 has reached, approximately, the left subclavian artery 810. Rotational movement of the distal assembly is, now, complete, with the reference line 820 almost aligned with the superior longitudinal line 808 of the aortic arch 806. From the views of FIGS. 65 to 67, also shown is the fact that the pre-curved guidewire lumen 620 has not caused any portion of the inner sleeve 652 to push against the inner surface of the aortic arch 806 with force—force that might exacerbate an aortic dissection.

It is noted that the guidewire lumen 620 need not be rotationally fixedly connected to the apex release lumen 640 when the apex release assembly 690 is in the locked position shown in FIGS. 15 and 16. Instead, a non-illustrated, freely rotatable coupling can be interposed anywhere along the guidewire lumen 620 (but, preferably, closer to the apex release assembly 690). This coupling would have a proximal portion rotationally fixedly connected to the to the apex release lumen 640 when the apex release assembly 690 is in the locked position shown in FIGS. 15 and 16 and a freely-rotatable distal portion that is fixedly connected to all of the guidewire lumen 620 disposed distal thereto. Thus, the guidewire lumen 620 near the sheath assembly 650 will always be freely rotatable and, thereby, allow easy and torque-free rotation of the guidewire lumen 620 about the guidewire 610.

Figure 69:
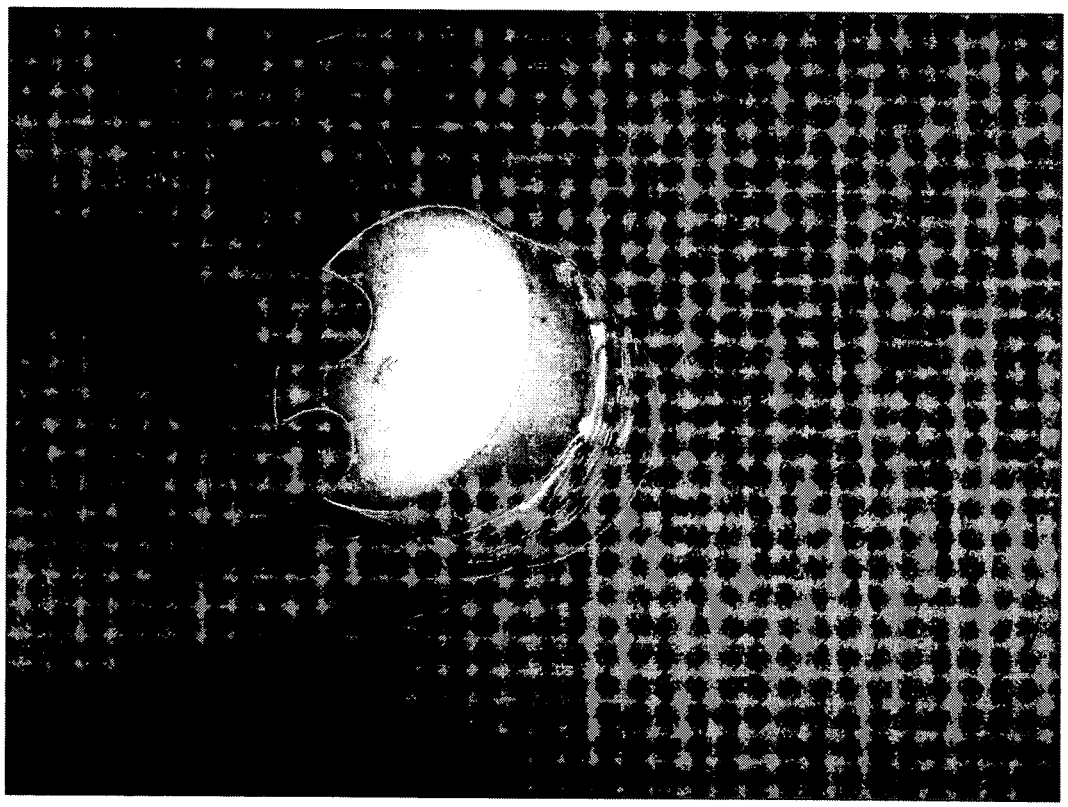
FIG. 69 is a photograph of a user bending a stent graft assembly around a curving device to impart a curve to a guidewire lumen therein.

It is also noted that the pre-curved section 622 of the guidewire lumen need not be made at the manufacturer. As shown in FIG. 69, a curving device can be provided with the delivery system 600 to allow the physician performing the implantation procedure to tailor-fit the curve 622 to the actual curve of the vessel in which the stent graft 1 is to be implanted. Because different patients can have different aortic arch curves, a plurality of these curving devices can be provided with the delivery system 600, each of the curving devices having a different curved shape. Each device can also have two sides with each side having a different curved shape, thus, reducing the number of devices if a large number of curves are required. Further, the curving devices can all be rotationally connected on a common axle or spindle for each of transport, storage, and use.

For tailoring the curve to the patient's curved vessel, the physician can, for example, fluoriscopically view the vessel (e.g., aortic arch) and determine therefrom the needed curve by, for example, holding up the curving device to the display. Any kind of curving device can be used to impart a bend to the guidewire lumen 620 when the guidewire lumen 620 is bent around the circumference.

Because of the predefined curvature of the support member 40, the support member 40 cannot align exactly and entirely along the superior longitudinal line of the curved aorta. Accordingly, an optimal superior surface position of the support member 40 places as much of the central portion of the support member 40 (between the two ends 47 thereof) as possible close to the superior longitudinal line 808 of the curved aorta. A particularly desirable implantation position has the superior longitudinal line 808 of the curved aorta intersecting the proximal half of the support member 40—the proximal half being defined as that portion of the support member 40 located between the centerline 45 and the proximal support member loop 47. However, for adequate implantation purposes, the centerline 45 of the support member 40 can be as much as seventy circumferential degrees away from either side of the superior longitudinal line of the curved aorta.

When the stent graft 1 is in place both longitudinally and circumferentially (FIG. 21), the stent graft 1 is ready to be removed from the inner sheath 652 and implanted in the vessel 700. Because relative movement of the stent graft 1 with respect to the vessel is no longer desired, the inner sheath 652 needs to be retracted while the stent graft 1 remains in place, i.e., no longitudinal or circumferential movement. Such immovability of the stent graft 1 is insured by, first, the apex capture device 634 of the nose cone assembly 630 holding the front of the stent graft 1 by its bare stent 30 (see FIGS. 13, 22, and 23) and, second, by unlocking the locking ring 676/placing the locking ring/knob in the D position—which allows the sheath lumen 654 to move independently from the guidewire lumen 620, apex release lumen 640, and graft push lumen 642. The apex capture device 634, as shown in FIGS. 13, 14, 30 and 311 (and as will be described in more detail below), is holding each individual distal apex 32 of the bare stent 30 in a secure manner—both rotationally and longitudinally.

The nose cone assembly 630, along with the apex capture device 634, is securely attached to the guidewire lumen 620 (and the apex release lumen 640 at least until apex release occurs). The inner sheath 652 is securely attached to a sheath lumen 654, which is coaxially disposed around the guidewire lumen 620 and fixedly attached to the proximal handle 678. The stent graft 1 is also supported at its distal end by the graft push lumen 642 and the distal sleeve 644 or the taper 653 of the inner sheath 652. (The entire coaxial relationship of the various lumen 610, 620, 640, 642, 654, and 660 is illustrated for exemplary purposes only in FIG. 25, and a portion of which can also be seen in the exploded view of the handle assembly in FIG. 50) Therefore, when the proximal handle 678 is moved proximally with the locking ring 676 in the deployment position D, the sheath lumen 654 moves proximally as shown in FIGS. 13, 22, and 23, taking the sheath 652 proximally along with it while the guidewire lumen 620, the apex release lumen 640, the graft push lumen 642, and the distal sleeve 644 remain substantially motionless and, therefore, the stent graft 1 remains both rotationally and longitudinally steady.

The stent graft 1 is, now, ready to be finally affixed to the aorta 700. To perform the implantation, the bare stent 30 must be released from the apex capture device 634. As will be described in more detail below, the apex capture device 634 shown in FIGS. 13, 14, and 29 to 32, holds the proximal apices 32 of the bare stent 30 between the distal apex head 636 and the proximal apex body 638. The distal apex head 636 is fixedly connected to the guidewire lumen 620. The proximal apex body 638, however, is fixedly connected to the apex release lumen 640, which is coaxial with both the guidewire lumen 620 and the sheath lumen 654 and disposed therebetween, as illustrated diagrammatically in FIG. 25. (As will be described in more detail below, the graft push lumen 642 is also fixedly connected to the apex release lumen 640.) Therefore, relative movement of the apex release lumen 640 and the guidewire lumen 620 separates the distal apex head 636 and a proximal apex body 638 from one another.

To cause such relative movement, the apex release assembly 690 has, in a preferred embodiment, three parts, a distal release part 692, a proximal release part 694, and an intermediate part 696 (which is shown in the form of a clip in FIGS. 16 and 26). To insure that the distal apex head 636 and the proximal apex body 638 always remain fixed with respect to one another until the bare stent 30 is ready to be released, the proximal release part 694 is formed with a distal surface 695, the distal release part 692 is formed with a proximal surface 693, and the intermediate part 696 has proximal and distal surfaces corresponding to the surfaces 695, 693 such that, when the intermediate part 696 is inserted removably between the distal surface 695 and the proximal surface 693, the intermediate part 696 fastens the distal release part 692 and the proximal release part 694 with respect to one another in a form-locking connection. A form-locking connection is one that connects two elements together due to the shape of the elements themselves, as opposed to a force-locking connection, which locks the elements together by force external to the elements. Specifically, as shown in FIG. 26, the clip 696 surrounds a distal plunger 699 of the proximal release part 694 that is inserted slidably within a hollow 698 of the distal release part 692. The plunger 699 of the proximal release part 694 can slide within the hollow 698, but a stop 697 inside the hollow 698 prevents the distal plunger 699 from withdrawing from the hollow 698 more than the longitudinal span of the clip 696.

To allow relative movement between the distal apex head 636 and the proximal apex body 638, the intermediate part 696 is removed easily with one hand and, as shown from the position in FIG. 16 to the position in FIG. 17, the distal release part 692 and the proximal release part 694 are moved axially towards one another (preferably, the former is moved towards the latter). Such movement separates the distal apex head 636 and the proximal apex body 638 as shown in FIG. 14. Accordingly, the distal apices 32 of the bare stent 30 are free to expand to their natural position in which the bare stent 30 is released against the vessel 700.

Of course, the apex release assembly 690 can be formed with any kind of connector that moves the apex release lumen 640 and the guidewire lumen 620 relative to one another. In a preferred alternative embodiment, for example, the intermediate part 696 can be a selectable lever that is fixedly connected to either one of the distal release part 692 or the proximal release part 694 and has a length equal to the width of the clip 696 shown in FIG. 26. Thus, when engaged by pivoting the lever between the distal release part 692 and the proximal release part 694, for example, the parts 692, 694 cannot move with respect to one another and, when disengaged by pivoting the lever out from between the parts 692, 694, the distal release part 692 and the proximal release part 694 are free to move towards one another.

The apex capture device 634 is unique to the present invention in that it incorporates features that allow the longitudinal forces subjected on the stent graft 1 to be fully supported, through the bare stent 30, by both the guidewire lumen 620 and apex release lumen 640. Support occurs by providing the distal apex head 636 with a distal surface 639—which surface 639 supports the proximal apices 32 of the bare stent 30 (shown in the enlarged perspective view of the distal apex head 636 in FIG. 29). When captured, each proximal apex 32 of the bare stent 30 separately rests on a distal surface 639, as more clearly shown in FIGS. 30 and 31. The proximal spokes of the distal apex head 636 slide within the fingers of the proximal apex body 638 as these parts moves towards one another. A slight space, therefore, exists between the fingers and the outer circumferential surfaces of the spokes. To insure that the bare stent 30 does not enter this space (which would prevent a proper release of the bare stent 30 from the apex capture device 634, a radial thickness of the space must be less than the diameter of the wire making up the bare stent 30. Preferably, the space is no greater than half a diameter of the wire.

Figure 32:
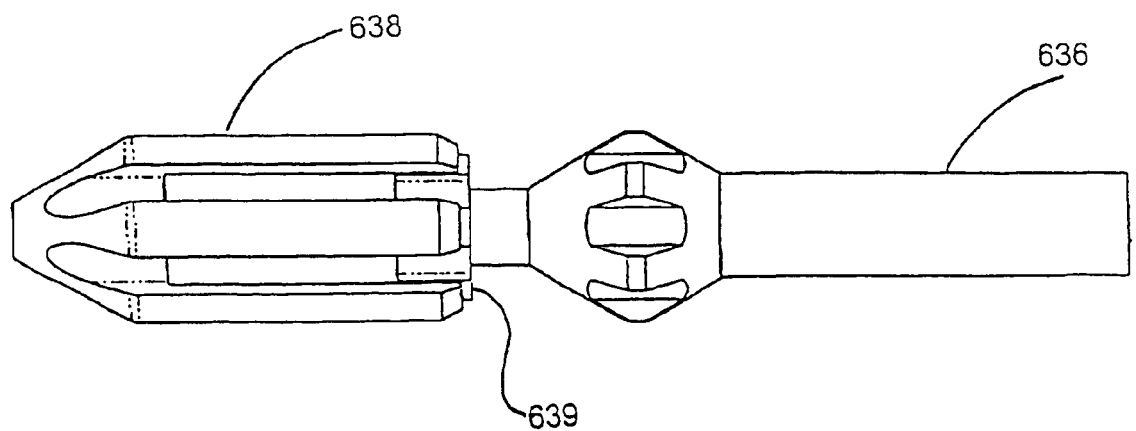
FIG. 32 is a fragmentary side elevational view of the distal apex head and proximal apex body of FIG. 30 in the released position.

Having the distal surface 639 be the load-bearing surface of the proximal apices 32 ensures expansion of each and every one of the distal apices 32 from the apex release assembly 690. The proximal surface 641 of the distal apex head 636 (see FIG. 30) meets with the interior surfaces of the proximal apex body 638 to help carry the apex load because the apices of the bare stent 30 are captured therebetween when the apex capture device 634 is closed. Complete capture of the bare stent 30, therefore, fully transmits any longitudinal forces acting on the bare stent 30 to both the guidewire lumen 620 and apex release lumen 640, making the assembly much stronger. Such capture can be clearly seen in the cut-away view of the proximal apex body 638 in FIG. 31. For release of the apices 32 of the bare stent 30, the proximal apex body 638 moves leftward with respect to FIGS. 30 to 33 (compare FIGS. 30 and 31 with FIG. 32). Because friction exists between the apices 32 and the "teeth" of the proximal apex body 638 when the apices 32 are captured, the apices 32 will also try to move to the left along with the proximal apex body 638 and, if allowed to do so, possibly would never clear the "teeth" to allow each apex 32 to expand. However, as the proximal apex body 638 disengages (moves in the direction of arrow C in FIG. 31), direct contact with the distal surface 639 entirely prevents the apices 32 from sliding in the direction of arrow C along with the proximal apex body 638 to ensure automatic release of every captured apex 32 of the bare stent 30. Because the proximal apex body 638 continues to move in the direction of arrow C, eventually the "teeth" will clear their respective capture of the apices 32 and the bare stent 30 will expand entirely. The release position of the distal apex head 636 and the proximal apex body 638 is shown in FIGS. 14 and 32, and corresponds to the position of the apex release assembly 690 in FIG. 17. As can be seen, tapers on the distal outer surfaces of the proximal apex body 638 further assist in the prevention of catching the proximal apices 32 of the bare stent 30 on any part of the apex capture device 634. In this configuration, the distal surfaces 639 bear all the load upon the bare stent 30 and the fingers of the proximal apex body 638.

Simply put, the apex capture device 634 provides support for load placed on the stent graft 1 during advancement A of the inner sheath 652 and during withdrawal of the inner sheath 652 (i.e., during deployment D). Such a configuration benefits the apposition of the bare stent 30 by releasing the bare stent 30 after the entire graft sleeve 10 has been deployed, thus reducing the potential for vessel perforation at the point of initial deployment.

When the stent graft 1 is entirely free from the inner sheath 652 as shown in FIG. 24, the proximal handle 678 is, then, substantially at or near the third position (deployment position) shown in FIG. 10.

The stent graft 1 is, now, securely placed within the vessel 700 and the entire portion 630, 650, 660 of the assembly 600 may be removed from the patient.

While the preferred embodiments of the invention have been illustrated and described, it will be clear that the invention is not so limited. Numerous modifications, changes, variations, substitutions, and equivalents will occur to those skilled in the art without departing from the spirit and scope of the present invention as defined by the appended claims.

We claim:
1. A method of implanting a prosthesis in a patient at a treatment site, comprising the steps of:
  a) axially locking an apex release lumen, a sheath lumen and a curved guidewire lumen located within the apex release lumen with respect to an outer catheter, wherein an inner sheath extends from a distal end of the sheath lumen and radially about the prosthesis, at least one of the apex release lumen and the sheath lumen constraining a proximal stent of the prosthesis and wherein the apex release lumen is within the sheath lumen and the sheath lumen is within the outer catheter;
  b) rotationally locking the apex release lumen, the sheath lumen and the curved guidewire lumen, whereby they rotate together and independently of the outer catheter;
  c) threading the apex release lumen, the sheath lumen and the curved guidewire lumen onto a guidewire and directing the apex release lumen, the sheath lumen and the curved guidewire lumen into a patient to place the outer catheter in an aorta of the patient at a point distal to the treatment site at a distance that is greater than the length of the prosthesis;
  d) axially unlocking the apex release lumen, the sheath lumen and the curved guidewire lumen with respect to the outer catheter;
  e) advancing the apex release lumen, the sheath lumen and the curved guidewire lumen distally out of the outer catheter in the aorta toward the patient's heart whereby the advancement of the apex release lumen, the sheath lumen and the curved guidewire lumen causes rotation of the prosthesis to thereby rotationally align the prosthesis at the treatment site, thereby delivering the prosthesis to the treatment site in proper rotational alignment; and
  f) axially locking the apex release lumen and the curved guidewire lumen relative to the outer catheter, whereby the sheath lumen can move axially relative to the apex release lumen and the outer catheter; and
  g) retracting the inner sheath in a proximal direction to at least partially implant the prosthesis in the vessel.
2. The method according to claim 1, wherein the inner sheath is of a more flexible material than that of the outer catheter.
3. The method according to claim 1, wherein the apex release lumen and the sheath lumen are advanced distally out of the outer catheter and into the thoracic aorta.
4. The method according to claim 3, wherein the prosthesis includes a supporting rod, whereby advancement of the rotationally locked apex release lumen, the sheath lumen and the curved guidewire lumen causes rotational alignment of a longitudinal support member of the prosthesis along a superior longitudinal line of a portion of the thoracic aorta.
5. A method of implanting a prosthesis in a patient at a treatment site, comprising the steps of:
  a) axially locking an apex release lumen, a sheath lumen and a curved guidewire lumen located within the apex release lumen with respect to an outer catheter, wherein an inner sheath extends from a distal end of the sheath lumen and radially about the prosthesis, the inner sheath constraining the prosthesis and wherein the apex release lumen is within the sheath lumen and the sheath lumen is within the outer catheter;
  b) rotationally locking the apex release lumen, the sheath lumen and the curved guidewire lumen, whereby they rotate together and independently of the outer catheter;
  c) threading the apex release lumen, the sheath lumen and the curved guidewire onto a guidewire and directing the apex release lumen and the sheath lumen into a patient to place the outer catheter into an aorta of the patient;

d) axially unlocking the apex release lumen, the sheath lumen and the curved guidewire lumen with respect to the outer catheter;

e) advancing the apex release lumen, the sheath lumen and the curved guidewire lumen distally out of the outer catheter in the aorta toward the patient's heart, whereby the advancement of the apex release lumen, the sheath lumen and the curved guidewire lumen causes rotation of the prosthesis to thereby rotationally align the prosthesis at the treatment site, thereby delivering the prosthesis to the treatment site in proper rotational alignment;

f) axially locking the apex release catheter and the curved guidewire lumen relative to the outer catheter, whereby the sheath lumen can move axially relative to the apex release lumen and the outer catheter; and g) retracting the sheath lumen and the inner sheath to release the prosthesis from the inner sheath.

6. The method of claim 5, wherein a proximal portion of the prosthesis is fixed at an apex capture device at proximal apices of a stent component of the prosthesis, the apex capture device including:

a) a distal apex head fixedly connected to a distal end of the curved guidewire lumen, the distal apex head having:
  i) a distal portion with a proximal end; and
  ii) a proximal portion having an exposed side facing distally that is disposed in a plane substantially perpendicular to a longitudinal axis of the apex release lumen and defining stopping surface portions, and b) a proximal apex body fixedly connected to a distal end of the apex release lumen and having fingers extending toward the distal apex head in a distal direction, the fingers defining at least in part an interior cavity shaped to receive the proximal portion of the distal apex head therein, and the proximal apex body and the distal apex head being formed to hold at least one apex of the stent component of the prosthesis therebetween and, together, defining a stent captured state in which the proximal portion of the distal apex head is received in the interior cavity of the proximal apex body.

7. The method of claim 5, wherein the prosthesis is further constrained by the apex release lumen and further including the step of releasing the prosthesis from the apex release lumen.

8. A method for treating an aneurysm of a patient by deploying a prosthesis from a delivery device, comprising the steps of:

a) advancing an outer catheter locked in a neutral position of the delivery device with respect to an apex release lumen, a sheath lumen and a curved guidewire lumen located within the apex release lumen, wherein an inner sheath extends from a distal end of the sheath lumen and radially about a prosthesis within the outer catheter, wherein the apex release lumen is within the sheath lumen and the sheath lumen is within the outer catheter, the outer catheter, the apex release lumen, the sheath lumen and the curved guidewire lumen moving along a guidewire through an arterial access to a treatment site in an aorta of the patient;

b) rotationally locking the apex release lumen, the sheath lumen and the curved guidewire lumen, whereby they rotate together and independently of the outer catheter;

c) axially unlocking the apex release lumen, the sheath lumen and the curved guidewire lumen relative to the outer catheter, thereby shifting the delivery device from the neutral position to an advancement position;

d) advancing the apex release lumen, the sheath lumen and the curved guidewire lumen distally out of the outer catheter in the aorta toward the patient's heart to thereby deliver the prosthesis to the treatment site, whereby advancing the inner sheath, the apex release lumen and the curved guidewire lumen causes rotation of the prosthesis to thereby rotationally align the prosthesis at the treatment site;

e) axially unlocking the sheath lumen from the apex release lumen and locking the apex release lumen and the curved guidewire lumen relative to the outer catheter, whereby the sheath lumen can move axially relative to the apex release lumen and the outer catheter to thereby shift from the advancement position to a deployment position of the delivery device;

f) partially retracting the sheath lumen, thereby partially retracting the inner sheath from the prosthesis to partially deploy the prosthesis, the prosthesis being fixed at an apex capture device of the delivery device at proximal apices of a stent component of the prosthesis, the apex capture device including, 1) a distal apex head fixedly connected to a distal end of the curved guidewire lumen of the delivery device within the apex release lumen, the apex head having
  i) a distal portion with a proximal end, and
  ii) a proximal portion having an exposed side facing distally that is in a plane approximately perpendicular to a longitudinal axis of the apex release lumen, and defining stopping surface portions, and 2) a proximal apex body fixedly connected to a distal end of the apex release lumen and having fingers extending toward the distal apex head in a distal direction, the fingers defining an interior cavity shaped to receive the proximal portion of the distal apex head therein, the proximal apex body and the distal apex head being formed to hold at least one apex of the stent component of the prosthesis therebetween and, together, defining a stent captured state in which the proximal portion of the distal apex head is received in an interior cavity of the apex capture device and the distal apex head approximately closes off the interior cavity along the longitudinal axis of the apex release lumen to capture at least one apex of the stent component of the prosthesis;

g) positioning the proximal end of the prosthesis within the aorta while the prosthesis is partially deployed;

h) retracting the sheath lumen and the inner sheath to fully expose the prosthesis within the aorta;

i) retracting the apex release lumen relative to the curved guidewire lumen, thereby releasing at least one apex of the stent from the stent captured state, whereby the stent expands to fix the proximal portion of the prosthesis and is released from the delivery device within the aorta; and j) retracting the device from the aorta and the arterial access of the patient.

9. The method of claim 8, wherein the arterial access is a femoral artery.

10. The method of claim 8, wherein the aorta is a curved portion of the aorta.

11. The method of claim 10, wherein the curved portion of the aorta is a portion of a thoracic aorta.

12. The method of claim 11, wherein the prosthesis includes a longitudinal support member that extends substantially parallel to a longitudinal axis of the prosthesis, whereby advancement of the rotationally locked apex release lumen, the sheath lumen and the curved guidewire lumen causes rotational alignment of the prosthesis to thereby align the longitudinal support member with a superior longitudinal line of the curved portion of the aorta.

13. The method of claim 12, wherein the prosthesis further includes at least one radiopaque marker.

14. The method of claim 13, wherein the radiopaque marker is a D-shaped radiopaque marker.

* * * * *